(12) United States Patent
Pasmans et al.

(10) Patent No.: US 9,125,855 B2
(45) Date of Patent: Sep. 8, 2015

(54) **PREVENTION OF *SALMONELLA* RECRUDESCENSE**

(75) Inventors: Frank Pasmans, Sint-Pieters-Kapelle (BE); Elin Verbrugghe, Wevelgem (BE); Freddy Haesebrouck, Heist-aan-Zee (BE); Filip Eddy Boyen, Hekelgem (BE)

(73) Assignee: Universiteit Gent, Gent (BL)

( * ) Notice: Subject to any disclaimer, the term of this patent is extended or adjusted under 35 U.S.C. 154(b) by 0 days.

(21) Appl. No.: 14/235,655

(22) PCT Filed: Jul. 27, 2012

(86) PCT No.: PCT/EP2012/064762
§ 371 (c)(1),
(2), (4) Date: Jan. 28, 2014

(87) PCT Pub. No.: WO2013/014261
PCT Pub. Date: Jan. 31, 2013

(65) Prior Publication Data
US 2014/0212454 A1  Jul. 31, 2014

(30) Foreign Application Priority Data

Jul. 28, 2011 (EP) ................................... 11175745
Mar. 22, 2012 (EP) ................................... 12160785

(51) Int. Cl.
| | | |
|---|---|---|
| *A61K 39/112* | (2006.01) | |
| *A61K 39/02* | (2006.01) | |
| *A61K 41/00* | (2006.01) | |
| *C07K 14/195* | (2006.01) | |
| *A61K 39/00* | (2006.01) | |

(52) U.S. Cl.
CPC ............ *A61K 39/0275* (2013.01); *C07K 14/195* (2013.01); *A61K 2039/522* (2013.01); *A61K 2039/552* (2013.01)

(58) Field of Classification Search
CPC .................................................. A61K 39/0275
USPC ............... 424/93.1, 93.2, 200.1, 234.1, 258.1
See application file for complete search history.

(56) References Cited

U.S. PATENT DOCUMENTS

| | | |
|---|---|---|
| 6,610,836 B1 | 8/2003 | Breton et al. |
| 7,041,814 B1 | 5/2006 | Weinstock et al. |
| 7,314,974 B2 | 1/2008 | Cao et al. |

FOREIGN PATENT DOCUMENTS

WO    01/66572 A2    9/2001

OTHER PUBLICATIONS

Fricke, W. et al.; Comparative Geomics of 28 *Salmonella enterica* Isolates: Evidence for CRISPR-Mediated Adaptive Sublineage Evolution; Journal of Bacteriology, Jul. 2011; pp. 3556-3568; vol. 193, No. 14; American Society for Microbiology.

Gupta, S. et al.; A *Salmonella typhimurium* Genetic Locus Which Confers Copper Tolerance on Copper-Sensitive Mutants of *Escherichia coli*; Journal of Bacteriology; Aug. 1997; pp. 4977-4984; vol. 179, No. 16; American Society for Microbiology.

Rump, L.V. et al.; Draft Genome Sequences of Six *Escrichia coli* Isolates from the Stepwise Model of Emergence of *Escherichia coli* O157:H7; Journal of Bacteriology; Apr. 2011; pp. 2058-2059; vol. 193, No. 8; American Society for Microbiology.

Richardson, E. et al.; Genome Sequences of *Salmonella enterica* Serovar *typhimurium, choleraesius*, Dublin, and Gallinarum Strains of Well-Defined Virulence in Food-Producing Animals; Journal of Bacteriology; Jun. 2011; pp. 3162-3163; vol. 193, No. 12; American Society for Microbiology.

European Search Report dated May 21, 2012 pertaining to European Application No. 11175745.6.

Leyman, B. et al.; *Salmonella typhimurium* LPS mutations for use in vaccines allowing differentation of infected and vaccinated pigs; Vaccine; May 1, 2011; pp. 3679-3685; vol. 29; Elsevier.

International Search Report and Written Opinion dated Oct. 24, 2012 pertaining to International Application No. PCT/EP2012/064792.

Bearson, B. et al.; The role of the QseC quorum-sensing sensor kinase in colonization and norepinephrine-enhanced motility of *Salmonella enterica* serovar *typhimurium*; Microbial Pathogenesis; Apr. 2008; pp. 271-278; vol. 44; Elsevier Ltd.

Berends, B.R. et al.; Identification and quantification of risk factors in animal management and transport regarding *Salmonella* spp. in pigs; International Journal of Food Microbiology; Jun. 1996; pp. 37-53; vol. 30; Elsevier Science B.V.

Boyen, F. et al.; The fibronectin binding protein ShdA is not a prerequisite for long term faecal shedding of *Salmonella typhimurium* in pigs: Veterinary Microbiology; Jun. 15, 2006; pp. 284-290; vol. 115; Elsevier B.V.

Boyen, F. et al.; A limited role for SsrA/B in persistent *Salmonella typhimurium* infections in pigs; Veterinary Microbioiogy; Apr. 30. 2008; pp. 364-373; vol. 128; Elsevier B.V.

Boyen, F. et al.; Non-typhiodal *Salmonella* infections in pigs: A closer look at epidemiology, pathogenesis and control; Veterinary Microbiology; Jul. 27, 2008; pp. 1-19; vol. 130; Elsevier B.V.

Boyen, F. et al.; Quorum sensing in veterinary pathogens: Mechanisms, clinical importance and future perspectives; Veterinary Microbiology; Mar. 30, 2009; pp. 187-195; vol. 135; Elsevier B.V.

Boyen. F. et al.; Porcine in vitro and in vivo models to assess the virulence of *Salmonella enterica* serovar *typhimurium* for pigs; Laboratory Animals; Jan. 1, 2009; pp. 46-52; vol. 43.

Bradshaw, R. H. et al.; Behavioural and hormonal responses of pigs during transport: effect of mixing and duration of journey; Animal Science; 1996; pp. 547-554; vol. 62; British Society of Animal Science.

(Continued)

*Primary Examiner* — Rodney P Swartz
(74) *Attorney, Agent, or Firm* — Dinsmore & Shohl LLP

(57) ABSTRACT

The present invention relates to novel *Salmonella* mutants, to a process for producing the same and to vaccines containing the same, wherein said *Salmonella* mutants are characterized in that they are not responsive to stress-related recrudescence. It is accordingly an object of the present invention to provide the use of said *Salmonella* mutants in the vaccination of animals, in particular mammals and birds, more in particular pigs, poultry and cattle.

21 Claims, 20 Drawing Sheets

(56) References Cited

OTHER PUBLICATIONS

Donne, E. et al.; Survival of *Salmonella* serovar *typhimurium* inside porcine monocytes is associated with complement binding and suppression of the production of reactive oxygen species; Veterinary Microbiology; May 20, 2005; pp. 205-214; vol. 107; Elsevier B.V.

Jensen-Waern, M. et al.; Valuable Indicators of Physical Stress in Porcine Plasma; Journal of Veterinary Medicine A, Dec. 1993; pp. 321-327; vol. 40; Paul Pavey Scientific Publishers.

Hurd, H.S. et al; *Salmonella enterica* Infections in Market Swine with and without Transport and Holding; Applied and Environmental Microbiology; May 2002; pp. 2376-2381; vol. 68, No. 5; American Society for Microbiology.

Lundberg, U et al.; Growth Phase-Regulated Induction of *Salmonella*-Induced Macrophage Apoptosis Correlates with Transient Expression of SPI-1 Genes; Journal of Bacteriology; Jun. 1999; pp. 3433-3437; vol. 181, No. 11; American Society for Microbiology.

Methner, U. et al.; Effect of norepinephrine on colonisation and systemic spread of *Salmonella enterica* in infected animals: Role of catecholate siderophore precursors and degradation products; International Journal of Medical Microbiology; Jul. 1, 2008; pp. 429-439; vol. 298; Elsevier GmbH.

Nakamura, M. et al.; Evaluation of the Efficacy of a Bacterin against *Salmonella enteritidis* Infection and the Effect of Stress after Vaccination; Avian Diseases; Oct.-Dec. 1994; pp. 717-724; vol. 38.

Stabel, T.J. et al.; Effect of 2-deoxy-D-glucose induced stress on *Salmonella choleraesuis* shedding and persistence in swine; Research in Veterinary Science; Jun. 2004; pp. 187-194; vol. 76; Elsevier Ltd.

Van Parys, A. et al.; Tissue-Specific *Salmonella typhimurium* Gene Expression during Persistence in Pigs; PLoS One; Aug. 2011; pp. 1-11; vol. 6, Issue 8.

Verbrugghe, E. et al.; Stress induced *Salmonella typhimurium* recrudescence in pigs coincides with cortisol induced increased intracellular proliferation in macrophages; Veterinaly Research; Dec. 7, 2011; pp. 1-10; vol. 42:118.

Wallis, T.S.; *Salmonella* Pathogensis and Immunity: We Need Effective Multivalent Vaccines; The Veterinary Journal; Mar. 2001; pp. 104-106; Issue 161; Harcourt Publishers Ltd.

Wei, S. et al.; Curcumin attenuates the effects of transport stress on serum cortisol concentration, hippocampal NO production, and BDNF expression in the pig; Domestic Animal Endocrinology; Nov. 2010; pp. 231-239; vol. 39; Elsevier Inc.

Williams Jr., L. et al.; *Salmonella* Excretion in Joy-Riding Pigs; American Journal of Public Health; May 1970; pp. 926-929; vol. 60, No. 5.

Wong, L. et al.; Epidemiology and control measures for *Salmonella* in pigs and pork; Livestock Production Science; Sep. 2002; pp. 215-222; vol. 76, Elsevier Science B.V.

Worsaae, H. et al.; Plasma Cortisol and Behaviour in Early Weaned Piglets; Acta vet. scand.; 1980; pp. 640-657, vol. 21.

Ygberg, S. et al.: Polynucleotide Phosphorylase Negatively Controls spy Virulence Gene Expression in *Salmonella enterica*; Infection and Immunity; Feb. 2006; pp. 1943-1254; vol. 74, No. 2; American Society for Microbiology.

Figure 6 cbpA nucleic acid sequence:

TATGCTTTCCCCCATTGCTGGCGTGGGTCAAAGGACGACTGCGCGTCCGCCAGTTGTTGCCA
CAGGGCAGCTGTTTTCTCGTCAGGTTTCGGCGGCATAACGATTTTGATGATGGCATAGAGAT
CGCCAGTGTGCTTTTTACTGGCTAATCCTTTTCCTTTGATACGCAGCCGCTGACCTGCCTGG
CTGCCGGGGGGAATGGTCAGCAAAATACGCTCTTTAAGCGTTGGCACAGACACCTTAGCGCC
GAGCGCCGCCTCCCATGGGGCAAGCGGAAGGACGACTTCCAGATCCTGATTGACGATATCAA
AGAGCGGATGCGGGGCAATATGGATAACGAGCCATAAATCGCCATTAGGTCCGCCGTTTTCC
CCCGGCGTGCCCTGGCCTTTCAGTCTGATTCGTTGCCCGTTGCTGACGCCAGCCGGGATTTT
CACATTCAATGTCTTGGGAATTTCCCGCTCCACCAGGCCGAACGCGTTATAAACGGGGACGG
AATAGCTAATCGTACGCTGGTGCTCTTCCAGCGTTTCTTCCAGGAATACCGCCACTTCAATT
TCGATATCATGACCGCGTGCGGCGTGGCGGTGATGCGAATGGCGACCGTGCTGACCAAAAAT
AGACGAGAAAATATCATCAAAATCTTCAGCGTTATACGGCTGGCCTTCGTGTTGCTGGAACT
GGCGATTAAATTGTGGATCGTTACGGTGTTGCCATAACTGGTCATACTCGGCGCGCCGTTGC
TCATCACTCAGCACTTCCCATGCTTCAGCAACCTCTTTGAAACGGGCTTCGGCATCGGGTTC
TTTGCTGACATCTGGATGGTACTTGCGGGCCAGTCGGCGATAGGCGGTCTTAATCGTCTTGA
GATCGTCCGTCGGTTTCACGCCCATAATGGCGTAATAATCCTTAAGTTCCAT (SEQ ID NO:
1)

scsA nucleic acid sequence:

ATGGCGAAACAACAACGGATGGGCTGGTGGTTTCTTTGCCTTGCATGTGTCGTGGTAATGGT
TTGTACCGCGCAACGCATGGCGGGCCTGCACGCCTTGCAGATGCAGGCGACGGCCTCTGCTG
CGGTGGTCAGCGCTCCCTCCTCGACAGATGACGGCTCGCCGGTCACCCCCTGCGAATTAAGC
GCCAAGTCGCTGCTGGCGGCGCCTCCGGTACTCTTTGAAGGCGCTATCCTTGCGCTTTGTCT
ACTGCTTTCCTTACTGGCGCCTGTCCGGGTCATGCGCCTGCCGTTTTCGCCTCCACGGGCTA
TTTCGCCGCCCACATTACGGGTACATCTACGATTTTGTGTCTTCCGTGAATGA (SEQ ID
NO: 2)

scsB nucleic acid sequence:

ATGATGATTTTGTTCAGGCGGATACTGTTCTGCCTGTTATGGCTTTGGCTGCCCGTCTCCTG
GGCGGCGGAAAGCGGCTGGCTGCGTTCGCCCGATAACGACCATGCCAGCATACGGCTACGTG
CCGATACGTCCGCTAACGGTGAGACCCGGCTGTTGCTGGATGTCAAACTGGAAAACGGCTGG
AAAACCTACTGGCGCGCGCCGGGGAAGGGGCGTGGCACCCTCTATCGCCTGGAAAGGCGA
CATGCCTGAGGTAAGCTGGTTCTGGCCAACCCCCTCGCGCTTTGATGTGGCGAATATCACCA
CCCAGGGATATCACGACGAGGTGACCTTTCCGATGATCGTGCGCGGTACGCTGCCGGCGACC
TTGCGCGGTGTGTTGACGTTATCAACCTGCAGCAATGTTTGTCTGTTGACCGATTACCCCTT
TTCCGTGACGCCTACTGTGCAGAATGCCGATTTTGCCCATGACTATGCGCGGCGATGGGTA
AAATTCCGCTCCGCAGTGGACTAACGGACTCGCTTGACGTCGGCTATCGCCCGGGAGAACTG

Figure 6 – cont 1

```
GTGGTCACTGCTACGCGAGCGGCGGGCTGGTCATCGCCCGGGCTCTATCTTGACACCGTAGA
TGACGTCGATTTTGCGAAGCCTCGTCTGCGCGTAGAGGGCGACAGGTTACAGGCGACGGTGC
CGGTGACGGACAGTTGGGGCGAAAAGGCGCCCGATTTGCGCAACAAATCGCTGACCCTCGTG
TTAGCCGATGGCGCTATCGCCCAGGAGAGCACGCAAACCATTGGCACTGCGCCAGCGCAAAC
GCCGGACAATGCGGCGCTACCTTTCTGGCAAGTTGTAATGATGGCGCTGATCGGCGGACTGA
TTCTTAATTTAATGCCCTGCGTACTGCCGGTTCTGGGCATGAAGCTTGGCTCTATTTTATTG
GTAGAGGAAAAAAGCCGCTCTCACATCAGGCGACAATTTTTGGCTTCGGTCGCCGGTATCAT
TGCGTCATTTATGGCGCTGGCGGCGTTTATGACCCTCCTTCGCCTGTCAAACCATGCGCTGG
CCTGGGGAGTCCAGTTCCAGAATGTATGGTTTATTGGTTTTATGGCGCTGGTGATGTTGTTG
TTTAGCGCCAGCCTGTTCGGGCTTTTTGAGTTCAGGCTTCCCTCATCTATGACCACGAAACT
GGCCACTTACGGCGGTAACGGTATGTCGGGACATTTCTGGCAGGGGGCATTCGCCACGCTGC
TGGCGACGCCTTGTAGCGCGCCGTTTCTGGGCACGGCGGTCGCCGTGGCGCTCACGGCGTCG
CTGCCGACGCTGTGGGGCTGTTCCTTGCGCTTGGCCTGGGGATGAGCGCGCCGTGGCTACT
GGTCGCGATACGACCAGGGCTTGCGCTACGTTTACCGCGCCCGGGCGTTGGATGAATGTCC
TGCGCAGGATCCTCGGTCTGATGATGCTGGGGTCGGCTATCTGGCTGGCGACGTTACTCCTG
CCGCATTTCGGCTTCACTGCGTCAAAGAGCGCGCAAGACACGGTTCAGTGGCAACCGTTGAG
TGAACAGGCAATCCAGTCGGCGCTGGCGCAGCATAAGCGGGTATTTGTCGATGTCACTGCGG
ACTGGTGTATTACCTGTAAAGTGAATAAATACAACGTCCTGCAAAAAGAGGATGTGCAGGCC
GCCTTGCAACAGCCGGATGTTGTGGCGCTGCGGGGAGACTGGACGCTGCCGTCCGATGCCAT
TACAGATTTTCTGAAAACGCGCGGCCAGGTCGCCGTGCCGTTTAATCAGGTATATGGCCCCG
GCTTGCCGGAAGGGGAGGCACTGCCCACTTTGCTGACCCGCGATGCGGTATTACAAACGTTG
AAAAAAGCGAAAGGAATAACCCAATGA (SEQ ID NO: 3)
``` scsC nucleic acid sequence:

```
ATGAAATACATGATTGTTTTACTGCTGGCGCTGTTTTCGACGCTGAGCATCGCGCAAGAAAC
CGCTCCTTTTACGCCGGATCAGGAAAAGCAGATTGAAAATCTGATCCATGCGGCGTTGTTTA
ACGATCCTGCCAGCCCGCGGATAGGCGCTAAACACCCTAAGCTGACGCTGGTGAACTTTACG
GATTACAACTGCCCGTACTGCAAACAGCTCGATCCGATGCTGGAAAAGATTGTGCAGAAATA
TCCTGACGTTGCGGTCATTATTAAACCGCTGCCATTTAAAGGAGAGAGTTCCGTTCTGGCGG
CGCGTATTGCGCTGACCACCTGGCGCGAGCATCCGCAACAGTTCCTCGCGCTACATGAAAAA
CTCATGCAAAAGCGCGTTTACCATACGGATGACAGTATTAAACAGGCCCAGCAGAAAGCAGG
GGCTACGCCAGTGACGCTGGATGAAAAAGCATGGAAACGATACGCACTAATTTGCAGTTGG
CAAGGCTGGTCGGCGTGCAAGGAACGCCAGCGACGATCATTGGCGACGAGCTGATTCCGGGC
GCAGTGCCCTGGGATACGCTGGAAGCGGTGGTGAAAGAAAAACTGGCGTCTGCCAATGGCGG
GTA (SEQ ID NO: 4)
```

Figure 6 – cont 2 scsD nucleic acid sequence:

ATGGCGGGTAAACTGCGGCGTTGGCTGCGTGAAGCCGCGGTTTTTCTGGCGCTCCTCATCGC
GATAATGGTGGTCATGGACGTCTGGCGCGCGCCGCAGGCGCCTCCGGCGTTTGCCACGACAC
CATTACGTACGCTGACGGGAGAGTCGACAACTCTGGCGACATTGAGCGAAGAACGCCCCGTA
CTGCTCTATTTTTGGGCCAGCTGGTGCGGGGTATGCCGCTTTACTACGCCTGCGGTCGCTCG
CCTGGCGGCGGAAGGGGAAAACGTCATGACCGTTGCGCTCCGCTCCGGCGATGACGCTGAGG
TTGCCCGCTGGCTGGCGCGCAAGGGCGTTGACTTCCCGGTCGTCAATGATGCTAACGGCGCC
TTATCCGCTGGCTGGGAAATCAGCGTGACGCCAACGCTGGTGGTGGTTTCACAAGGTCGGGT
TGTGTTCACCACCAGCGGCTGGACCAGCTACTGGGGCATGAAGCTTCGGCTATGGTGGGCAA
AAACGTTCTGA (SEQ ID NO: 5)

cbpA amino acid sequence:

MELKDYYAIMGVKPTDDLKTIKTAYRRLARKYHPDVSKEPDAEARFKEVAEAWEVLSDEQRR
AEYDQLWQHRNDPQFNRQFQQHEGQPYNAEDFDDIFSSIFGQHGRHSHHRHAARGHDIEIEV
AVFLEETLEEHQRTISYSVPVYNAFGLVEREIPKTLNVKIPAGVSNGQRIRLKGQGTPGENG
GPNGDLWLVIHIAPHPLFDIVNQDLEVVLPLAPWEAALGAKVSVPTLKERILLTIPPGSQAG
QRLRIKGKGLASKKHTGDLYAIIKIVMPPKPDEKTAALWQQLADAQSSFDPRQQWGKA
(SEQ ID NO: 6)

scsA amino acid sequence:

MAKQQRMGWWFLCLACVVVMVCTAQRMAGLHALQMQATASAAVVSAPSSTDDGSPVTPCELS
AKSLLAAPPVLFEGAILALCLLLSLLAPVRVMRLPFSPPRAISPPTLRVHLRFCVFRE
(SEQ ID NO: 7)

Figure 6 – cont 3 scsB amino acid sequence:

MMILFRRILFCLLWLWLPVSWAAESGWLRSPDNDHASIRLRADTSANGETRLLLDVKLENGW
KTYWRAPGEGGVAPSIAWKGDMPEVSWFWPTPSRFDVANITTQGYHDEVTFPMIVRGTLPAT
LRGVLTLSTCSNVCLLTDYPFSVTPTVQNADFAHDYARAMGKIPLRSGLTDSLDVGYRPGEL
VVTATRAAGWSSPGLYLDTVDDVDFAKPRLRVEGDRLQATVPVTDSWGEKAPDLRNKSLTLV
LADGAIAQESTQTIGTAPAQTPDNAALPFWQVVMMALIGGLILNLMPCVLPVLGMKLGSILL
VEEKSRSHIRRQFLASVAGIIASFMALAAFMTLLRLSNHALAWGVQFQNVWFIGFMALVMLL
FSASLFGLFEFRLPSSMTTKLATYGGNGMSGHFWQGAFATLLATPCSAPFLGTAVAVALTAS
LPTLWGLFLALGLGMSAPWLLVAIRPGLALRLPRPGRWMNVLRRILGLMMLGSAIWLATLLL
PHFGFTASKSAQDTVQWQPLSEQAIQSALAQHKRVFVDVTADWCITCKVNKYNVLQKEDVQA
ALQQPDVVALRGDWTLPSDAITDFLKTRGQVAVPFNQVYGPGLPEGEALPTLLTRDAVLQTL
KKAKGITQ (SEQ ID NO: 8)

scsC amino acid sequence:

MKYMIVLLLALFSTLSIAQETAPFTPDQEKQIENLIHAALFNDPASPRIGAKHPKLTLVNFT
DYNCPYCKQLDPMLEKIVQKYPDVAVIIKPLPFKGESSVLAARIALTTWREHPQQFLALHEK
LMQKRVYHTDDSIKQAQQKAGATPVTLDEKSMETIRTNLQLARLVGVQGTPATIIGDELIPG
AVPWDTLEAVVKEKLASANGG (SEQ ID NO: 9)

scsD amino acid sequence:

MAGKLRRWLREAAVFLALLIAIMVVMDVWRAPQAPPAFATTPLRTLTGESTTLATLSEERPV
LLYFWASWCGVCRFTTPAVARLAAEGENVMTVALRSGDDAEVARWLARKGVDFPVVNDANGA
LSAGWEISVTPTLVVVSQGRVVFTTSGWTSYWGMKLRLWWAKTF (SEQ ID NO: 10)

SEQUENCE LISTING

<160> NUMBER OF SEQ ID NOS: 22

<210> SEQ ID NO 1
<211> LENGTH: 920
<212> TYPE: DNA
<213> ORGANISM: Salmonella Typhimurium

<400> SEQUENCE: 1

```
tatgctttcc cccattgctg gcgtgggtca aggacgact gcgcgtccgc cagttgttgc      60
cacagggcag ctgttttctc gtcaggtttc ggcggcataa cgattttgat gatggcatag    120
agatcgccag tgtgcttttt actggctaat ccttttcctt tgatacgcag ccgctgacct    180
gcctggctgc cgggggggaat ggtcagcaaa atacgctctt taagcgttgg cacagacacc    240
ttagcgccga gcgccgcctc ccatgggca agcggaagga cgacttccag atcctgattg      300
acgatatcaa agagcggatg cggggcaata tggataacga gccataaatc gccattaggt    360
ccgccgtttt cccccggcgt gccctggcct ttcagtctga ttcgttgccc gttgctgacg    420
ccagccggga tttttcacatt caatgtcttg ggaatttccc gctccaccag gccgaacgcg    480
ttataaacgg ggacggaata gctaatcgta cgctggtgct cttccagcgt ttcttccagg    540
aataccgcca cttcaatttc gatatcatga ccgcgtgcgg cgtggcggtg atgcgaatgg    600
```

```
cgaccgtgct gaccaaaaat agacgagaaa atatcatcaa aatcttcagc gttatacggc    660
tggccttcgt gttgctggaa ctggcgatta aattgtggat cgttacggtg ttgccataac    720
tggtcatact cggcgcgccg ttgctcatca ctcagcactt cccatgcttc agcaacctct    780
ttgaaacggg cttcggcatc gggttctttg ctgacatctg gatggtactt gcgggccagt    840
cggcgatagg cggtcttaat cgtcttgaga tcgtccgtcg gtttcacgcc cataatggcg    900
taataatcct taagttccat                                                920
```

<210> SEQ ID NO 2
<211> LENGTH: 363
<212> TYPE: DNA
<213> ORGANISM: Salmonella Typhimurium

<400> SEQUENCE: 2

```
atggcgaaac aacaacggat gggctggtgg tttctttgcc ttgcatgtgt cgtggtaatg     60
gtttgtaccg cgcaacgcat ggcgggcctg cacgccttgc agatgcaggc gacggcctct    120
gctgcggtgg tcagcgctcc ctcctcgaca gatgacggct cgccggtcac ccctgcgaa     180 ttaagcgcca gtcgctgct ggcggcgcct ccggtactct ttgaaggcgc tatccttgcg    240 cttgtctac tgcttttcctt actggcgcct gtccgggtca tgcgcctgcc gttttcgcct    300
ccacgggcta tttcgccgcc cacattacgg gtacatctac gattttgtgt cttccgtgaa    360
tga                                                                  363
```

<210> SEQ ID NO 3
<211> LENGTH: 1887
<212> TYPE: DNA
<213> ORGANISM: Salmonella Typhimurium

<400> SEQUENCE: 3

```
atgatgattt tgttcaggcg atactgttc tgcctgttat ggctttggct gcccgtctcc      60
tgggcggcgg aaagcggctg gctgcgttcg cccgataacg accatgccag catacggcta    120
cgtgccgata cgtccgctaa cggtgagacc cggctgttgc tggatgtcaa actggaaaac    180
ggctggaaaa cctactggcg cgcgccgggg aaggggcg tggcaccctc tatcgcctgg      240
aaaggcgaca tgcctgaggt aagctggttc tggccaaccc cctcgcgctt tgatgtggcg    300
aatatcacca cccagggata tcacgacgag gtgacctttc cgatgatcgt gcgcggtacg    360
ctgccggcga ccttgcgcgg tgtgttgacg ttatcaacct gcagcaatgt ttgtctgttg    420
accgattacc cctttccgt gacgcctact gtgcagaatg ccgattttgc ccatgactat    480
gcgcgggcga tgggtaaaat tccgctccgc agtggactaa cggactcgct tgacgtcggc    540
tatcgcccgg gagaactggt ggtcactgct acgcgagcgg cgggctggtc atcgcccggg    600
ctctatcttg acaccgtaga tgacgtcgat tttgcgaagc ctcgtctgcg cgtagagggc    660
gacaggttac aggcgacggt gccggtgacg gacagttggg gcgaaaaggc gcccgatttg    720
cgcaacaaat cgctgaccct cgtgttagcc gatggcgcta tcgcccagga gagcacgcaa    780
accattggca ctgcgccagc gcaaacgccg gacaatgcgg cgctaccttt ctggcaagtt    840
gtaatgatgg cgctgatcgg cggactgatt cttaatttaa tgccctgcgt actgccggtt    900
ctgggcatga agcttggctc tattttattg gtagaggaaa aaagccgctc tcacatcagg    960
cgacaatttt tggcttcggt cgccggtatc attgcgtcat ttatggcgct ggcggcgttt   1020
atgaccctcc ttcgcctgtc aaaccatgcg ctggcctggg gagtccagtt ccagaatgta   1080
```

```
tggtttattg gttttatggc gctggtgatg ttgttgttta gcgccagcct gttcgggctt    1140
tttgagttca ggcttccctc atctatgacc acgaaactgg ccacttacgg cggtaacggt    1200
atgtcgggac atttctggca gggggcattc gccacgctgc tggcgacgcc ttgtagcgcg    1260
ccgtttctgg gcacggcggt cgccgtggcg ctcacggcgt cgctgccgac gctgtggggg    1320
ctgttccttg cgcttggcct ggggatgagc gcgccgtggc tactggtcgc gatacgacca    1380
gggcttgcgc tacgtttacc gcgccccggg cgttggatga atgtcctgcg caggatcctc    1440
ggtctgatga tgctggggtc ggctatctgg ctggcgacgt tactcctgcc gcatttcggc    1500
ttcactgcgt caaagagcgc gcaagacacg gttcagtggc aaccgttgag tgaacaggca    1560
atccagtcgg cgctggcgca gcataagcgg gtatttgtcg atgtcactgc ggactggtgt    1620
attacctgta aagtgaataa atacaacgtc ctgcaaaaag aggatgtgca ggccgccttg    1680
caacagccgg atgttgtggc gctgcgggga gactggacgt tgccgtccga tgccattaca    1740
gattttctga aaacgcgcgg ccaggtcgcc gtgccgttta atcaggtata tggccccggc    1800
ttgccggaag gggaggcact gcccactttg ctgacccgcg atgcggtatt acaaacgttg    1860
aaaaaagcga aggaataac ccaatga                                         1887

<210> SEQ ID NO 4
<211> LENGTH: 623
<212> TYPE: DNA
<213> ORGANISM: Salmonella Typhimurium

<400> SEQUENCE: 4
atgaaataca tgattgtttt actgctggcg ctgttttcga cgctgagcat cgcgcaagaa     60
accgctcctt ttacgccgga tcaggaaaag cagattgaaa atctgatcca tgcggcgttg    120
tttaacgatc ctgccagccc gcggataggc gctaaacacc ctaagctgac gctggtgaac    180
tttacggatt acaactgccc gtactgcaaa cagctcgatc cgatgctgga aaagattgtg    240
cagaaatatc ctgacgttgc ggtcattatt aaaccgctgc catttaaagg agagagttcc    300
gttctggcgg cgcgtattgc gctgaccacc tggcgcgagc atccgcaaca gttcctcgcg    360
ctacatgaaa aactcatgca aaagcgcgtt taccatacgg atgacagtat taaacaggcc    420
cagcagaaag caggggctac gccagtgacg ctggatgaaa aaagcatgga aacgatacgc    480
actaatttgc agttggcaag gctggtcggc gtgcaaggaa cgccagcgac gatcattggc    540
gacgagctga ttccgggcgc agtgccctgg gatacgctgg aagcggtggt gaaagaaaaa    600
ctggcgtctg ccaatggcgg gta                                            623

<210> SEQ ID NO 5
<211> LENGTH: 507
<212> TYPE: DNA
<213> ORGANISM: Salmonella Typhimurium

<400> SEQUENCE: 5
atggcgggta aactgcggcg ttggctgcgt gaagccgcgg ttttctggc gctcctcatc      60 gcgataatgg tggtcatgga cgtctggcgc gcgccgcagg cgcctccggc gtttgccacg    120
acaccattac gtacgctgac gggagagtcg acaactctgg cgacattgag cgaagaacgc    180
cccgtactgc tctatttttg ggccagctgg tgcggggtat gccgctttac tacgcctgcg    240
gtcgctcgcc tggcggcgga aggggaaaac gtcatgaccg ttgcgctccg ctccggcgat    300
gacgctgagg ttgcccgctg gctggcgcgc aagggcgttg acttcccggt cgtcaatgat    360
gctaacggcg ccttatccgc tggctgggaa atcagcgtga cgccaacgct ggtggtggtt    420
```

```
tcacaaggtc gggttgtgtt caccaccagc ggctggacca gctactgggg catgaagctt    480
cggctatggt gggcaaaaac gttctga                                        507
```

<210> SEQ ID NO 6
<211> LENGTH: 306
<212> TYPE: PRT
<213> ORGANISM: Salmonella Typhimurium

<400> SEQUENCE: 6

```
Met Glu Leu Lys Asp Tyr Tyr Ala Ile Met Gly Val Lys Pro Thr Asp
1               5                   10                  15

Asp Leu Lys Thr Ile Lys Thr Ala Tyr Arg Arg Leu Ala Arg Lys Tyr
            20                  25                  30

His Pro Asp Val Ser Lys Glu Pro Asp Ala Glu Ala Arg Phe Lys Glu
        35                  40                  45

Val Ala Glu Ala Trp Glu Val Leu Ser Asp Glu Gln Arg Arg Ala Glu
    50                  55                  60

Tyr Asp Gln Leu Trp Gln His Arg Asn Asp Pro Gln Phe Asn Arg Gln
65                  70                  75                  80

Phe Gln Gln His Glu Gly Gln Pro Tyr Asn Ala Glu Asp Phe Asp Asp
                85                  90                  95

Ile Phe Ser Ser Ile Phe Gly Gln His Gly Arg His Ser His His Arg
            100                 105                 110

His Ala Ala Arg Gly His Asp Ile Glu Ile Glu Val Ala Val Phe Leu
        115                 120                 125

Glu Glu Thr Leu Glu Glu His Gln Arg Thr Ile Ser Tyr Ser Val Pro
    130                 135                 140

Val Tyr Asn Ala Phe Gly Leu Val Glu Arg Glu Ile Pro Lys Thr Leu
145                 150                 155                 160

Asn Val Lys Ile Pro Ala Gly Val Ser Asn Gly Gln Arg Ile Arg Leu
                165                 170                 175

Lys Gly Gln Gly Thr Pro Gly Glu Asn Gly Gly Pro Asn Gly Asp Leu
            180                 185                 190

Trp Leu Val Ile His Ile Ala Pro His Pro Leu Phe Asp Ile Val Asn
        195                 200                 205

Gln Asp Leu Glu Val Val Leu Pro Leu Ala Pro Trp Glu Ala Ala Leu
    210                 215                 220

Gly Ala Lys Val Ser Val Pro Thr Leu Lys Glu Arg Ile Leu Leu Thr
225                 230                 235                 240

Ile Pro Pro Gly Ser Gln Ala Gly Gln Arg Leu Arg Ile Lys Gly Lys
                245                 250                 255

Gly Leu Ala Ser Lys His Thr Gly Asp Leu Tyr Ala Ile Ile Lys
            260                 265                 270

Ile Val Met Pro Pro Lys Pro Asp Glu Lys Thr Ala Ala Leu Trp Gln
        275                 280                 285

Gln Leu Ala Asp Ala Gln Ser Ser Phe Asp Pro Arg Gln Gln Trp Gly
    290                 295                 300

Lys Ala
305
```

<210> SEQ ID NO 7
<211> LENGTH: 120
<212> TYPE: PRT
<213> ORGANISM: Salmonella Typhimurium

```
<400> SEQUENCE: 7

Met Ala Lys Gln Gln Arg Met Gly Trp Trp Phe Leu Cys Leu Ala Cys
1               5                   10                  15

Val Val Val Met Val Cys Thr Ala Gln Arg Met Ala Gly Leu His Ala
                20                  25                  30

Leu Gln Met Gln Ala Thr Ala Ser Ala Ala Val Val Ser Ala Pro Ser
            35                  40                  45

Ser Thr Asp Asp Gly Ser Pro Val Thr Pro Cys Glu Leu Ser Ala Lys
50                      55                  60

Ser Leu Leu Ala Ala Pro Pro Val Leu Phe Glu Gly Ala Ile Leu Ala
65                  70                  75                  80

Leu Cys Leu Leu Leu Ser Leu Ala Pro Val Arg Val Met Arg Leu
                85                  90                  95

Pro Phe Ser Pro Pro Arg Ala Ile Ser Pro Pro Thr Leu Arg Val His
            100                 105                 110

Leu Arg Phe Cys Val Phe Arg Glu
        115                 120

<210> SEQ ID NO 8
<211> LENGTH: 628
<212> TYPE: PRT
<213> ORGANISM: Salmonella Typhimurium

<400> SEQUENCE: 8

Met Met Ile Leu Phe Arg Arg Ile Leu Phe Cys Leu Leu Trp Leu Trp
1               5                   10                  15

Leu Pro Val Ser Trp Ala Ala Glu Ser Gly Trp Leu Arg Ser Pro Asp
                20                  25                  30

Asn Asp His Ala Ser Ile Arg Leu Arg Ala Asp Thr Ser Ala Asn Gly
            35                  40                  45

Glu Thr Arg Leu Leu Leu Asp Val Lys Leu Glu Asn Gly Trp Lys Thr
50                      55                  60

Tyr Trp Arg Ala Pro Gly Glu Gly Gly Val Ala Pro Ser Ile Ala Trp
65                  70                  75                  80

Lys Gly Asp Met Pro Glu Val Ser Trp Phe Trp Pro Thr Pro Ser Arg
                85                  90                  95

Phe Asp Val Ala Asn Ile Thr Thr Gln Gly Tyr His Asp Glu Val Thr
            100                 105                 110

Phe Pro Met Ile Val Arg Gly Thr Leu Pro Ala Thr Leu Arg Gly Val
        115                 120                 125

Leu Thr Leu Ser Thr Cys Ser Asn Val Cys Leu Leu Thr Asp Tyr Pro
130                     135                 140

Phe Ser Val Thr Pro Thr Val Gln Asn Ala Asp Phe Ala His Asp Tyr
145                 150                 155                 160

Ala Arg Ala Met Gly Lys Ile Pro Leu Arg Ser Gly Leu Thr Asp Ser
                165                 170                 175

Leu Asp Val Gly Tyr Arg Pro Gly Glu Leu Val Val Thr Ala Thr Arg
            180                 185                 190

Ala Ala Gly Trp Ser Ser Pro Gly Leu Tyr Leu Asp Thr Val Asp Asp
        195                 200                 205

Val Asp Phe Ala Lys Pro Arg Leu Arg Val Glu Gly Asp Arg Leu Gln
210                     215                 220

Ala Thr Val Pro Val Thr Asp Ser Trp Gly Glu Lys Ala Pro Asp Leu
225                 230                 235                 240
```

Arg Asn Lys Ser Leu Thr Leu Val Leu Ala Asp Gly Ala Ile Ala Gln
            245                 250                 255

Glu Ser Thr Gln Thr Ile Gly Thr Ala Pro Ala Gln Thr Pro Asp Asn
        260                 265                 270

Ala Ala Leu Pro Phe Trp Gln Val Val Met Met Ala Leu Ile Gly Gly
        275                 280                 285

Leu Ile Leu Asn Leu Met Pro Cys Val Leu Pro Val Leu Gly Met Lys
    290                 295                 300

Leu Gly Ser Ile Leu Leu Val Glu Glu Lys Ser Arg Ser His Ile Arg
305                 310                 315                 320

Arg Gln Phe Leu Ala Ser Val Ala Gly Ile Ile Ala Ser Phe Met Ala
                325                 330                 335

Leu Ala Ala Phe Met Thr Leu Leu Arg Leu Ser Asn His Ala Leu Ala
                340                 345                 350

Trp Gly Val Gln Phe Gln Asn Val Trp Phe Ile Gly Phe Met Ala Leu
            355                 360                 365

Val Met Leu Leu Phe Ser Ala Ser Leu Phe Gly Leu Phe Glu Phe Arg
    370                 375                 380

Leu Pro Ser Ser Met Thr Thr Lys Leu Ala Thr Tyr Gly Gly Asn Gly
385                 390                 395                 400

Met Ser Gly His Phe Trp Gln Gly Ala Phe Ala Thr Leu Leu Ala Thr
                405                 410                 415

Pro Cys Ser Ala Pro Phe Leu Gly Thr Ala Val Ala Val Ala Leu Thr
                420                 425                 430

Ala Ser Leu Pro Thr Leu Trp Gly Leu Phe Leu Ala Leu Gly Leu Gly
            435                 440                 445

Met Ser Ala Pro Trp Leu Leu Val Ala Ile Arg Pro Gly Leu Ala Leu
450                 455                 460

Arg Leu Pro Arg Pro Gly Arg Trp Met Asn Val Leu Arg Arg Ile Leu
465                 470                 475                 480

Gly Leu Met Met Leu Gly Ser Ala Ile Trp Leu Ala Thr Leu Leu Leu
                485                 490                 495

Pro His Phe Gly Phe Thr Ala Ser Lys Ser Ala Gln Asp Thr Val Gln
                500                 505                 510

Trp Gln Pro Leu Ser Glu Gln Ala Ile Gln Ser Ala Leu Ala Gln His
            515                 520                 525

Lys Arg Val Phe Val Asp Val Thr Ala Asp Trp Cys Ile Thr Cys Lys
530                 535                 540

Val Asn Lys Tyr Asn Val Leu Gln Lys Glu Asp Val Gln Ala Ala Leu
545                 550                 555                 560

Gln Gln Pro Asp Val Val Ala Leu Arg Gly Asp Trp Thr Leu Pro Ser
                565                 570                 575

Asp Ala Ile Thr Asp Phe Leu Lys Thr Arg Gly Gln Val Ala Val Pro
                580                 585                 590

Phe Asn Gln Val Tyr Gly Pro Gly Leu Pro Glu Gly Glu Ala Leu Pro
            595                 600                 605

Thr Leu Leu Thr Arg Asp Ala Val Leu Gln Thr Leu Lys Lys Ala Lys
610                 615                 620

Gly Ile Thr Gln
625

<210> SEQ ID NO 9
<211> LENGTH: 207
<212> TYPE: PRT

<213> ORGANISM: Salmonella Typhimurium

<400> SEQUENCE: 9

```
Met Lys Tyr Met Ile Val Leu Leu Leu Ala Leu Phe Ser Thr Leu Ser
1               5                   10                  15

Ile Ala Gln Glu Thr Ala Pro Phe Thr Pro Asp Gln Glu Lys Gln Ile
            20                  25                  30

Glu Asn Leu Ile His Ala Ala Leu Phe Asn Asp Pro Ala Ser Pro Arg
        35                  40                  45

Ile Gly Ala Lys His Pro Lys Leu Thr Leu Val Asn Phe Thr Asp Tyr
50                  55                  60

Asn Cys Pro Tyr Cys Lys Gln Leu Asp Pro Met Leu Glu Lys Ile Val
65                  70                  75                  80

Gln Lys Tyr Pro Asp Val Ala Val Ile Ile Lys Pro Leu Pro Phe Lys
                85                  90                  95

Gly Glu Ser Ser Val Leu Ala Ala Arg Ile Ala Leu Thr Thr Trp Arg
            100                 105                 110

Glu His Pro Gln Gln Phe Leu Ala Leu His Glu Lys Leu Met Gln Lys
        115                 120                 125

Arg Val Tyr His Thr Asp Asp Ser Ile Lys Ala Gln Gln Lys Ala
    130                 135                 140

Gly Ala Thr Pro Val Thr Leu Asp Glu Lys Ser Met Glu Thr Ile Arg
145                 150                 155                 160

Thr Asn Leu Gln Leu Ala Arg Leu Val Gly Val Gln Gly Thr Pro Ala
                165                 170                 175

Thr Ile Ile Gly Asp Glu Leu Ile Pro Gly Ala Val Pro Trp Asp Thr
            180                 185                 190

Leu Glu Ala Val Val Lys Glu Lys Leu Ala Ser Ala Asn Gly Gly
        195                 200                 205
```

<210> SEQ ID NO 10
<211> LENGTH: 168
<212> TYPE: PRT
<213> ORGANISM: Salmonella Typhimurium

<400> SEQUENCE: 10

```
Met Ala Gly Lys Leu Arg Arg Trp Leu Arg Glu Ala Ala Val Phe Leu
1               5                   10                  15

Ala Leu Leu Ile Ala Ile Met Val Val Met Asp Val Trp Arg Ala Pro
            20                  25                  30

Gln Ala Pro Pro Ala Phe Ala Thr Pro Leu Arg Thr Leu Thr Gly
        35                  40                  45

Glu Ser Thr Thr Leu Ala Thr Leu Ser Glu Glu Arg Pro Val Leu Leu
50                  55                  60

Tyr Phe Trp Ala Ser Trp Cys Gly Val Cys Arg Phe Thr Thr Pro Ala
65                  70                  75                  80

Val Ala Arg Leu Ala Ala Glu Gly Glu Asn Val Met Thr Val Ala Leu
                85                  90                  95

Arg Ser Gly Asp Asp Ala Glu Val Ala Arg Trp Leu Ala Arg Lys Gly
            100                 105                 110

Val Asp Phe Pro Val Val Asn Asp Ala Asn Gly Ala Leu Ser Ala Gly
        115                 120                 125

Trp Glu Ile Ser Val Thr Pro Thr Leu Val Val Ser Gln Gly Arg
    130                 135                 140

Val Val Phe Thr Thr Ser Gly Trp Thr Ser Tyr Trp Gly Met Lys Leu
```

145         150         155         160

Arg Leu Trp Trp Ala Lys Thr Phe
                165

<210> SEQ ID NO 11
<211> LENGTH: 71
<212> TYPE: DNA
<213> ORGANISM: Artificial sequence
<220> FEATURE:
<223> OTHER INFORMATION: Primer

<400> SEQUENCE: 11 gaaaccttttt ggggtccctt ctgtatgtat tgatttagcg agatgatgct tgtgtaggct        60
ggagctgctt c                                                              71

<210> SEQ ID NO 12
<211> LENGTH: 70
<212> TYPE: DNA
<213> ORGANISM: Artificial sequence
<220> FEATURE:
<223> OTHER INFORMATION: Primer

<400> SEQUENCE: 12
gtgtgcaaac aaaattcggt gatggtaaag gtgacagtga tgttagccat catatgaata        60
tcctccttag                                                                70

<210> SEQ ID NO 13
<211> LENGTH: 71
<212> TYPE: DNA
<213> ORGANISM: Artificial sequence
<220> FEATURE:
<223> OTHER INFORMATION: Primer

<400> SEQUENCE: 13
caaaaccgcg ccagtggcta agataactcg cgttaaacag tgagggcgca tgtgtaggct        60
ggagctgctt c                                                              71

<210> SEQ ID NO 14
<211> LENGTH: 68
<212> TYPE: DNA
<213> ORGANISM: Artificial sequence
<220> FEATURE:
<223> OTHER INFORMATION: Primer

<400> SEQUENCE: 14 atttttctc cgtgaatgag taattaaccg ttagcaataa ccggtctgca tatgaatatc        60
ctccttag                                                                  68

<210> SEQ ID NO 15
<211> LENGTH: 64
<212> TYPE: DNA
<213> ORGANISM: Artificial sequence
<220> FEATURE:
<223> OTHER INFORMATION: Primer

<400> SEQUENCE: 15
cggttattgc taacggttaa ttactcattc acggagaaaa aattgtgtag gctggagctg        60
cttc                                                                      64

<210> SEQ ID NO 16
<211> LENGTH: 70
<212> TYPE: DNA

```
<213> ORGANISM: Artificial sequence
<220> FEATURE:
<223> OTHER INFORMATION: Primer

<400> SEQUENCE: 16
cgcgatgctc agcgtcgaaa acagcgccag cagtaaaaca atcatgtatt catatgaata    60
tcctccttag                                                          70

<210> SEQ ID NO 17
<211> LENGTH: 71
<212> TYPE: DNA
<213> ORGANISM: Artificial sequence
<220> FEATURE:
<223> OTHER INFORMATION: Primer

<400> SEQUENCE: 17
gcgatgcggt attacaaacg ttgaaaaaag cgaaaggaat aacccaatga tgtgtaggct    60
ggagctgctt c                                                        71

<210> SEQ ID NO 18
<211> LENGTH: 56
<212> TYPE: DNA
<213> ORGANISM: Artificial sequence
<220> FEATURE:
<223> OTHER INFORMATION: Primer

<400> SEQUENCE: 18
gcttcacgca gccaacgccg cagtttaccc gccattcata tgaatatcct ccttag        56

<210> SEQ ID NO 19
<211> LENGTH: 71
<212> TYPE: DNA
<213> ORGANISM: Artificial sequence
<220> FEATURE:
<223> OTHER INFORMATION: Primer

<400> SEQUENCE: 19
gccctgggat acgctggaag cggtggtgaa agaaaaactg gcgtctgcca tgtgtaggct    60
ggagctgctt c                                                        71

<210> SEQ ID NO 20
<211> LENGTH: 70
<212> TYPE: DNA
<213> ORGANISM: Artificial sequence
<220> FEATURE:
<223> OTHER INFORMATION: Primer

<400> SEQUENCE: 20
gatttcgcaa aacgggggtt tttcttacag taaacgcgtt agcgccggga catatgaata    60
tcctccttag                                                          70

<210> SEQ ID NO 21
<211> LENGTH: 71
<212> TYPE: DNA
<213> ORGANISM: Artificial sequence
<220> FEATURE:
<223> OTHER INFORMATION: Primer

<400> SEQUENCE: 21
caaaaccgcg ccagtggcta agataactcg cgttaaacag tgagggcgca tgtgtaggct    60
ggagctgctt c                                                        71
```

```
<210> SEQ ID NO 22
<211> LENGTH: 70
<212> TYPE: DNA
<213> ORGANISM: Artificial sequence
<220> FEATURE:
<223> OTHER INFORMATION: Primer

<400> SEQUENCE: 22
gatttcgcaa aacgggggtt tttcttacag taaacgcgtt agcgccggga catatgaata      60
tcctccttag                                                            70
```

PREVENTION OF *SALMONELLA* RECRUDESCENSE

FIELD OF THE INVENTION

The present invention relates to novel *Salmonella* mutants, to a process for producing the same and to vaccines containing the same, wherein said *Salmonella* mutants are characterized in that they are not responsive to recrudescence.

It is accordingly an object of the present invention to provide the use of said *Salmonella* mutants in the vaccination of animals, in particular mammals and birds, more in particular pigs, poultry and cattle.

BACKGROUND TO THE INVENTION

Salmonellae are Gram-negative, facultative anaerobic, motile, non-lactose is fermenting rods belonging to the family Enterobacteriaceae. Salmonellae are usually transmitted to humans by the consumption of contaminated foods and cause salmonellosis.

Salmonellae have been isolated from many animal species including, birds, cattle, sheep, pigs, dogs, cats, horses, donkeys, seals and reptiles. Ninety-five percent or more of the *Salmonella* serovars (ser.) isolated from food producing animals belong to *Salmonella enterica* subspecies *enterica* (*S. enterica*), with *Salmonella* ser. Typhimurium (*S. Typhimurium*), *Salmonella* ser. Choleraesuis (S. Choleraesuis), *Salmonella* ser. Derby (S. Derby), *Salmonella* ser. Infantis (*S. Infantis*), *Salmonella* ser. Bredeney (S. Bredeney), *Salmonella* ser. Rissen (S. Rissen), and *Salmonella* ser. Anatum (S. Anatum), as the most common serovars in pigs. *Salmonella* Enteritidis (*S. Enteritidis*), *S. Typhimurium*, *Salmonella* Hadar (S. Hadar), *Salmonella* Virchow (S. Virchow), *S. infantis*, *Salmonella* Kentucky (S. Kentucky), S. Bredeney, *Salmonella* Agona (S. Agona) and *Salmonella* paratyphi B (S. paratyphi B) are the most common in poultry.

*Salmonella* infections are a serious medical and veterinary problem world-wide and cause concern in the food industry. Control of salmonellosis is important to avoid potentially lethal human infections and considerable economic losses for the social security and animal husbandry industry.

There has been a long history of the use of live attenuated *Salmonella* vaccines as effective vaccines for the prevention of salmonellosis in animals and humans. The live attenuated oral typhoid vaccine, Ty21a (Vivotif®), manufactured by the Swiss Serum Vaccine Institute, has proved to be a successful vaccine for the prevention of typhoid fever and has been licensed in many countries including the US and Europe. However, none of the currently available vaccines confer any protection against recrudescence of infection e.g. triggered by stress (Nakamura et al., 1994; Wallis, 2001; Boyen et al., 2008).

Fasting and transportation of animals is known to cause varying levels of stress, depending on a number of parameters, such as crowding, temperature, social status, and duration of feed deprival/transport. A period of stress results in the release of a variety of neurotransmitters, peptides, cytokines, hormones, and other factors into the circulation or tissues of the stressed organism (Freestone et al., 2008). Besides the fast-acting catecholamines, which are released by the sympathetic nervous system, the hypothalamic-pituitary-adrenal axis becomes activated which results in the release of the slow-acting glucocorticoids by the adrenal gland (Dhabhar F S, 2009). These stress hormones can affect the host immune response via the modulation of various aspects of the immune system. However, the pathogenesis of an infection can also be altered by direct effects of these stress mediators on the bacteria. Bacteria can exploit the neuroendocrine alteration of a host stress reaction as a signal for growth and pathogenic processes (Freestone et al., 2008; Lyte M, 2004). This could partly explain the stress induced recrudescence of *Salmonella* Typhimurium by pigs (Boyen et al., 2009b).

Pigs secrete cortisol as the predominant glucocorticoid (Worsaae and Schmidt, 1980). Peak levels of cortisol occur immediately after start of transport and remain elevated throughout transport (Bradshaw et al., 1996), and plasma cortisol concentrations are an important measure of stress (Jensen-Waern and Nyberg, 1993).

Stress can increase *Salmonella* shedding in infected pigs and even cause a recrudescence of *Salmonella* in carriers (Hurd et al., 2002). Consequently, periods of stress result in increased cross-contamination during transport and lairage and to a higher degree of carcass contamination which could lead to higher numbers of foodborne *Salmonella* infections in humans (Berends et al., 1996; Wong et al., 2002). Reduction of *Salmonella* in animal products should thus include monitoring and intervention not only at the farm level, but at all levels of production.

For said reasons, it is desirable to develop a vaccine or vaccine strain that is induces a good immune response, is not responsive to recrudescence and/or that is able to prevent or reduce *Salmonella* recrudescence in order to keep the *Salmonella* bacteria and the number of *Salmonella* contaminated animals from increasing during periods of stress.

SUMMARY OF THE INVENTION

The present invention is based on the finding that the increased intracellular survival in macrophages under cortisol-induced stress is associated with an upregulation of the genes scsA, scsB, scsC, scsD and/or cbpA of the *Salmonella* bacteria. These genes are therefore suitable targets in the manufacture of a vaccine to prevent or reduce *Salmonella* recrudescence in a subject.

It is accordingly a first objective of the present invention to provide a *Salmonella* mutant strain, having at least one genetic modification within, in particular a deletion of, the scsABCD (or scs) locus or the scsA, scsB, scsC, scsD and/or cbpA gene, more in particular within the scsA gene or the scsABCD locus. As will be apparent to the skilled artisan, said genetic modification includes both a naturally occurring genetic modification within said gene(s), as well as an artificially introduced genetic modification. Preferably the genetic modification is an artificially introduced genetic modification.

With the objective to obtain *Salmonella* mutant strains, the scs locus, scsA, scsB, scsC, scsD and/or cbpA gene mutations as defined herein, can be applied in wild type *Salmonella* serovars, including naturally occurring attenuated *Salmonella* vaccine strains, as well as in artificially attenuated *Salmonella* vaccine strains. The latter typically comprise one, two, three or more (auxotrophic) mutations. In a particular embodiment the present invention provides the *Salmonella* mutant strain, having at least one genetic modification within the scs locus or the scsA, scsB, scsC, scsD and/or cbpA genes, in particular the scs locus or the scsA gene, and further comprising one, two, three or more (auxotrophic) mutations.

The *Salmonella* mutant strain as defined and used herein, includes *Salmonella enterica* and any serotype of the *enterica* subspecies, and is typically selected from the group consisting of *S. Typhimurium*, S. Choleraesuis, S. Derby, *S. Infantis*,

*S. Bredeney, S. Rissen, S. Anatum, S. Hadar, S. Virchow,* and *S. Enteritidis*. In a more particular embodiment said strain is *Salmonella* ser. *Typhimurium*.

A further embodiment includes the *Salmonella* mutant strain for use as a vector to administer a heterologous antigen to a subject for vaccination against an infectious agent.

It is a further objective of the present invention to provide the use of a *Salmonella* mutant strain as described herein, in the manufacture of a vaccine.

In a further embodiment the present invention provides a composition, in particular a vaccine, comprising the *Salmonella* strain of the invention, optionally comprising a pharmaceutically acceptable carrier, diluent and/or adjuvant.

A further embodiment provides the *Salmonella* mutant strain, or the composition of the present invention for use as a medicament. More particular the invention provides the *Salmonella* mutant strain e.g. as part of a vaccine for use in the prevention or inhibition of recrudescence of said strain in a subject, more specific an animal.

Another embodiment provides the use of the composition of the present invention in the treatment or prevention of *Salmonella* infection, in particular for immunization of pigs, poultry, and/or cattle, and against recrudescence of *Salmonella* infection.

It is also an object of the present invention to provide a method for treating or preventing *Salmonella* recrudescence, comprising administering a *Salmonella* mutant strain or a composition of the present invention, to a subject.

BRIEF DESCRIPTION OF THE DRAWINGS

FIG. 6: Nucleic acid and amino acid sequences of or encoded by the *Salmonella* scsA, scsB, scsC, scsD and/or cbpA genes.

DESCRIPTION OF THE INVENTION

Figure 1:
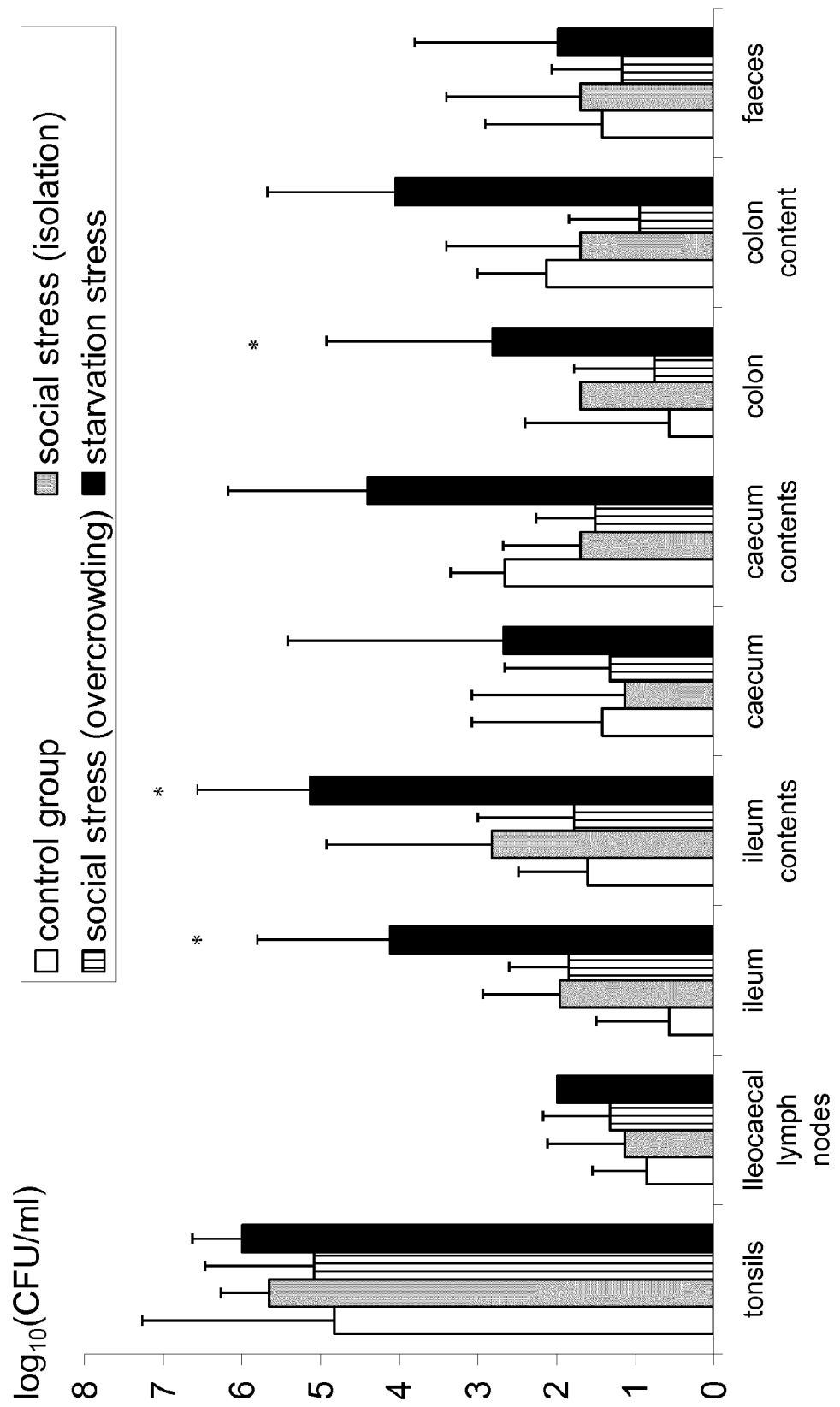
FIG. 1: Recovery of *Salmonella Typhimurium* bacteria from various organs and gut contents of carrier pigs that were submitted to either feed withdrawal (n=6) or social stress, isolation (n=3) and overcrowding (n=9), 24 hours before euthanasia. Six pigs were not stressed and served as a control group. The $\log_{10}$ value of the ratio of CFU per gram sample is given as the mean+standard deviation. Superscript (*) refers to a significant difference compared to the control group (p≤0.05).

The present invention provides mutant strains of *Salmonella*, in particular *Salmonella enterica*, that are useful as live or attenuated vaccines for inducing immunological protection against *Salmonella*, and characterized in that they prevent or reduce intracellular proliferation in macrophages of the *Salmonella* bacteria triggered by specific circumstances. The mutant strains of the present invention are characterized in that they contain at least one genetic modification within the scsA, scsB, scsC, scsD and/or cbpA gene. The present invention thus relates to a *Salmonella* strain in which at least one genetic modification within the scsA, scsB, scsC, scsD and/or cbpA gene was introduced.

*Salmonella Typhimurium* is able to penetrate the mucosal barrier, interact with cells of the immune system and reside in these cells as an intracellular pathogen (Finlay B & Brumell, 2000). Stress induced recrudescence is associated with increased proliferation of the bacterium inside the macrophage. It has now been demonstrated that *Salmonella* strains comprising a genetic modification in at least one of the scsA, scsB, scsC, scsD and cbpA genes, and in particular in the scs locus or in the scsA gene, yield mutants that no longer exhibit increased proliferation in macrophages in response to stress factors, characterized by elevated cortisol levels. As such the *Salmonella* mutant strains of the present invention are particularly useful in preparing a vaccine strain that is not responsive to stress-related is recrudescence in a subject. As used herein, the term "recrudescence" refers to reappearance of an infection after it has been quiescent i.e. after a period of latency or relative inactivity; i.e. a new outbreak or the return (become active again) of an infection. “*Salmonella* recrudescence” or “recrudescence of a *Salmonella* infection” is characterized by re-excretion of the *Salmonella* vaccine strain or the *Salmonella* infection strain by the subject. This results in an increased risk of carrier subjects to begin shedding again, persistent shedders to excrete *Salmonella* at higher number, and *Salmonella*-free subjects of becoming infected. In a specific embodiment the recrudescence is stress induced recrudescence. “Stress” or “stress factors” include but are not limited to feed withdrawal, social stress, crowding, temperature changes, social status, rehousing, transport and starvation before slaughter, and is characterized by an increased cortisol blood level.

A “subject” as used herein includes a human or animal, in particular birds (poultry; chicken, turkey, etc.), pigs, or cattle.

In a particular embodiment, the *Salmonella* mutant strains of the present invention are used as attenuated live vaccines. It is well established that live attenuated micro-organisms are highly effective vaccines; immune responses elicited by such vaccines are often of greater magnitude and of longer duration than those produced by non-replicating immunogens. One explanation for this may be that live attenuated strains establish limited infections in the host and mimic the early stages of natural infection. In addition, unlike killed preparations, live vaccines are often more potent in inducing mucosal immune responses and cell-mediated responses, which may be connected with their ability to replicate in epithelial cells and antigen-presenting cells, such as macrophages, respectively. However, concerns remain over the safety of using live-attenuated vaccines. There may also be a risk of the attenuated strain reverting to virulence, thus having the potential to cause disease and abortion in the vaccinated animal. Surprisingly, it has been demonstrated by the present invention that the vaccine strains and methods as described herein is overcome the risk of stress induced recrudescence of the *Salmonella* vaccine strain in a vaccinated subject, thereby significantly improving the safety of live vaccines.

The “genetic modification” may be an insertion, a deletion, and/or a substitution of one or more nucleotides in said genes. Deletion mutants (of the complete gene or part thereof) are preferred. The genetic modifications or mutations may be introduced into the microorganism using any known technique. Preferably, the mutation is a deletion mutation, where disruption of the gene is caused by the excision of nucleic acids. Alternatively, mutations may be introduced by the insertion of nucleic acids or by point mutations. Methods for introducing the mutations into the specific regions will be apparent to the skilled person and are preferably created using the one step inactivation method described by Wanner and Datsenko (2000). Other methods can be applied to achieve a site directed mutagenesis (eg. using suicide plasmids), however the one-step inactivation method is generally accepted as the best and fastest way to achieve a knock-out deletion mutant.

The *Salmonella* mutant strain of the present invention can optionally further comprise one or more additional mutations. Suitable genes for said mutations include but are not limited to genes such as aroA, purA, dam, his, cya/crp, htrA, Lon, phoP/phoQ, guaBA, nuoG, rpoS, rpoE, surA, thyA, aceA and the like. Other genes that may be affected to improve the safety of the vaccine include virulence factors, such as for example SPI-1, SPI-2, SPI-3, SPI-4, SPI-5 and/or related effectors, flagellum-associated genes, fimbria-associated genes, LPS-associted genes and adhesines; quorum sensing and/or biofilm associated genes; genes involved in outer membrane proteins; and regulators of anyone of the aforementioned genes.

Although any serotype of *S. enterica* may be used, in preferred embodiments, the modifications are inserted into *S. enterica* serovars, such as for example *Salmonella* ser. *Typhimurium* (*S. Typhimurium*), *Salmonella* ser. Choleraesuis (S. Choleraesuis), *Salmonella* ser. Derby (S. Derby), *Salmonella* ser. *Infantis* (*S. Infantis*), *Salmonella* ser. Bredeney (S. Bredeney), *Salmonella* ser. Rissen (S. Rissen), and *Salmonella* ser. Anatum (S. Anatum). In a particular embodiment said modification(s) are inserted a *Salmonella* ser. *Typhimurium* background.

The scs locus (scsABCD) consists of two operons, one operon consisting of the single scsA gene and another operon (scsBCD) containing the scsB, scsC and scsD genes encoding proteins that may mediate copper tolerance indirectly by catalyzing the correct folding of periplasmic copper-binding target proteins via a disulfide isomerise-like activity (Gupta et al., 1997). It is demonstrated in the present invention that scsA and scsABCD are vital for dexamethasone induced recrudescence of *Salmonella* in a DBA/2J mice model, without increasing the virulence of the *Salmonella Typhimurium* strain used. Deletion of scsA or the entire scs locus in *Salmonella Typhimurium* live vaccines reduces stress related recrudescence of live vaccine strains.

Preferably, the mutants of the present invention contain at least one genetic modification within the scsA gene, or within the complete scs locus (scsABCD). As used herein, the scsA, scsB, scsC, scsD or cbpA gene is meant to include any homolog or artificial sequence that is substantially identical, i.e. at least 70%, 75%, 80%, 85%, 87%, 89%, 90%, 91%, 92%, 93%, 94%, 95%, 96%, 97%, 98%, 99%, and preferably 100% identical to the corresponding scs locus, scsA, scsB, scsC, scsD or cbpA gene as found in *Salmonella enterica* subsp. *enterica* serovar *Typhimurium* str. LT2 chromosome with NCBI reference sequence NC_003197.1 GI:16763390, and as provided in FIG. 6 (SEQ ID NO 1-5). In said reference sequence the scsA gene corresponds to CDS 1200154.1200516 having GeneID 1252631 and encoding the "suppressor for copper-sensitivity protein A" (NP_460086.1). The scsB gene corresponds to CDS 1200565.1202451 having GeneID 1252632 and encoding the protein "suppressor for copper-sensitivity B" (NP_460087.1). The scsC gene corresponds to CDS 1202448.120307 having GeneID 1252633 and encoding the protein "suppressor for copper-sensitivity C" (NP_460088.1). The scsD gene corresponds to CDS 1203061.1203567, is having GeneID 1252634 and encoding the protein "suppressor for copper-sensitivity D" (NP_460089.1). The cbpA gene is characterized by GeneID 1252630 and encodes the protein "curved DNA-binding protein CbpA" (NP_460085.1). In a specific embodiment, the present invention encompasses a *Salmonella* mutant strain comprising a genetic modification in, and in particular a deletion of, the scsA gene or the scsABCD locus, as compared to the corresponding wild type sequence as found in *Salmonella enterica* subsp. *enterica* serovar *Typhimurium* str. LT2 chromosome with NCBI reference sequence NC_003197.1 GI:16763390.

The percentage identity of nucleic acid and polypeptide sequences can be calculated using commercially available algorithms which compare a reference sequence with a query sequence. The following programs (provided by the National Center for Biotechnology Information) may be used to determine homologies/identities: BLAST, gapped BLAST, BLASTN and PSI BLAST, which may be used with default parameters.

As already mentioned, safety of (existing) attenuated vaccine strains can be highly improved by applying the methods of the present invention. It is thus also an object of the invention to convert *Salmonella* vaccine strains, including naturally occurring attenuated *Salmonella enterica* vaccine strains, as well as artificially attenuated *Salmonella enterica* vaccine strains, into mutant strains by introducing one or more genetic modifications in the scsA gene, or in the complete scs locus, into said (existing) vaccine strains.

Hence, a particular embodiment of the present invention relates to a method to convert a *Salmonella* vaccine strain into a safer vaccine strain, said method comprising the following steps:
  obtaining a *Salmonella enterica* (vaccine) strain, and
  substituting or deleting part or all of the scsA gene, or the scs locus, in particular deleting the complete scsA gene or the scs locus.

The method optionally further comprises one or more of the following steps:
  creating a PCR adjusted antibiotic resistance cassette,
  inserting a helper plasmid in the *Salmonella enterica* (vaccine) strain,
  substituting part or all of the scsA gene, or the scs locus, with the PCR adjusted antibiotic resistance cassette,
  controlling the substitution with PCR and sequencing,
  inserting the helper plasmid in the substituted target strain,
  deleting the antibiotic resistance cassette and the helper plasmids, and
  controlling the deletion with PCR and sequencing.

More specific, construction of deletion mutants in genes according to the one-step inactivation method is e.g. described by Datsenko and Wanner (2000) optionally with some modifications (Donné et al., 2005).

In said embodiment wherein a *Salmonella enterica* vaccine strain is converted into a mutant strain as provided herein, the vaccine strain according to the invention can optionally include additional mutations (also referred to as auxotrophic mutations). Suitable genes for the auxotrophic mutation include but are not limited to genes such as aroA, purA, dam, his, cya/crp, htrA, Lon, phoP/phoQ, guaBA, nuoG, rpoS, rpoE, surA, thyA, aceA and the like. Other genes that may be affected to improve the safety of the vaccine include virulence factors, such as for example SPI-1, SPI-2, SPI-3, SPI-4, SPI-5 and/or related effectors, flagellum-associated genes, fimbria-associated genes, LPS-associted genes and adhesines; quorum sensing and/or biofilm associated genes; genes involved in outer membrane proteins; and regulators of anyone of the aforementioned genes. When modifying existing vaccines according to the method of the current invention, it is important that the further modification does not affect the already weakened strain in its immunogenic and protective effect.

In a further embodiment, the *Salmonella* mutant is very suitable as a delivery vector. Any of the *Salmonella* mutant strains described herein can be used as a vector to administer an antigen, DNA or RNA, to a subject for vaccination against an infectious agent, e.g. bacteria, viruses or parasites. Antigen delivery is can be accomplished by introducing into the *Salmonella* mutant strain a heterologous nucleic molecule encoding the antigen. The antigen-encoding nucleic acid molecule to be introduced into the attenuated *Salmonella* strain can be present, for example, in a plasmid vector that includes a regulatory sequence, such as a promoter, and, optionally, a sequence encoding a secretion signal.

The promoter can be a prokaryotic promoter, for example, a *Salmonella* promoter, which directs expression of the antigen in the *Salmonella* vector. Examples of such promoters are well known to the person skilled in the art. Alternatively, the promoter can be an eukaryotic promoter. Use of such promoters allows for expression of target antigen in a eukaryotic cell, with *Salmonella* acting as the delivery vehicle for this DNA immunization approach. The construction of such vectors is known in the art. Of course, numerous eukaryotic promoters are known in the art and can be used. Introduction of a plasmid into the *Salmonella* mutant strain can be accomplished using any of a number of standard methods, such as electroporation or bacteriophage transduction (e.g. Ausubel et al., *Current Protocols in Molecular Biology*, John Wiley & Sons Inc., 1994).

In a further embodiment, the mutant *Salmonella* strains are used to manufacture a (pharmaceutical) composition or a vaccine composition, which may be administered to the subject via the parenteral, mucosal or oral route. Inactivated or live vaccines can be produced using art known procedures and typically include a pharmaceutically acceptable carrier or diluent, and optionally an adjuvant.

It is accordingly an object of the present invention to provide a pharmaceutical composition or a vaccine against *Salmonella* recrudescence comprising:
  a mutant strain according to the invention; and
  a pharmaceutically acceptable carrier or diluent.

The particular pharmaceutically acceptable carriers or diluents employed are not critical to the present invention, and are conventional in the art. Examples is of diluents include: buffer for buffering against gastric acid in the stomach, such as citrate buffer (pH 7.0) containing sucrose, bicarbonate buffer (pH 7.0) alone, or bicarbonate buffer (pH 7.0)

containing ascorbic acid, lactose, and optionally aspartame. Examples of carriers include: proteins, e.g., as found in skimmed milk; sugars, e.g. sucrose; or polyvinylpyrrolidone.

The particular adjuvants employed are not critical to the present invention, and are conventional in the art. Examples of adjuvants include, but are not limited to, tensoactive compounds (such as Quil A), mineral salts (such as aluminium hydroxide), micro-organism derived adjuvants (such as muramyl dipeptide), oil-in-water and water-in-oil emulsions (such as Freund's incomplete adjuvant), particulate antigen delivery systems (such as liposomes, polymeric atmospheres, nanobeads, ISCOMs and ISCOMATRIX), polysaccharides (such as micro-particulate inulin), nucleic acid based adjuvants (such as CpG motivs), cytokines (such as interleukins and interferons), activators of Toll-like receptors and eurocine L3 en N3 adjuvantia.

As is known to the skilled artisan, the dose or amount varies according to the route of administration. Those skilled in the art may find that the effective dose for a vaccine administered parenterally may be smaller than a similar vaccine which is administered via drinking water, and the like. The number of microorganisms that are required to be present in the formulations can be determined and optimised by the skilled person. However, in general, a patient may be administered approximately $10^7$-$10^{10}$ colony-forming units (CFUs), preferably approximately $10^4$-$10^9$ CFUs in a single dosage unit.

The composition or vaccine comprising are highly suitable for protecting animals against *Salmonella* recrudescence. The mutant *Salmonella* strains of the invention, and composition or vaccine comprising the same, are highly suitable for immunizing veterinary species, in particular pigs, cattle and poultry, and even more in particular pigs.

It is thus an object of the present invention to provide the use of mutant strains is of *Salmonella enterica* of the present invention for preparing a medicament which is employed for the prophylactic and/or therapeutic treatment of *Salmonella* infection in animals, in particular in pigs. The present invention thus also encompasses the mutant strains of *Salmonella enterica* as described herein for treating or preventing salmonellosis.

As already mentioned hereinbefore, the mutant microorganisms and vaccine compositions of the present invention may be prepared by known techniques.

The choice of particular *Salmonella enterica* microorganism, can be made by the skilled person without undue experimentation. A preferred microorganism is selected from the group consisting of *S. Typhimurium*, S. Choleraesuis, S. Derby, *S. Infantis*, S. Bredeney, S. Rissen, S. Anatum, S. Hadar, S. Virchow, and *S. Enteritidis*.

In one embodiment the microorganism is *Salmonella Typhimurium*; more in particular the *Salmonella Typhimurium* strain MB2486, also known as the *Salmonella Typhimirium* strain 112910a (Boyen F. et al., 2005; Boyen F. et al., 2006). The latter strain has been deposited on Mar. 5, 2010 with BCCM/LMG Bacteria Collection, Laboratorium voor Microbiologie—Universiteit Gent, K. L. Ledeganckstraat 35, B-9000 Gent, Belgium and has accession number LMG P-25625.

In a particular embodiment of the present invention, the mutant strains are scsA, scsB, scsC, scsD and/or cbpA deletion mutants, and preferably scs or scsA deletion mutants, in *Salmonella Typhimurium* strain MB2486. This strain is a well-characterized porcine field strain that is able to cause persistent infections in pigs, both in field and experimental conditions and is responsive to stress (cortisol) induced recrudescence. This strain does not harbour the virulence plasmid. The contribution of virulence plasmids to the systemic phase of *Salmonella* infections is well described (Barth and Bauerfeind, 2005; Rychlik et al., 2006). At least six serotypes of *Salmonella* (serotypes Abortusovis, Choleraesuis, Dublin, *Enteritidis, Gallinarum/Pullorum*, and *Typhimurium*) are known to harbour a virulence plasmid. This does not mean is that all isolates of these serotypes carry the virulence plasmid. Pigs generally carry more *Salmonella Typhimurium* strains lacking the virulence plasmid, compared to for example cattle or horses (Bauerfeind et al., 2001). The virulence plasmid has also been reported to be often absent from strains isolated from clinically healthy pigs or pigs showing only diarrhoea (Namimatsu et al., 2006). In contrast, the virulence plasmid was frequently observed in the isolates from systemically infected pigs (Namimatsu et al., 2006). It can therefore be assumed that strains lacking the virulence plasmid are still capable of colonizing the gut of pigs, but will less frequently lead to systemic infections, both in pigs, other animals and humans.

The invention will be described in further details in the following examples and embodiments by reference to the enclosed drawings. Particular embodiments and examples are not in any way intended to limit the scope of the invention as claimed. The rationale of the examples given here for the serotype *S. Typhimurium* are equally well applicable to other *Salmonella enterica* serotypes infecting veterinary species, such as for example *Salmonella* ser. Choleraesuis (S. Choleraesuis), *Salmonella* ser. Derby (S. Derby), *Salmonella* ser. *Infantis* (S. *Infantis*), *Salmonella* ser. Bredeney (S. Bredeney), *Salmonella* ser. Rissen (S. Rissen), and *Salmonella* ser. Anatum (S. Anatum).

The following Examples illustrate the invention

Example 1

Materials and Methods
1. Chemicals

Cortisol and dexamethasone (Sigma-Aldrich, Steinheim, Germany) stock solutions of 10 mM were prepared in water and stored at −20° C. Serial dilutions of cortisol were, depending on the experiment, prepared in Luria-Bertani broth (LB, Sigma-Aldric) or in the corresponding cell medium.

2. Bacterial Strains and Growth Conditions

*Salmonella Typhimurium* strain 112910a, isolated from a pig stool sample and characterized previously by Boyen et al. (2008), was used as the wild type strain (WT) in which the spontaneous nalidixic acid resistant derivative strain ($WT_{nal}$) was constructed (Boyen et al., 2008). For fluorescence microscopy, *Salmonella Typhimurium* strain 112910a carrying the pFPV25.1 plasmid expressing green fluorescent protein (gfp) under the constitutive promoter of rpsM was used (Boyen et al., 2008; Van Immerseel et al., 2004).

Unless otherwise stated, the bacteria were generally grown overnight (16 to 20 hours) as a stationary phase culture with aeration at 37° C. in 5 ml of LB broth. To obtain highly invasive late logarithmic cultures for invasion assays, 2 µl of a stationary phase culture were inoculated in 5 ml LB broth and grown for 5 hours at 37° C. without aeration (Lundberg et al., 1999).

For the oral inoculation of pigs, the $WT_{nal}$ was used to minimize irrelevant bacterial growth when plating tonsillar, lymphoid, intestinal and faecal samples. The bacteria were grown for 16 hours at 37° C. in 5 ml LB broth on a shaker, washed twice in Hank's buffered salt solution (HBSS, Gibco, Life Technologies, Paisley, Scotland) by centrifugation at 2300×g for 10 min at 4° C. and finally diluted in HBSS to the appropriate concentration of $10^7$ colony forming units (CFU) per ml. The number of viable *Salmonella* bacteria per ml inoculum was determined by plating 10-fold dilutions on Brilliant Green agar (BGA, international medical products, Brussels, Belgium) supplemented with 20 µg per ml nalidixic acid (BGA$^{NAL}$, Sigma-Aldrich) for selective growth of the mutant strains.

3. Cell Cultures

Porcine pulmonary alveolar macrophages (PAM) were isolated by broncho-alveolar washes from lungs of euthanized 3 to 4 week old piglets, obtained from a Salmonella-negative farm, as described previously (Dom et al., 1992). The isolated cells were pooled and frozen in liquid nitrogen until further use. Prior to seeding the cells, frozen aliquots of approximately $10^8$ cells per ml were thawed and washed 3 times in Hank's buffered salt solution with $Ca^{2+}$ and $Mg^{2+}$ (HBSS+, Gibco) with 10% (v/v) fetal calf serum (FKS, Hyclone, Cramlington, England) at 4° C. Finally, these cells were cultured in Roswell Park Memorial Institute medium (RPMI, Gibco) containing 10% (v/v) FKS, 1% (v/v) L-glutamine (Gibco), 1% (v/v) sodium pyruvate (Gibco), 1% (v/v) MEM non essential amino acids (NEAA, Gibco) and 1% (v/v) penicillin-streptomycin (Gibco).

The polarized intestinal porcine epithelial (IPEC-J2) cell line is derived from jejunal epithelia isolated from a neonatal piglet (Rhoads et al., 1994; Schierack et al., 2006).

4. In vivo Trials 4.1 Experimental Inoculation of Piglets

A standardized infection model was used to create Salmonella carrier pigs (Boyen et al., 2009a). For this purpose 4 four-week-old piglets (commercial closed line based on Landrace) were obtained from a serologically negative breeding herd (according to the Belgian Salmonella monitoring program). The Salmonella-free status of the piglets was tested serologically using a commercially available Salmonella antibody test kit (IDEXX, Hoofddorp, The Netherlands), and bacteriologically via faecal sampling. The piglets were housed in pairs in separate isolation units at 25° C. under natural day-night rhythm with ad libitum access to feed and water. Seven days after they arrived, the piglets were orally inoculated with 2 ml of a suspension containing $10^7$ CFU of $WT_{nal}$ per ml HBSS.

In a first in vivo trial, we investigated the effect of different types of stress on the recrudescence of Salmonella Typhimurium by pigs. In a second in vivo trial, we injected pigs intramuscularly with 2 mg dexamethasone per kg body weight to test our hypothesis that cortisol plays a role in the recrudescence of Salmonella Typhimurium in pigs.

4.2 Effect of Different Types of Stress on the Salmonella Typhimurium Load in Carrier Pigs The animal experiment was approved by the ethical committee of the Faculty of Veterinary Medicine, Ghent University (EC 2007/101).

At day 23 post inoculation, pigs were submitted to either social stress (n=12) or feed withdrawal stress (n=6), mimicking the transport and starvation period before slaughter. The remaining six pigs were not stressed and served as a negative control group. To induce social stress, the piglets were mixed for 24 hours. One piglet was removed from its pen and transferred to another pen, which already contained 2 piglets. This was done in triplicate, so finally there were three groups of 3 piglets per pen and three groups of 1 piglet per pen. To mimic feed withdrawal stress, three groups of 2 piglets per pen were starved for 24 hours. After the stress period, the animals were humanely euthanized. Blood samples were taken and the serum cortisol concentrations were determined via a commercially available enzyme-linked immunosorbent assay (ELISA, Neogen, Lansing, USA) for the quantitative analysis of cortisol levels in biological fluids. This was conducted according to the manufacterer's instructions. Furthermore, samples of tonsils, ileocaecal lymph nodes, ileum, caecum, colon and contents of ileum, caecum and colon were collected for bacteriological analysis to determine the number of Salmonella bacteria, with a detection limit of 50 CFU per gram tissue or contents.

4.3 Effect of Dexamethasone on the Salmonella Typhimurium Load in Carrier Pigs

This in vivo experiment was approved by the ethical committee of the Faculty of Veterinary Medicine, Ghent University (EC 2010/108). The animals (n=18) were housed and inoculated as described above to create Salmonella carrier pigs (Boyen et al., 2008). At day 42 post inoculation, pigs were intramuscularly injected with either dexamethasone (Kela laboratoria, Hoogstraten, Belgium) (n=9) or HBSS (n=9). Dexamethasone is a long-acting glucocorticoid with a half-life of 36 to 72 hours (Shefrin et al., 2009), which was used at a concentration of 2 mg dexamethasone per kg body weight. It has been described that this concentration does not cause immunosuppression of the pig (Flaming et al., 1994). At 24 hours after dexamethasone injection, the animals were humanely euthanized and samples of tonsils, ileocaecal lymph nodes, ileum, caecum, colon and contents of ileum, caecum and colon were collected for bacteriological analysis, with a detection limit of 83 CFU per gram tissue or contents.

4.4 Bacteriological Analysis

All tissues and samples were weighed and 10% (w/v) suspensions were prepared in buffered peptone water (BPW, Oxoid, Basingstoke, UK). The samples were homogenized with a Colworth stomacher 400 (Seward and House, London, UK) and the number of Salmonella bacteria was determined by plating 10-fold dilutions on BGA$^{NAL}$ plates. These were incubated for 16 hours at 37° C. The samples were pre-enriched for 16 hours in BPW at 37° C. and, if negative at direct plating, enriched for 16 hours at 37° C. in tetrathionate broth (Merck, Darmstadt, Germany) and plated again on BGA$^{NAL}$. Samples that were negative after direct plating but positive after enrichment were presumed to contain 50 or 83 CFU per gram tissue or contents (detection limit for direct plating). Samples that remained negative after enrichment were presumed to contain less than 50 or 83 CFU per gram tissue or contents and were assigned value '1' prior to log transformation. Subsequently the number of CFU for all samples derived from all piglets was converted logarithmically prior to calculation of the average differences between the $\log_{10}$ values of the different groups and prior to statistical analysis.

5. Cytotoxicity Assays

The cytotoxic effect of cortisol from 0.001 to 100 µM on PAM and IPEC-J2 cells was determined using the lactate dehydrogenase cytotoxicity detection kit (LDH, Roche Applied Science, Bazel, Switzerland). Therefore PAM were seeded in a 96-well microplate at a density of approximately $2 \times 10^5$ cells per well and were allowed to attach for at least 2 hours. The IPEC-J2 cells were seeded and allowed to grow for at least 24 hours in a 96-well microplate at a density of approximately $2 \times 10^4$ cells per well in Dulbecco's modified Eagle's is medium (DMEM, Gibco) supplemented with 46.5% (v/v) Ham's F12 medium (Gibco), 5% (v/v) FKS and 1% insulin-transferrin-selenium-A supplement (ITS, Gibco).

The LDH test was used in accordance to the manufacturer's instructions and the absorbance was measured at 492 nm using a microplate ELISA reader (Multiscan M S, Thermo Labsystems, Helsinki, Finland). The percentages of cortisol induced cytotoxicity were calculated using the following formula:

$$\% \text{ cytotoxicity} = 100 \times ((a-c)/(b-c))$$

In this formula a=$OD_{492}$ derived from the wells incubated with cortisol, b=$OD_{492}$ derived from the wells incubated with 1% (v/v) Triton X-100 (Sigma-Aldrich), c=$OD_{492}$ derived from untreated control wells.

6. Effect of Cortisol on the Growth and Gene Expression of *Salmonella Typhimurium*

6.1 Effect of Cortisol on the Growth of *Salmonella Typhimurium*

The effect of cortisol concentrations ranging from 0.001 to 100 μM on the growth of *Salmonella Typhimurium* WT was examined during 24 hours. Therefore, *Salmonella Typhimurium* was grown in LB broth whether or not supplemented with cortisol. The number of CFU per ml was determined at different time points by titration of 10-fold dilutions of the bacterial suspensions on BGA. After incubation for 24 hours at 37° C., the number of colonies was counted.

6.2 Effect of Cortisol on the Gene Expression of *Salmonella Typhimurium*

RNA was isolated from *Salmonella Typhimurium* WT at logarithmic and stationary growth phase in presence or absence of 1 μM cortisol (Lundberg et al., 1999). Two $OD_{600\,nm}$ units of each culture were incubated in one-fifth culture volume 5% (v/v) phenol pH 4.3/95% (v/v) ethanol solution for 30 min on ice to stabilize the RNA. Subsequently, the RNA was extracted using the SV Total RNA purification kit (Promega, Leiden, the Netherlands).

Each condition was tested in triplicate and transcriptomic techniques involved *Salmonella Typhimurium* microarrays constructed at the Institute of Food Research, Norwich, UK, as described previously (Clements et al., 2002; Yberg et al., 2006). The microarray used in this study was the whole-genome SALSA cDNA microarray covering 5080 genes and data analysis was performed as described by Eriksson-Ygberg et al., 2006.

7. Invasion and Intracellular Survival Assays

To examine whether the ability of *Salmonella Typhimurium* to invade and proliferate in PAM and IPEC-J2 cells was altered after exposure of these cells to cortisol, invasion and intracellular survival assays were performed.

For the invasion assays, PAM and IPEC-J2 cells were seeded in 24-well plates at a density of approximately $5 \times 10^5$ cells and $10^5$ cells per well, respectively. PAM were allowed to attach for at least 2 hours and IPEC-J2 cells were allowed to grow for at least 24 hours. Subsequently, the cells were exposed to different concentrations of cortisol ranging from 0.001 to 100 μM. After 24 hours the invasion assay was performed as described by Boyen et al., 2009a. Finally the PAM and IPEC-J2 cells were washed 3 times and lysed for 10 min with 1% (v/v) Triton X-100 or 0.2% (w/v) sodium deocxycholate (Sigma-Aldrich), respectively and 10-fold dilutions were plated on BGA plates.

To assess intracellular growth, cells were seeded and inoculated as described in the invasion assay, but the medium containing 100 μg per ml gentamicin was replaced after 1 hour incubation with fresh medium containing 20 μg per ml gentamicin whether or not supplemented with different concentrations of cortisol or dexamethasone ranging from 0.001 to 100 μM. The number of viable bacteria was assessed 24 hours after infection.

To determine whether the observed effect was cortisol specific, invasion and proliferation assays were performed also after exposure of the cells to epinephrine, norepinephrine and dopamine at a concentration of 1 μM (Rupprecht et al. 1997; Rupprecht and Holsboer 1999).

To visualize the effect of cortisol on the intracellular proliferation of *Salmonella* bacteria, PAM were seeded in sterile Lab-tek® chambered coverglasses (VWR, Leuven, Belgium), inoculated with gfp-producing *Salmonella* at a is multiplicity of infection of 2:1 as described by Boyen et al., 2009a and exposed to cortisol at a high physiological stress concentration of 1 μM (Wei et al., 2010) in cell medium or to cell medium only. After 24 hours at 37° C., cells were washed three times to remove unbound bacteria and cellTrace™ calcein red-orange (Molecular Probes Europe, Leiden, The Netherlands) was added for 30 min at 37° C. Afterwards, cells were washed three times and fluorescence microscopy was carried out. In 100 macrophages, the number of macrophages containing gfp-Salmonella was counted and the average number of cell associated bacteria was calculated.

8. Statistical Analysis

All in vitro experiments were conducted in triplicate with 3 repeats per experiment, unless otherwise stated. All statistical analyses were performed using SPSS version 17 (SPSS Inc., Chicago, Ill., USA). Normally distributed data were analyzed using unpaired Student's t-test or one-way ANOVA to address the significance of difference between mean values with significance set at p≤0.05. Bonferroni as post hoc test was used when equal variances were assessed. If equal variances were not assessed, the data were analyzed using Dunnett's T3 test. Not normally distributed data were analyzed using the non parametric Kruskal-Wallis analysis, followed by Mann-Whitney U test.

Results

1. Feed Withdrawal Results in Increased Numbers of *Salmonella Typhimurium* Bacteria in the Gut of Pigs and Elevated Cortisol Blood Levels Carrier pigs subjected to feed withdrawal, 24 hours before euthanasia, showed elevated numbers of *Salmonella Typhimurium* in their bowel contents and organs in comparison to the control group. This increase was significant in the ileum (p 0.001), ileum contents (p=0.022) and colon (p=0.014). As illustrated in FIG. 1, the number of *Salmonella Typhimurium* bacteria was also increased in the caecum (p=0.136), caecum contents (p=0.156) and is colon contents (p=0.074). The social stress groups (overcrowding and isolation) showed no significant difference in comparison to the control group.

Figure 2:
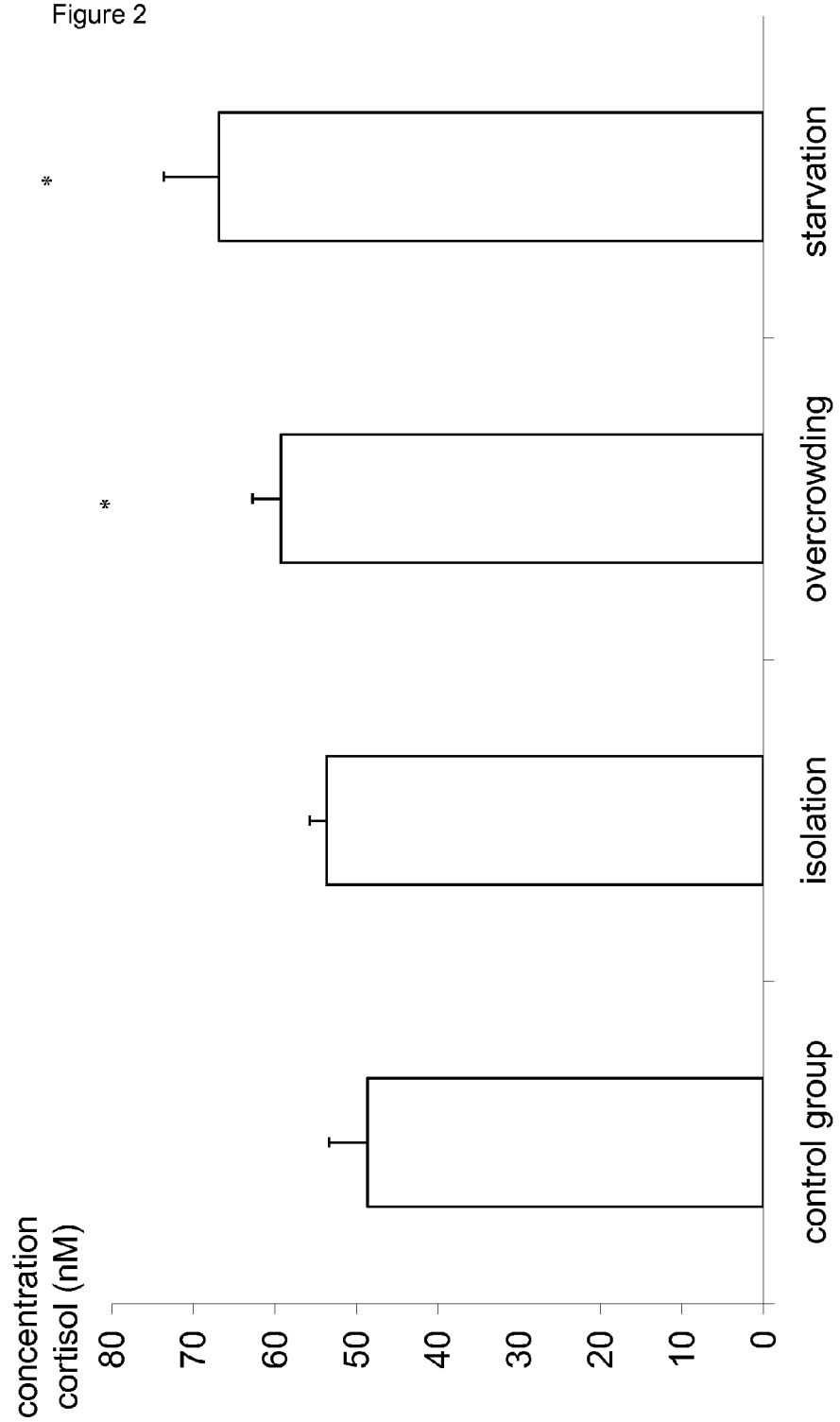
FIG. 2: Comparison of the mean serum cortisol concentrations+standard deviation from pigs that were not stressed (control group, n=6) and pigs that were submitted to either feed withdrawal (n=6) or social stress, isolation (n=3) and overcrowding (n=9), 24 hours before euthanasia. The sera of all pigs were tested in twofold and superscript (*) refers to a significant difference compared to the control group (p≤0.05).

Pigs that were subjected to feed withdrawal (p=0.004) and overcrowding (p=0.001) showed significantly elevated serum cortisol levels compared to the control group that had a mean cortisol concentration±standard deviation of 48.65±4.67 nM. Pigs that were starved 24 hours before euthanasia had the highest mean serum cortisol level±standard deviation of 66.88±6.72 nM. Pigs that were housed per 3 and housed separately, 24 hours before euthanasia had a mean cortisol concentration±standard deviation of 59.26±3.47 nM and 53.66±2.06 nM respectively. The sera of all pigs were tested in twofold and the results are shown in FIG. 2.

Figure 3:
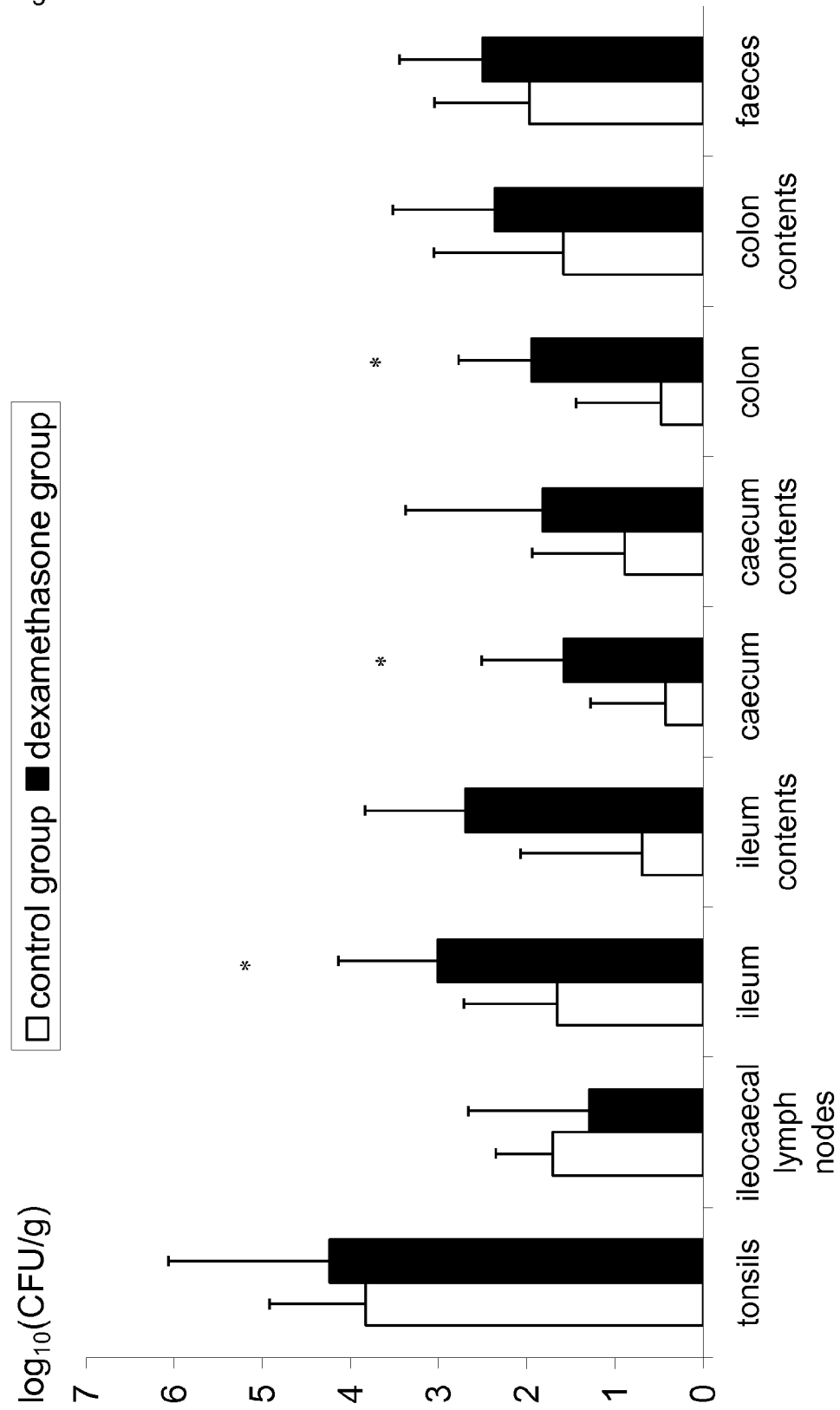
FIG. 3: Recovery of *Salmonella Typhimurium* bacteria from various organs and gut contents of carrier pigs that were injected with either HBSS (control group, n=9) or 2 mg dexamethasone per kg body weight (dexamethasone group, n=9), 24 hours before euthanasia. The $\log_{10}$ value of the ratio of CFU per gram sample is given as the mean+standard deviation. Superscript (*) refers to a significant difference compared to the control group (p≤0.05).

2. Dexamethasone Increases the Number of *Salmonella Typhimurium* Bacteria in the Gut of Carrier Pigs Carrier pigs that were intramuscularly injected with 2 mg dexamethasone per kg body weight, 24 hours before euthanasia, showed elevated numbers of *Salmonella Typhimurium* in their gut tissues and contents in comparison to the control group that was intramuscularly injected with HBSS. This increase was significant in the ileum (p=0.018), colon (p=0.003) and caecum (p=0.014). As illustrated in FIG. 3, the number of *Salmonella Typhimurium* bacteria was also increased in the ileum contents (p=0.067), caecum contents (p=0.157) and colon contents (p=0.229).

3. Cortisol does not Affect *Salmonella* Growth and Gene Expression

Cortisol concentrations ranging from 0.001 to 100 µM did not affect the growth of *Salmonella* (data not shown). The exposure of both a stationary and logarithmic phase culture of *Salmonella Typhimurium* to cortisol at a high physiological stress concentration of 1 µM did not significantly affect gene expression levels as assessed by microarray analysis (data not shown).

Figure 4:
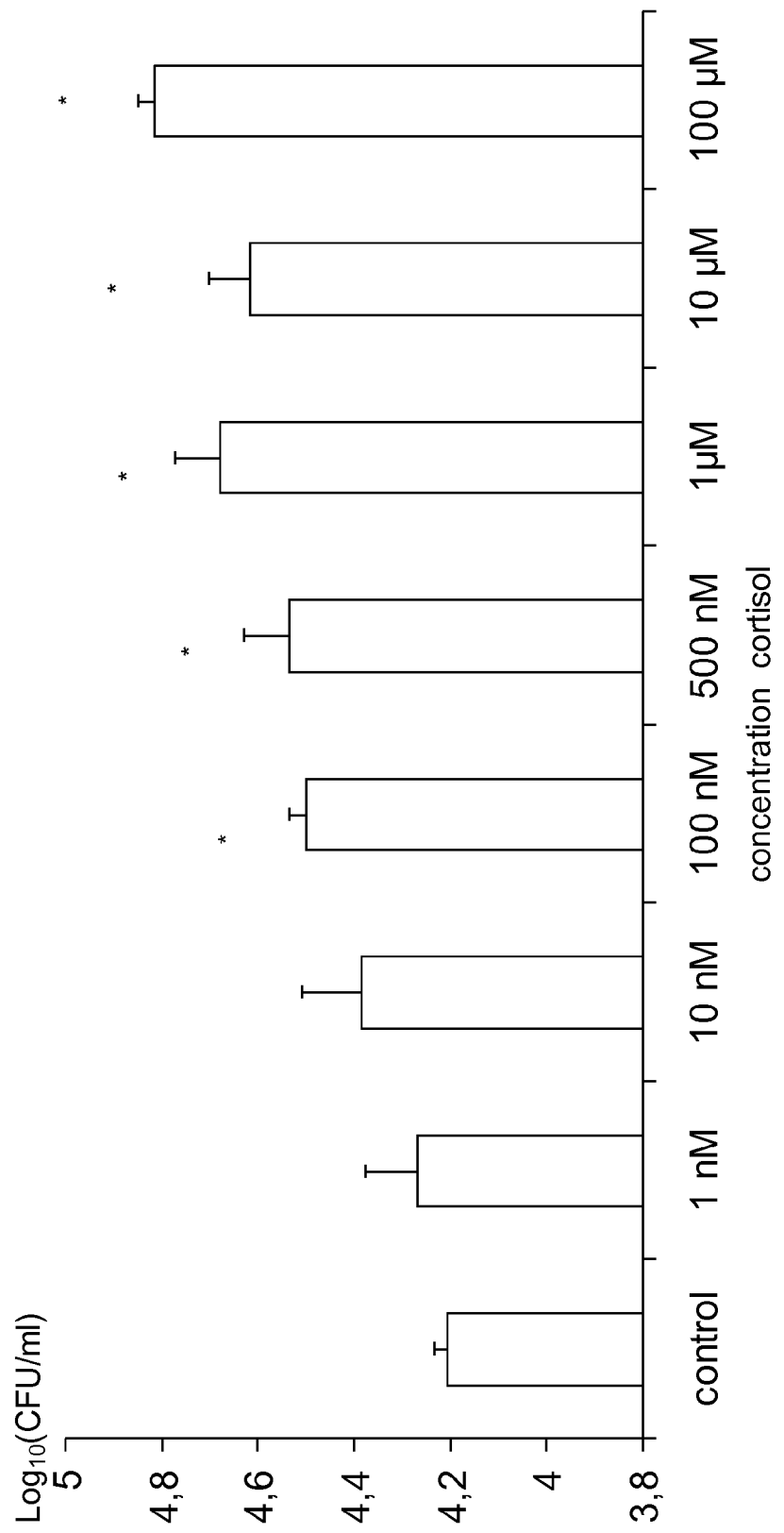
FIG. 4: Number of intracellular *Salmonella Typhimurium* bacteria in PAM that were treated with control medium or different concentrations of A) cortisol or B) dexamethasone, for 24 hours after invasion. The $\log_{10}$ values of the number of gentamicin protected bacteria+SD are shown. Results are is presented as a representative experiment conducted in triplicate. Superscript (*) refers to a significant difference compared to the control (p≤0.05).
Figure 4:
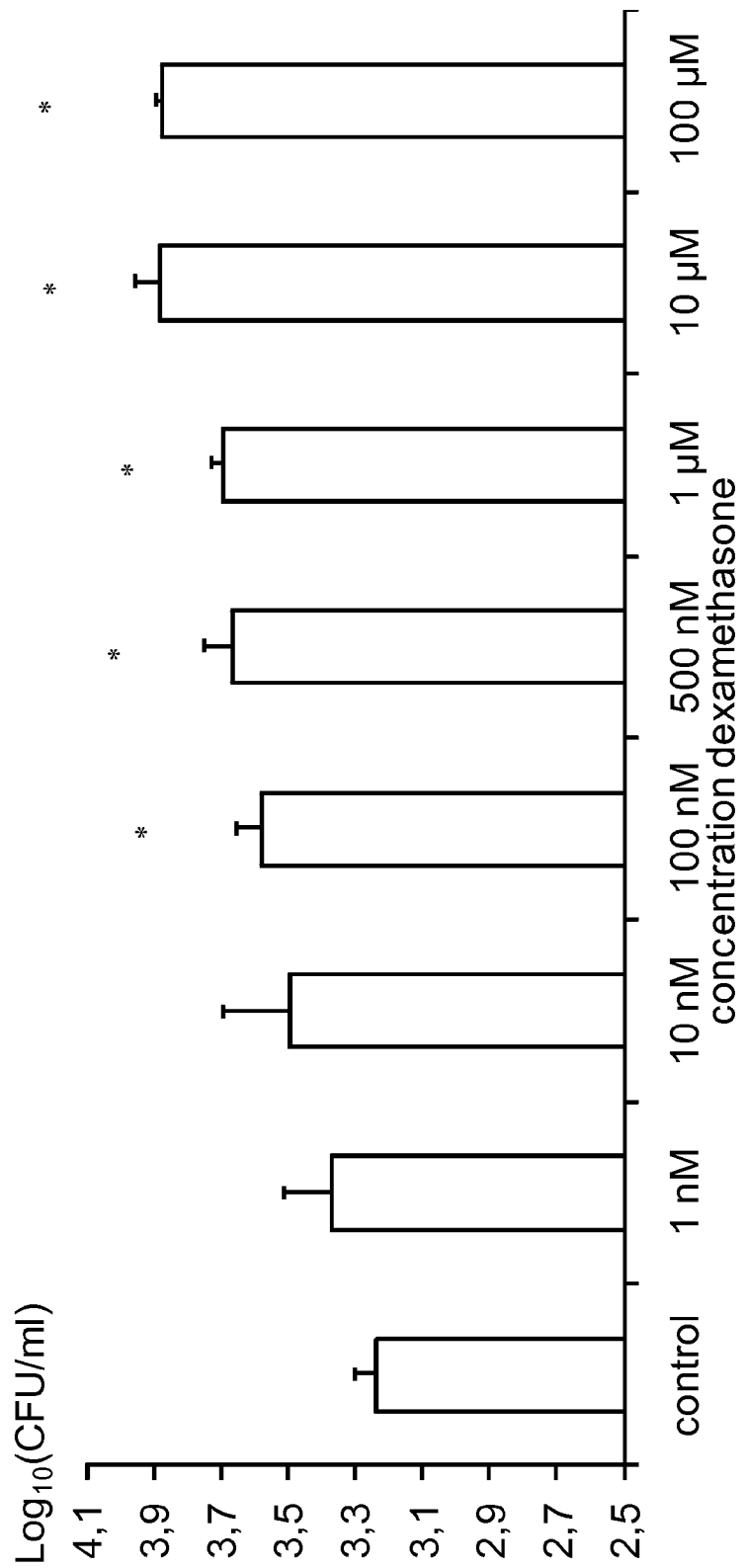

4. Cortisol and Dexamethasone Promote the Intracellular Proliferation of *Salmonella Typhimurium* in Porcine Macrophages but not in Porcine Enterocytes The results of the intracellular survival assay of *Salmonella Typhimurium* in PAM with or without prior exposure to cortisol or dexamethasone are summarized in FIG. 4. The intracellular proliferation of *Salmonella Typhimurium* was higher in PAM that were treated with cortisol or dexamethasone, for 24 hours, in comparison to non-treated cells. Exposure to concentrations of cortisol 100 nM led to a significant dose-dependent increase of the number of intracellular *Salmonella Typhimurium* bacteria. The same tendency was seen in PAM that were exposed to dexamethasone.

Cortisol and dexamethasone concentrations from 0.001 to 100 µM did neither affect the intracellular proliferation of *Salmonella Typhimurium* in IPEC-J2 cells, nor the invasion in PAM and IPEC-J2 cells (data not shown).

The enhanced intracellular proliferation of *Salmonella Typhimurium* in PAM exposed to a high physiological stress concentration of 1 µM cortisol was confirmed in a proliferation assay with gfp-Salmonella. The proliferation rate of intracellular bacteria that were exposed to 1 µM cortisol for 24 hours was increased in comparison with the control PAM, resulting in a higher mean bacterial count±standard deviation (3.1±2.72 versus 2.0±1.48 bacteria per macrophage, respectively).

Epinephrine, norepinephrine and dopamine at a concentration of 1 µM did neither affect the intracellular proliferation, nor the invasion of *Salmonella Typhimurium* in PAM and IPEC-J2 cells (data not shown).

Discussion

Our findings showed that a natural stress stimulus like feed withdrawal causes recrudescence of a *Salmonella Typhimurium* infection in carrier pigs, which could have a serious economic impact. Until now, the mechanism of stress related recrudescence of *Salmonella* in pigs is not well known.

We showed that social stress and starvation result in elevated serum cortisol levels. To verify whether an increase in corticosteroids could induce recrudescence of *Salmonella Typhimurium* in pigs, we conducted an in vivo trial in which carrier pigs were intramuscularly injected with dexamethasone. The in vivo trial showed that dexamethasone treatment causes recrudescence of *Salmonella Typhimurium* in carrier pigs. This implies that the release of corticosteroids in the bloodstream could alter the outcome of a *Salmonella* Typhimurium infection in pigs resulting in recrudescence of the infection.

We showed that this cortisol mediated effect was not the result of a direct effect on the bacterium, such as increased growth or altered pathogenicity of the bacterium. Earlier research has shown that norepinephrine in vitro promotes the growth and the motility of *Salmonella enterica* (Bearson B L & Bearson S M, 2008; Methner et al., 2008) and that in vitro pretreatment of *Salmonella Typhimurium* with norepinephrine is associated with an increased replication of this microorganism in various tissues of experimentally infected pigs (Toscano et al., 2007). However, we provide evidence that cortisol does not cause an increase in growth or any significant changes in the gene expression of *Salmonella Typhimurium*, at a physiological stress concentration of 1 µM.

In contrast to the absence of a direct effect on the bacterium, we showed that cortisol and dexamethasone promote intracellular proliferation of *Salmonella Typhimurium* in porcine macrophages, in a dose-dependent manner at concentrations (0.001 to 100 µM) that did not exert a notable effect on cell viability. *Salmonella Typhimurium* is able to survive and even multiply intracellularly after bacterial entry into host cells (Finlay B & Brumell, 2000). Therefore, we examined whether this increase of serum cortisol levels could result in altered host-pathogen interactions of *Salmonella Typhimurium* with PAM and IPEC-J2 cells.

Example 2

In Vivo Expression Technology (IVET) Screening for Intracellularly Cortisol Induced Genes of *Salmonella Typhimurium*

All the colonies showing low-level lacZY expression were analysed to identify is genes that are intracellularly expressed in PAM that might be essential for *Salmonella* survival in PAM. In total, we purified and sequenced 287 and 69 colonies from PAM whether or not treated with 1 µM cortisol, respectively. An overview of the identified genes is given in table 1. The represented data are the result of 3 independent experiments for PAM whether or not treated with 1 µM cortisol. Of all genes, only STM4067 was found in all 3 independent experiments and in both conditions. STM4067 encodes the putative ADP-ribosylglycohydrolase, which was identified by Van Parys et al. (2011) as a factor for intestinal *Salmonella Typhimurium* persistence in pigs.

CbpA, pflC, pflD and scsA were identified in all 3 independent experiments, however only in PAM that were treated with 1 µM cortisol. This implies that these genes might be intracellularly cortisol induced genes of the bacterium. PflC and pflD encode the pyruvate formate lyase activase II and the formate acetyltransferase 2, respectively. These genes both play a role in the anaerobic glucose metabolism (Nollet et al., 2005). CpbA encodes the curved DNA binding protein which is a molecular hsp40 chaperone that is involved in bacterial responses to environmental stress and which is homologous to DnaJ (Van Parys et al., 2011). ScsA encodes the suppressor of copper sensitivity protein and according to Gupta et al. (1997), it possibly functions as a peroxidase by preventing the formation of free hydroxyl radicals resulting from the reaction of copper with hydrogen peroxide (Williams & Newell, 1970).

TABLE 1

List of genes of *Salmonella Typhimurium* induced intracellularly in PAM.

| Gene | Gene product description* | Freq. + 1 µM cortisol | % + 1 µM cortisol | Freq. − 1 µM cortisol | % − 1 µM cortisol |
|---|---|---|---|---|---|
| cbpA | curved DNA-binding protein CbpA | 3/3 | 9.5 | | |
| cmk | cytidylate kinase | 2/3 | 1.4 | | |
| dnaC | DNA replication protein DnaC | 1/3 | 0.7 | | |
| dnaK | molecular chaperone DnaK | | | 1/3 | 4.3 |
| dnaT | primosomal protein DnaI | 1/3 | 0.7 | | |
| efP | elongation factor P | | | 1/3 | 2.9 |

TABLE 1-continued

List of genes of *Salmonella Typhimurium* induced intracellularly in PAM.

| Gene | Gene product description* | Freq. + 1 μM cortisol | % + 1 μM cortisol | Freq. − 1 μM cortisol | % − 1 μM cortisol |
|---|---|---|---|---|---|
| entF | enterobactin synthase subunit F | 1/3 | 0.7 | | |
| eutA | reactivating factor for ethanolamine ammonia lyase | | | 1/3 | 1.4 |
| folA | dihydrofolate reductase | 1/3 | 0.7 | | |
| gppA | guanosine pentaphosphate phosphohydrolase | 1/3 | 1.4 | | |
| gyrB | DNA gyrase, subunit B | 1/3 | 0.3 | | |
| lysS | lysyl-tRNA synthetase | 2/3 | 1.0 | | |
| marC | multiple drug resistance protein MarC | 1/3 | 0.3 | | |
| menA | 1,4-dihydroxy-2-naphtoate octaprenyltransferase | 2/3 | 6.0 | | |
| menG | ribonuclease activity regulator protein RraA | 2/3 | 4.6 | | |
| nlpB | lipoprotein | | | 2/3 | 16.0 |
| parE | DNA topoisomerase IV subunit B | | | 1/3 | 17.5 |
| pflC | pyruvate formate lyase II activase | 3/3 | 3.6 | | |
| pflD | formate acetyltransferase 2 | 3/3 | 3.6 | | |
| prfC | peptide chain release factor 3 | 1/3 | 0.3 | | |
| proP | proline/glycine betaine transporter | 1/3 | 0.7 | | |
| prpD | 2-methylcitrate dehydratase | 2/3 | 0.7 | | |
| prpE | propionyl-CoA synthetase | 2/3 | 0.7 | | |
| ratB | outer membrane protein | | | 1/3 | 1.4 |
| rfaD | ADP-L-glycero-D-mannoheptose-6-epimerase | | | 1/3 | 2.9 |
| rnT | ribonuclease T | 1/3 | 2.9 | | |
| rpoE | RNA polymerase sigma factor RpoE | 1/3 | 0.3 | | |
| rpoN | RNA polymerase factor sigma-54 | | | 1/3 | 1.4 |
| rpoZ | DNA-directed RNA polymerase subunit omega | 1/3 | 0.3 | | |
| scsA | suppression of copper sensitivity protein A | 3/3 | 8.1 | | |
| STM0014 | putative transcriptional regulator | 1/3 | 0.3 | | |
| STM0266 | putative cytoplasmic protein | 1/3 | 0.3 | | |
| STM0272 | putative chaperone ATPase | 1/3 | 0.3 | | |
| STM0409 | putative hypothetical protein | 1/3 | 0.7 | | |
| STM2314 | putative chemotaxis signal transduction protein | 1/3 | 0.7 | | |
| STM2840 | putative anaerobic nitric oxide reductase flavorubredoxin | 1/3 | 0.3 | | |
| STM4067 | putative ADP-ribosylglycohydrolase | 3/3 | 36.3 | 3/3 | 21.7 |
| tolC | outer membrane channel protein | 1/3 | 0.7 | | |
| torA | trimethylamine N-oxide reductase subunit | 1/3 | 1.0 | | |
| trpS | tryptophanyl-tRNA synthetase | 1/3 | 0.7 | | |
| yabN | transcriptional regulator SgrR | 1/3 | 0.7 | | |
| ybdZ | cytoplasmic protein | 1/3 | 0.7 | | |
| ycgB | SpoVR family protein | 1/3 | 0.3 | | |
| yfeA | hypothetical protein | 1/3 | 0.3 | | |
| yfeC | negative regulator | 1/3 | 0.3 | | |
| ygdH | nucleotide binding | 1/3 | 0.7 | | |
| ygfA | ligase | 1/3 | 0.3 | | |
| yggE | periplasmic immunogenic protein | 2/3 | 3.9 | | |
| yhbG | ABC transporter ATP-binding protein YhbG | | | 1/3 | 1.4 |
| yjbB | transport protein | 1/3 | 0.3 | 1/3 | 2.9 |
| yjjk | RNA polymerase factor sigma-54 | | | 1/3 | 26.2 |
| yqjE | inner membrane protein | 1/3 | 1.0 | | |
| yqjg | glutathione S-transferase | 1/3 | 1.7 | | |

The represented data are the result of 3 independent experiments for PAM whether (+1 μM cortisol) or not (−1 μM cortisol) treated with cortisol. The frequency (Freq.) shows the fraction of positive samples in relation to the total number of independent experiments. If an expressed gene was found more than once, then the contribution of the gene in relation to the total number of tested colonies is expressed as percentage (%). Superscript (*) refers to gene product description according to the National Center for Biotechnology Information (NCBI)

Example 3

Deletion of scsA Results in the Inhibition of the Cortisol Induced Increased Intracellular Proliferation of *Salmonella Typhimurium* in PAM and in an Upregulation of the scsBCD Operon

*Salmonella Typhimurium* deletion mutants ΔscsA and ΔcbpA, were constructed according to the one-step inactivation method described by Datsenko and Wanner (2000) and slightly modified for use in *Salmonella Typhimurium* as described by Boyen et al. (2006c). Primers used to create the gene-specific linear PCR fragments (cbpA and scsA forward and reverse) are given in table 2. The targeted genes were completely deleted from the start codon through the stop codon, as confirmed by sequencing.

TABLE 2

Primers used in this study.

| Primers | Sequences |
|---|---|
| cbpA forward | 5'-GAAACCTTTTGGGGTCCCT TCTGTATGTATTGATTTAGCGAGATGAT GCTTGTGTAGGCTGGAGCTGCTTC-3' (SEQ ID NO: 11) |
| cbpA reverse | 5'-GTGTGCAAACAAAATTCGGTG ATGGTAAAGGTGACAGTGATGTTAG CCATCATATGAATATCCTCCTTAG-3' (SEQ ID NO: 12) |
| scsA forward | 5'-CAAAACCGCGCCAGTGGCTAAGAT AACTCGCGTTAAACAGTGAGGG CGCATGTGTAGGCTGGAGCTGCTTC-3' (SEQ ID NO: 13) |
| scsA reverse | 5'-ATTTTTTCTCCGTGAATGAGTAA TTAACCGTTAGCAATAACCGGTCT GCATATGAATATCCTCCTTAG-3' (SEQ ID NO: 14) |

Figure 5:
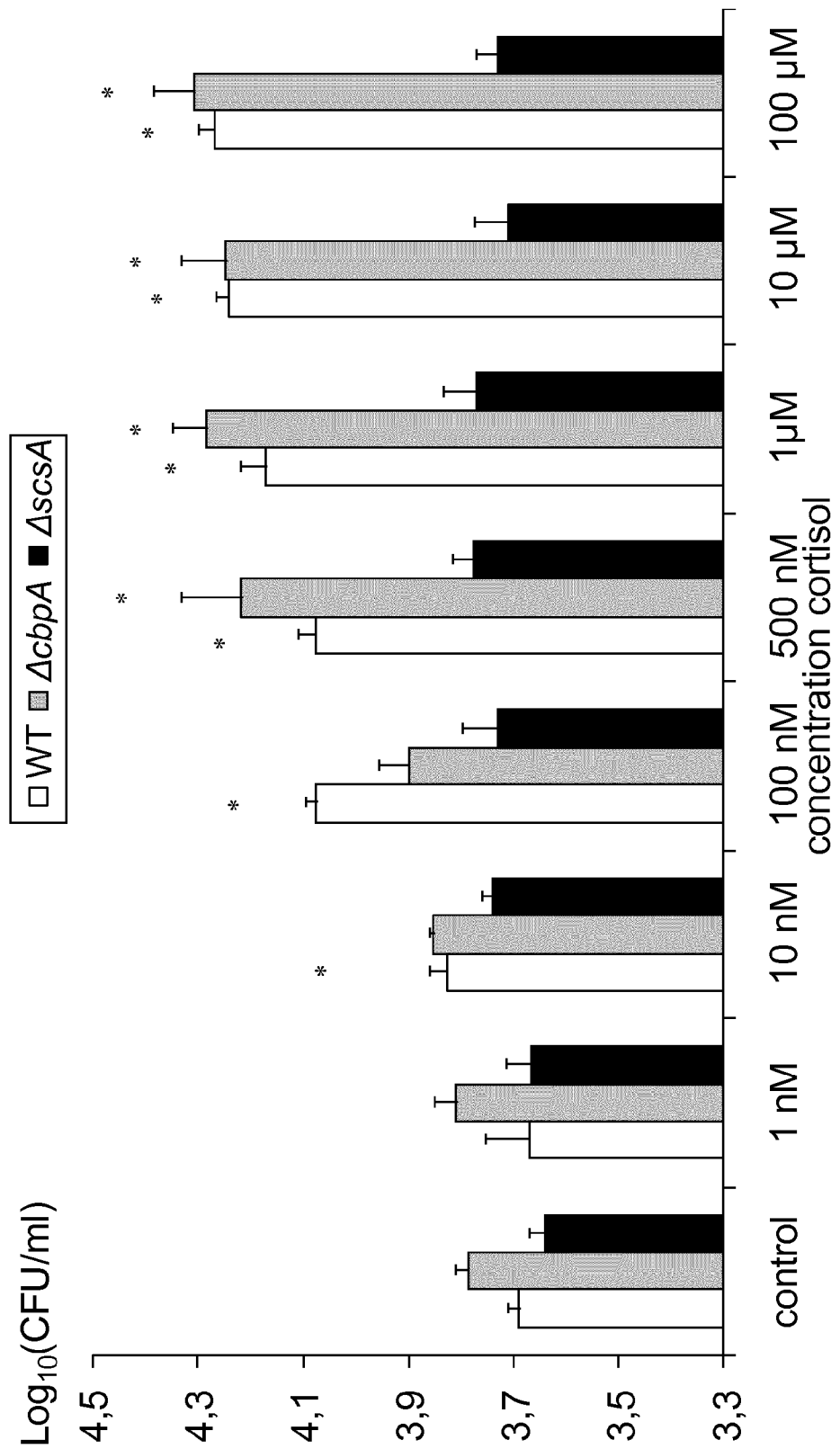
FIG. 5: Number of intracellular *Salmonella Typhimurium* WT, ΔcbpA and ΔscsA bacteria in PAM that were treated with control medium or different concentrations of cortisol, for 24 hours after invasion. The $\log_{10}$ values of the number of gentamicin protected bacteria+SD are shown. Results are presented as a representative experiment conducted in triplicate. Superscript (*) refers to a significant difference compared to the control (p≤0.05) group.

Following the IVET screening, the intracellular survival assay was repeated with *Salmonella Typhimurium* ΔscsA and ΔcbpA and compared to the WT. These results are shown in FIG. 5. The intracellular proliferation of *Salmonella Typhimurium* WT and ΔcbpA was higher in cortisol treated PAM, for 24 hours, in comparison to non-treated cells. Exposure to cortisol concentrations of respectively ≥10 nM and 500 nM led to a significant dose-dependent increase of the number of intracellular *Salmonella Typhimurium* WT or ΔcbpA bacteria. Cortisol concentrations from 0.001 to 100 µM did not affect the intracellular proliferation of *Salmonella Typhimurium* ΔscsA in PAM. This implies that the scsA gene is at least partly responsible for the increased intracellular survival of *Salmonella* WT in cortisol exposed PAM.

Microarray analysis of *Salmonella Typhimurium* ΔscsA in comparison to the WT, results in 57 and 19 genes that are differentially regulated, by ≥1.5 fold with $p \leq 0.05$, in the logarithmic and stationary phase culture, respectively. This analysis established that the deletion of scsA results in the upregulation of the scsBCD operon. ScsB, scsC and scsD were upregulated with a fold change of respectively 34.16, 19.63 and 6.50 in a stationary phase culture and 32.09, 19.90 and 6.33 in a logarithmic phase culture. The results are provided in Table 3 and 4.

Figure 8:
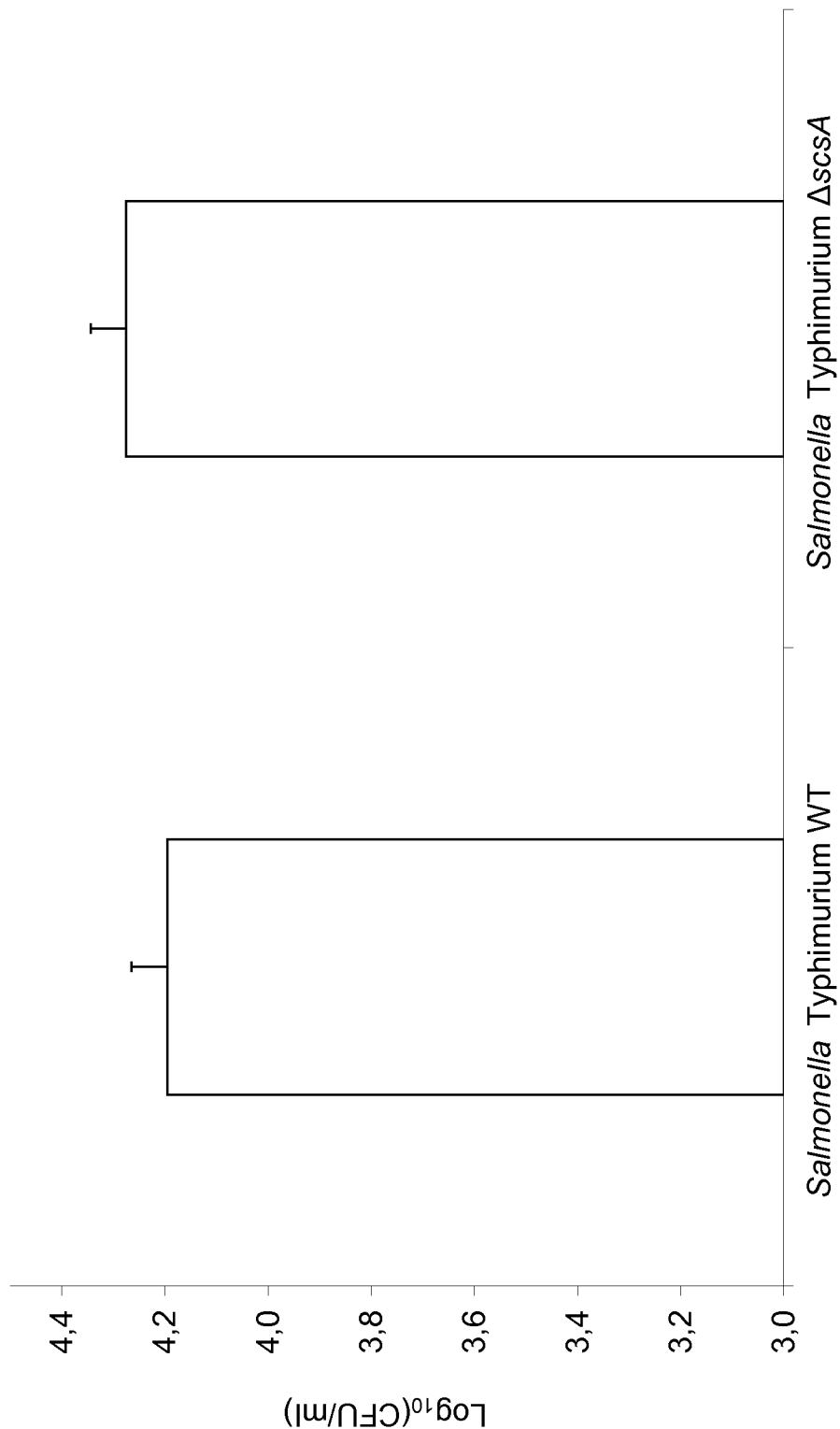
FIG. 8: The invasiveness of *Salmonella Typhimurium* WT and ΔscsA in PAM is shown. The $\log_{10}$ values of the number of gentamicin protected bacteria+standard deviation are given. Results are presented as a representative experiment conducted in triplicate.

In the stationary phase culture, an increased expression of *Salmonella* pathogenicity island (SPI-1) Type III Secretion system (T3SS) Needle Complex Protein PrgI (1.81) and the SPI-1 T3SS effector protein SipA (1.71) was observed. Furthermore, *Salmonella Typhimurium* ΔscsA grown to a logarithmic phase culture showed an increased expression of the T3SS effector protein SipC (2.19). However, the invasion capacity of *Salmonella Typhimurium* ΔscsA was not altered in comparison to the WT strain (FIG. 8).

TABLE 3

Microarray data of the stationary phase culture, showing genes differentially regulated, by ≥1.5 fold with $p \leq 0.05$, between the wild type and the ΔscsA derivative *Salmonella Typhimurium* strain.

| Gene | Fold change compared to 1 | Gene product description |
| --- | --- | --- |
| scsB | 34.16 | suppressor for copper-sensitivity B (gi|2327004); suppression of copper sensitivity: lipoprotein modification in lgt mutants of *E. coli* [*Salmonella typhimurium* LT2]. |
| scsC | 19.63 | *S. typhimurium* suppressor for copper-sensitivity C (gi|2327005) |
| scsD | 6.5 | *S. typhimurium* suppressor for copper-sensitivity D (gi|2327006) |
| prgK | 2.649 | lipoprotein; may link inner and outer membranes; PRGK protein precursor. (SW:PRGK_SALTY); cell invasion protein [*Salmonella typhimurium* LT2]. |
| corA | 2.444 | Mg transport system I; magnesium and cobalt transport protein CORA. (SW:CORA_SALTY); MIT family Mg2+/Ni2+/Co2+ transport protein [*Salmonella typhimurium* LT2]. |
| PSLT092 | 2.089 | conjugal transfer pilus assembly protein TraU |
| PSLT015 | 1.947 | putative outer membrane protein |
| prgI | 1.806 | PRGI protein. (SW:PRGI_SALTY); cytoplasmic cell invasion protein [*Salmonella typhimurium* LT2]. |
| rpsG | 1.777 | initiates assembly; (SW:RS7_SALTY); 30S ribosomal subunit protein S7 [*Salmonella typhimurium* LT2]. |
| sipA | 1.713 | SipA (gi|1172128); cell invasion protein [*Salmonella typhimurium* LT2]. |
| ptrB | 1.57 | similar to *E. coli* protease II (AAC74915.1); Blastp hit to AAC74915.1 (686 aa), 89% identity in aa 1-680; protease II [*Salmonella typhimurium* LT2]. |
| PSLT070 | 0.618 | psiA—plasmid SOS inhibition protein A |
| yfgJ | 0.591 | similar to *E. coli* orf, hypothetical protein (AAC75563.1); Blastp hit to AAC75563.1 (83 aa), 63% identity in aa 13-83; putative cytoplasmic protein [*Salmonella typhimurium* LT2]. |
| yjbG | 0.57 | similar to *E. coli* orf, hypothetical protein (AAC76998.1); Blastp hit to AAC76998.1 (245 aa), 74% identity in aa 1-245; putative periplasmic protein [*Salmonella typhimurium* LT2]. |
| yceO | 0.554 | similar to *E. coli* orf, hypothetical protein (AAC74142.1); Blastp hit to AAC74142.1 (46 aa), 64% identity in aa 10-46; putative inner membrane protein [*Salmonella typhimurium* LT2]. |
| phnW | 0.543 | 2-aminoethylphosphonate-pyruvate aminotransferase phnW (gi|11354251); 2-aminoethylphosphonate transport [*Salmonella typhimurium* LT2]. |
| prpD | 0.535 | *S. typhimurium* PRPD protein. (SW:PRPD_SALTY) |
| STM4218 | 0.525 | hypothetical protein; putative inner membrane protein [*Salmonella typhimurium* LT2]. |
| STM1698A | 0.344 | |

TABLE 4

Microarray data of the logarithmic phase culture, showing genes differentially regulated, by ≥1.5 fold with p ≤ 0.05, between the wild type and the ΔscsA derivative *Salmonella Typhimurium* strain.

| Gene | Fold change compared to 1 | Gene product description |
|---|---|---|
| scsB | 32.09 | suppressor for copper-sensitivity B (gi|2327004); suppression of copper sensitivity: lipoprotein modification in lgt mutants of *E. coli* [*Salmonella typhimurium* LT2]. |
| scsC | 19.9 | *S. typhimurium* suppressor for copper-sensitivity C (gi|2327005) |
| scsD | 6.325 | *S. typhimurium* suppressor for copper-sensitivity D (gi|2327006) |
| yjiY | 4.529 | similar to *E. coli* putative carbon starvation protein (AAC77310.1); Blastp hit to AAC77310.1 (721 aa), 96% identity in aa 6-721; putative carbon starvation protein [*Salmonella typhimurium* LT2]. |
| yjiA | 2.929 | similar to *E. coli* orf, hypothetical protein (AAC77308.1); Blastp hit to AAC77308.1 (284 aa), 90% identity in aa 1-284; putative cobalamin synthesis protein [*Salmonella typhimurium* LT2]. |
| yjiX | 2.358 | similar to *E. coli* orf, hypothetical protein (AAC77309.1); Blastp hit to AAC77309.1 (67 aa), 94% identity in aa 1-67; putative cytoplasmic protein [*Salmonella typhimurium* LT2]. |
| sipC | 2.191 | sspC protein (gi|7443298); cell invasion protein [*Salmonella typhimurium* LT2]. |
| STM1785 | 2.061 | putative cytoplasmic protein [*Salmonella typhimurium* LT2]. |
| STM4596 | 1.987 | similar to *E. coli* orf, hypothetical protein (AAC73478.1); Blastp hit to AAC73478.1 (222 aa), 31% identity in aa 55-222; putative inner membrane protein [*Salmonella typhimurium* LT2]. |
| ygaE | 1.984 | similar to *E. coli* putative transcriptional regulator (AAC75711.1); Blastp hit to AAC75711.1 (226 aa), 87% identity in aa 10-225; putative GntR family transcriptional repressor [*Salmonella typhimurium* LT2]. |
| phoQ | 1.97 | ligand is Mg+; virulence sensor protein PHOQ (SW:PHOQ_SALTY); sensory kinase protein in two-component regulatory system with PhoP [*Salmonella typhimurium* LT2]. |
| pduT | 1.838 | polyhedral bodies; similar to *E. coli* detox protein (AAC75510.1); Blastp hit to AAC75510.1 (111 aa), 41% identity in aa 16-93, 31% identity in aa 16-90; propanediol utilization protein [*Salmonella typhimurium* LT2]. |
| orgA | 1.765 | Putative RBS for orgA; RegulonDB:STMS1H002934 |
| STM3355 | 1.756 | similar to *E. coli* L-tartrate dehydratase, subunit A (AAC76097.1); Blastp hit to AAC76097.1 (303 aa), 54% identity in aa 6-299; putative tartrate dehydratase alpha subunit [*Salmonella typhimurium* LT2]. |
| rph | 1.721 | ribonuclease PH. (SW:RNPH_SALTY); RNase PH [*Salmonella typhimurium* LT2]. |
| pykF | 1.702 | formerly F; fructose stimulated; pyruvate kinase I. (SW:KPY1_SALTY); pyruvate kinase I [*Salmonella typhimurium* LT2]. |
| yhjS | 1.642 | similar to *E. coli* putative protease (AAC76561.1); Blastp hit to AAC76561.1 (523 aa), 80% identity in aa 1-523; putative cytoplasmic protein [*Salmonella typhimurium* LT2]. |
| sprB | 1.641 | transcriptional regulator SprB (gi|5007028); transcriptional regulator [*Salmonella typhimurium* LT2]. |
| pduQ | 1.637 | similar to *E. coli* CoA-linked acetaldehyde dehydrogenase and iron-dependent alcohol dehydrogenase; pyruvate-formate-lyase deactivase (AAC74323.1); Blastp hit to AAC74323.1 (891 aa), 40% identity in aa 574-860, 35% identity in aa 456-556; propanediol utilization propanol dehydrogenase [*Salmonella typhimurium* LT2]. |
| yajG | 1.626 | similar to *E. coli* putative polymerase/proteinase (AAC73537.1); Blastp hit to AAC73537.1 (226 aa), 85% identity in aa 20-226; putative lipoprotein [*Salmonella typhimurium* LT2]. |
| STM4519 | 1.599 | Paralog of *E. coli* putative aldehyde dehydrogenase (AAC74598.1); Blastp hit to AAC74598.1 (470 aa), 42% identity in aa 19-465 |
| hepA | 1.591 | Ortholog of *E. coli* probable ATP-dependent RNA helicase (AAC73170.1); Blastp hit to AAC73170.1 (968 aa), 93% identity in aa 1-968 |
| talA | 1.587 | similar to *E. coli* transaldolase A (AAC75517.1); Blastp hit to AAC75517.1 (316 aa), 89% identity in aa 1-316; transaldolase A [*Salmonella typhimurium* LT2]. |
| nhaB | 1.568 | Na+/H+ antiporter; regulator of intracellular pH; similar to *E. coli* Na+/H+ antiporter, pH independent (AAC74270.1); Blastp hit to AAC74270.1 (513 aa), 92% identity in aa 1-513; NhaB family of transport protein [*Salmonella typhimurium* LT2]. |
| yaeJ | 1.535 | Ortholog of *E. coli* orf, hypothetical protein (AAC73302.1); Blastp hit to AAC73302.1 (140 aa), 85% identity in aa 1-136 |

TABLE 4-continued

Microarray data of the logarithmic phase culture, showing genes differentially regulated, by ≥1.5 fold with p ≤ 0.05, between the wild type and the ΔscsA derivative *Salmonella Typhimurium* strain.

| Gene | Fold change compared to 1 | Gene product description |
|---|---|---|
| STM1560 | 1.531 | similar to *E. coli* 1,4-alpha-glucan branching enzyme (AAC76457.1); Blastp hit to AAC76457.1 (728 aa), 30% identity in aa 235-407, 28% identity in aa 524-576; putative alpha amylase [*Salmonella typhimurium* LT2]. |
| tolC | 1.528 | specific tolerance to colicin E1; segregation of daughter chromosomes; role in organic solvent tolerance; similar to *E. coli* outer membrane channel; specific tolerance to colicin E1; segregation of daughter chromosomes (AAC76071.1); Blastp hit to AAC76071.1 (495 aa), 89% identity in aa 1-495; outer membrane channel [*Salmonella typhimurium* LT2]. |
| ydcR | 1.502 | similar to *E. coli* multi modular; putative transcriptional regulator; also putative ATP-binding component of a transport system (AAC74521.1); Blastp hit to AAC74521.1 (468 aa), 87% identity in aa 1-468; putative gntR family regulatory protein [*Salmonella typhimurium* LT2]. |
| fliN | 0.66 | component of motor switch and energizing; flagellar motor switch protein FLIM. (SW:FLIN_SALTY); flagellar biosynthesis protein [*Salmonella typhimurium* LT2]. |
| ratB | 0.658 | RatB (gi|5107806); putative outer membrane protein [*Salmonella typhimurium* LT2]. |
| melB | 0.655 | melibiose carrier protein (thiomethylgalactoside permease)(melibiose permease) (Na+ (Li+)/melibiose symporter) (melibiosetransporter). (SW:MELB_SALTY); GPH family melibiose permease II [*Salmonella typhimurium* LT2]. |
| STM1808 | 0.654 | similar to *E. coli* orf, hypothetical protein (AAC74867.1); Blastp hit to AAC74867.1 (119 aa), 42% identity in aa 2-113; putative cytoplasmic protein [*Salmonella typhimurium* LT2]. |
| STM2694 | 0.644 | Putative RBS for STM2694; RegulonDB:STMS1H002780 |
| STM2745 | 0.624 | Putative inner membrane protein |
| amyA | 0.619 | cytoplasmic alpha-amylase. (SW:AMY2_SALTY); cytoplasmic alpha-amylase [*Salmonella typhimurium* LT2]. |
| STM2718 | 0.599 | Putative RBS for STM2718; RegulonDB:STMS1H002803 |
| STM2239 | 0.593 | Putative RBS for STM2239; RegulonDB:STMS1H002376 |
| STM2708 | 0.588 | Putative RBS for STM2708; RegulonDB:STMS1H002793 |
| STM2789 | 0.568 | similar to *E. coli* orf, hypothetical protein (AAC75706.1); Blastp hit to AAC75706.1 (360 aa), 86% identity in aa 34-360; putative cytoplasmic protein [*Salmonella typhimurium* LT2]. |
| yoaG | 0.568 | similar to *E. coli* orf, hypothetical protein (AAC74866.1); Blastp hit to AAC74866.1 (60 aa), 96% identity in aa 1-60; putative cytoplasmic protein [*Salmonella typhimurium* LT2]. |
| ygdK | 0.561 | Ortholog of *E. coli* orf, hypothetical protein (AAC75853.1); Blastp hit to AAC75853.1 (147 aa), 88% identity in aa 1-144 |
| pyrL | 0.524 | pyrbi operon leader peptide (attenuator).(SW:LPPY_SALTY); pyrBI operon leader peptide [*Salmonella typhimurium* LT2]. |
| yigF | 0.521 | hypothetical 14.6 Kda protein in corA-rarD intergenic region. (SW:YIGF_SALTY); putative inner membrane protein [*Salmonella typhimurium* LT2]. |
| STM0763 | 0.509 | similar to *E. coli* cyn operon positive regulator (AAC73441.1); Blastp hit to AAC73441.1 (299 aa), 25% identity in aa 16-288; transcriptional regulator, lysR family [*Salmonella typhimurium* LT2]. |
| STM4219 | 0.509 | putative cytoplasmic protein [*Salmonella typhimurium* LT2]. |
| PSLT069 | 0.508 | Plasmid SOS inhibition protein B |
| STM1012 | 0.498 | probable regulatory protein (gi|7467281); Gifsy-2 prophage putative regulatory protein [*Salmonella typhimurium* LT2]. |
| STM0298 | 0.493 | similar to *E. coli* orf, hypothetical protein (AAC73370.1); Blastp hit to AAC73370.1 (384 aa), 28% identity in aa 221-295; putative integrase core domain [*Salmonella typhimurium* LT2]. |
| STM1033 | 0.475 | similar to *E. coli* ATP-dependent proteolytic subunit of clpA-clpP serine protease, heat shock protein F21.5 (AAC73540.1); Blastp hit to AAC73540.1 (207 aa), 29% identity in aa 73-203; Gifsy-2 prophage Clp protease-like protein [phage Gifsy-2]. |
| STM0348 | 0.459 | hypothetical protein; putative inner membrane protein [*Salmonella typhimurium* LT2]. |
| STM0283 | 0.447 | putative inner membrane protein [*Salmonella typhimurium* LT2]. |
| STM4316 | 0.441 | hypothetical protein; putative cytoplasmic protein [*Salmonella typhimurium* LT2]. |
| ssaL | 0.41 | secretion system apparatus protein SSAL. (SW:SSAL_SALTY); secretion system apparatus protein [*Salmonella typhimurium* LT2]. |
| STM1016 | 0.392 | *S. typhimurium* hypothetical protein (gi|7467246) |

TABLE 4-continued

Microarray data of the logarithmic phase culture, showing genes
differentially regulated, by ≥1.5 fold with p ≤ 0.05, between the wild type and the
ΔscsA derivative *Salmonella Typhimurium* strain.

| Gene | Fold change compared to 1 | Gene product description |
|---|---|---|
| pldB | 0.38 | similar to *E. coli* lysophospholipase L(2) (AAC76828.1); Blastp hit to AAC76828.1 (340 aa), 81% identity in aa 1-336; lysophospholipase L(2) [*Salmonella typhimurium* LT2]. |
| PSLT083 | 0.309 | conjugal transfer protein TrbD |
| wzzE | 0.305 | Ortholog of *E. coli* putative transport protein (AAC76790.1); Blastp hit to AAC76790.1 (349 aa), 91% identity in aa 2-346 |

Example 4

Effect of Cortisol on the Protein Expression of *Salmonella Typhimurium* Infected Primary Porcine Macrophages A comparative proteome study was conducted to reveal the effects of cortisol on the protein expression of *Salmonella Typhimurium* infected primary porcine alveolar macrophages (PAM). We used a gel-free approach called isobaric tags for relative and absolute quantification (iTRAQ) in which four different isobaric labels are used to tag N-termini and lysine side chains of four different samples with four different isobaric reagents. Upon collision-induced dissociation during MS/MS, the isobaric tags are released, which results in four unique reporter ions that are used to quantify the proteins in the four different samples (Ross et al., 2004).

Sample preparation: PAM were isolated and cultured as described in Verbrugghe et al. (2011), they were seeded in 175 cm$^2$ cell culture flasks at a density of approximately $5\times10^7$ cells per flask and were allowed to attach for 2 hours. Subsequently, PAM were washed 3 times with Hank's buffered salt solution with Ca$^{2+}$ and Mg$^{2+}$ (HBSS+, Gibco) and a gentamicin protection invasion assay was performed as described by Boyen et al. (2009a). Briefly, *Salmonella* was inoculated into the cell culture flasks at a multiplicity of infection (MOI) of 10:1. To synchronize the infection, the inoculated flasks were centrifuged at 365×g for 10 min and incubated for 30 min at 37° C. under 5% CO$_2$. Subsequently, the cells were washed 3 times with HBSS+ and fresh medium supplemented with 100 µg/ml gentamicin (Gibco) was added. After 1 hour, the medium was replaced by fresh medium containing 20 µg/ml gentamicin, with or without 1 µM cortisol (Sigma-Aldrich). Twenty-four hours after infection, the cells were washed 3 times with HBSS+ and treated with lysis buffer containing 1% (v/v) Triton X-100 (Sigma-Aldrich), 40 mM Tris(hydroxymethyl)aminomethane hydrochloride (Tris, Sigma-Aldrich), a cocktail of protease inhibitors (PIs; Sigma-Aldrich) and phosphatase inhibitors (PPI, Sigma-Aldrich), 172.6 U/ml deoxyribonuclease I (DNase I, Invitrogen, USA) and 100 mg/ml ribonuclease A (RNase A, Qiagen, Venlo, The Netherlands). Subsequently, cell debris and bacteria were removed by centrifugation at 2300×g for 10 min at 4° C. Two % (v/v) tributylphosphine (TBP, Sigma-Aldrich) was added to the supernatant followed by centrifugation at 17 968×g for 10 min. The supernatant was held on ice until further use and the pellet was dissolved and sonicated (6 times 30 sec), using an ultrasonic processor XL 2015 (Misonix, Farmingdale, N.Y., USA), in reagent 3 of the Ready Prep Sequential extraction kit (Bio-Rad, Hercules, Calif., USA). This was centrifugated at 17 968×g for 10 min. Both supernatants were combined and a buffer switch to 0.01% (w/v) SDS in H$_2$O was performed using a Vivaspin column (5000 molecular weight cut off Hydrosarts, Sartorius, Germany). Protein concentration was determined using the Bradford Protein Assay (Thermo Fisher Scientific, Rockford, USA) according to the manufacturer's instructions.

Trypsin digest and iTRAQ labeling: Digest and labeling of the samples (100 µg proteins per sample) with iTRAQ reagents was performed according to the manufacturer's guidelines (AB Sciex, Foster City, Calif., USA). Individual samples of cortisol treated or untreated PAM were analyzed in the same run, making paired comparisons possible and minimizing technical variation. Each condition was run in duplicate using different labels of the four-plex labeling kit. The experiment was conducted in twofold and the labeling of the samples was as follows: run 1 (untreated PAM sample 1: 114—untreated PAM sample 2: 115—treated PAM sample 1: 116—treated PAM sample 2: 117)—run 2 (untreated PAM sample 3: 114—untreated PAM sample 4: 115—treated PAM sample 3: 116—treated PAM sample 4: 117). After labeling, 6 µl of a 5% (v/v) hydroxylamine solution was added to hydrolyze unreacted label and after is incubation at room temperature for 5 min, the samples were pooled, dried and resuspended in 5 mM KH$_2$PO$_4$ (15% (v/v) acetonitrile) (pH 2.7). The combined set of samples was first purified on ICAT SCX cartridges, desalted on a C18 trap column and finally fractionated using SCX chromatography. Each fraction was analyzed by nano LC-MSMS as described by Bijttebier et al. (2009).

Data analysis: With no full pig protein database available, different search parameters and databases, both EST and protein, were validated to obtain maximum spectrum annotation. Best results (39% of spectra annotated above homology threshold with a 3.71% false discovery rate in the decoy database) were obtained when searching NCBI Mammalia. For quantification, data quality was validated using ROVER (Colaert et al., 2011). Based on this validation a combined approach was used to define recurrently different expression patterns. In a first approach, the four ratios that can be derived from each run (114/116, 115/117, 114/117 and 115/116) were log-transformed and a t-test was used to isolate protein ratios significantly different from 0 in each run. In a second approach, the two runs were merged into one file and the 114/116 and 115/117 ratios of each run were log-transformed and these ratios were multiplied (log*log). Proteins with recurrent up- or downregulation result in positive log*log protein ratios and those >0.01 were retained and listed. Proteins that were present in both lists were considered unequivocally differentially expressed. This combined approach allows defining proteins with relatively low, but recurrent expressional differences.

The Contribution of the Cytoskeleton to Cortisol Induced Intracellular Proliferation of *Salmonella Typhimurium* in Primary Porcine Macrophages The contribution of the cytoskeleton during the cortisol induced increased proliferation of *Salmonella Typhimurium* in PAM was investigated using cytochalasin D (Sigma) for the inhibition of F-actin polymerization, and nocodazole (Sigma) as an inhibitor for microtubule formation. Therefore, PAM is were seeded in 24-well plates at a density of approximately $5 \times 10^5$ cells per well, allowed to attach for 2 hours and infected with *Salmonella*, as described in the iTRAQ analysis. To assess the intracellular proliferation, the medium containing 100 μg/ml gentamicin was replaced after 1 hour incubation with fresh medium containing 20 μg/ml gentamicin, with or without 1 μM cortisol, 2 μM cytochalasin D and/or 20 μM nocodazole. Twenty-four hours after infection, the number of viable bacteria was determined by plating 10-fold dilutions on Brilliant Green Agar (BGA, international medical products, Brussels, Belgium).

Results

Differential Protein Expression of *Salmonella Typhimurium* Infected Primary Porcine Macrophages after Exposure to Cortisol Peptides from trypsin digested proteins were labeled with isobaric mass tag labels and analyzed by 2-D LC MSMS. Collision-induced dissociation results in the release of these isobaric tags, which allows relative quantification of the peptides. A broad comparison between cortisol treated and untreated *Salmonella Typhimurium* infected PAM, resulted in the identification of 23 proteins with relatively low, but recurrent expressional differences, as shown in Table 5. Two of these proteins showed higher levels in untreated PAM, whereas 21 of them were more abundant in cortisol treated PAM. Proteomic analysis revealed a cortisol increased expression of beta tubulin, capping protein beta 3 subunit, thymosin beta-4, actin-related protein 3B, tropomyosin 5, and elongation factor 1-alpha 1 isoform 4, which are 6 proteins that are involved in reorganizations of the cytoskeleton. Furthermore, cortisol caused an increased expression of transketolase, Cu—Zn superoxide dismutase, glutaredoxin and prostaglandin reductase 1 (15-oxoprostaglandin 13-reductase) which play a role in the macrophage defense mechanisms.

TABLE 5

Differential protein expression of *Salmonella* infected macrophages after exposure to cortisol.

| Protein name* | Function* | T-test | log*log |
|---|---|---|---|
| Cytochrome c oxidase subunit 5B, mitochondrial | This protein is one of the nuclear-coded polypeptide chains of cytochrome c oxidase, the terminal oxidase in mitochondrial electron transport. | 0.7 | 0.8 |
| Pulmonary surfactant-associated protein B | Pulmonary surfactant-associated proteins promote alveolar stability by lowering the surface tension at the air-liquid interface in the peripheral air spaces. | 0.7 | 0.8 |
| Tropomyosin 5 | Is an actin-binding protein that regulates actin mechanics. | 1.2 | 1.2 |
| Cathepsin B precursor | Thiol protease which is believed to participate in intracellular degradation and turnover of proteins. | 1.2 | 1.2 |
| Peptidyl-prolyl cis-trans isomerase B | Peptidyl-prolyl cis-trans isomerase B accelerates the folding of proteins. It catalyzes the cis-trans isomerization of proline imidic peptide bonds in oligopeptides. | 1.2 | 1.2 |
| Transketolase | Is an enzyme of the pentose phasphate pathway and the calvin cycle that catalysis the conversion of Sedoheptulose 7-phosphate + D-glyceraldehyde 3-phosphate to D-ribose 5-phosphate + D-xylulose 5-phosphate in both directions. | 1.2 | 1.3 |
| Translation elongation factor 1 alpha 2 isoform 1 | This protein promotes the GTP-dependent binding of aminoacyl-tRNA to the A-site of ribosomes during protein biosynthesis. | 1.3 | 1.3 |
| L-lactate dehydrogenase A chain | Is an enzyme that catalyses the conversion from (S)-lactate + NAD+ to pyruvate + NADH in the final step of anaerobic glycolysis. | 1.2 | 1.2 |
| Cu-Zn-superoxide dismutase | Is an enzyme that catalysis the dismutation of superoxide into oxygen and hydrogen peroxide. | 1.2 | 1.2 |
| Cytochrome c oxidase subunit IV | This protein is one of the nuclear-coded polypeptide chains of cytochrome c oxidase, the terminal oxidase in mitochondrial electron transport. | 1.2 | 1.3 |
| Malate dehydrogenase, mitochondrial | Is an enzyme in the citric acid cycle that catalyzes the conversion of (S)-malate + NAD+ into oxaloacetate + NADH and vice versa | 1.2 | 1.3 |
| Elongation factor 1-alpha 1 isoform 4 | This protein promotes the GTP-dependent binding of aminoacyl-tRNA to the A-site of ribosomes during protein biosynthesis. | 1.2 | 1.3 |
| Thymosin beta-4 | Plays an important role in the organization of the cytoskeleton. Binds to and sequesters actin monomers (G actin) and therefore inhibits actin polymerization. | 1.2 | 1.3 |
| Capping protein beta 3 subunit | Cellular component of the F-actin capping protein complex that binds to and caps the barbed ends of actin filaments, thereby regulating the polymerization of actin monomers but not severing actin filaments. | 1.2 | 1.3 |
| Annexin A1 | Calcium/phospholipid-binding protein which promotes membrane fusion and is involved in exocytosis. This protein regulates phospholipase A2 activity. | 1.3 | 1.3 |
| Neutral alpha-glucosidase AB | Cleaves sequentially the 2 innermost alpha-1,3-linked glucose residues from the Glc2Man9GlcNAc2 oligosaccharide precursor of immature glycoproteins. | 1.3 | 1.3 |
| CD14 antigen | The protein is a surface antigen that is preferentially expressed on monocytes/macrophages. It cooperates with other proteins to mediate the innate immune response to bacterial lipopolysaccharide. | 1.3 | 1.3 |
| Beta tubulin | Tubulin is the major constituent of microtubules. It binds two moles of GTP, one at an exchangeable site on the beta chain and one at a non-exchangeable site on the alpha-chain. | 1.3 | 1.4 |
| Actin-related protein 3B | May function as ATP-binding component of the Arp2/3 complex which is involved in regulation of actin polymerization and together with an activating nucleation-promoting factor (NPF) mediates the formation of branched actin networks. | 1.4 | 1.4 |
| Granulins | Granulins have possible cytokine-like activity. They may play a role in inflammation, wound repair, and tissue remodeling. | 1.4 | 1.5 |
| Glutaredoxin | Is a redox enzyme that uses glutathione as a cofactor and which plays a role in cell redox homeostasis. | 1.4 | 1.4 |
| Vat1 protein | This protein belongs to the oxidoreductases that play a role in oxidation-reduction processes. | 1.7 | 1.7 |

TABLE 5-continued

Differential protein expression of *Salmonella* infected macrophages after exposure to cortisol.

| Protein name* | Function* | T-test | log*log |
|---|---|---|---|
| Prostaglandin reductase 1 | Catalyzes the conversion of leukotriene B4 into 12-oxo-leukotriene B4. This is an initial and key step of metabolic inactivation of leukotriene B4. | 1.8 | 1.8 |

Figure 7:
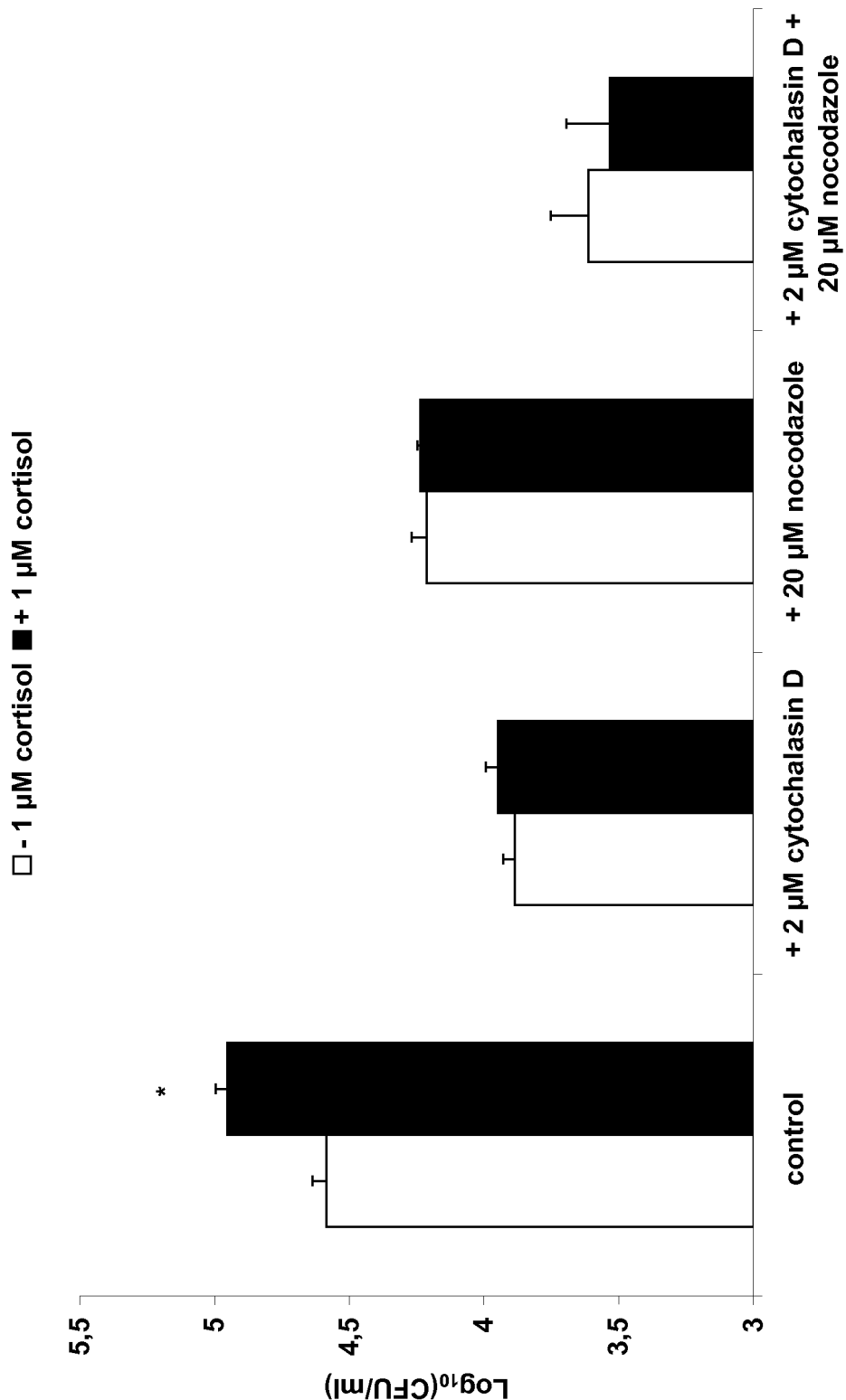
FIG. 7: Number of intracellular *Salmonella Typhimurium* bacteria in PAM that were treated with control medium, 2 μM cytochalasin D, 20 μM nocodazole or the combination of both, for 24 hours after invasion. The white bars represent medium without cortisol and the black bars represent medium with 1 μM cortisol. The $\log_{10}$ values of the number of gentamicin protected bacteria+standard deviation are shown. Results are presented as a representative experiment conducted in triplicate. Superscript (*) refers to a significant difference compared to the condition without cortisol (p≤0.05).

Differentially expressed proteins identified in cortisol treated PAM in comparison to untreated PAM, by use of iTRAQ analysis coupled to 2-D LC MSMS. Superscript (*) refers to protein description according to the UniProtKB/Swiss-Prot protein sequence database.
T-test: Protein ratio treated/untreated PAM of the T-test approach
Log*log: Protein ratio treated/untreated PAM of the log*log approach Cortisol Induced Increased Survival of *Salmonella Typhimurium* is Both Microfilament and Microtubule Dependent As earlier described, exposure to 1 µM cortisol for 24 hours led to a significant increase of the number of intracellular *Salmonella Typhimurium* bacteria compared to untreated PAM (Verbrugghe et al., 2011). In the present study, we showed that this cortisol induced increased intracellular proliferation of *Salmonella Typhimurium* is microfilament and microtubule dependent. The is treatment of *Salmonella Typhimurium* infected PAM with cytochalasin D and/or nocodazole resulted in the inhibition of the cortisol induced increased survival of the bacterium. Results are summarized in FIG. 7.

Example 5

Reducing Stress Induced Recrudescence of Live *Salmonella* Vaccine Strains 5.1. Materials and Methods Animal experiments were carried out in strict accordance with the recommendations in the European Convention for the Protection of Vertebrate Animals used for Experimental and other Scientific Purposes. The experimental protocols and care of the animals were approved by the Ethical Committee of the Faculty of Veterinary Medicine, Ghent University (EC 2011/099 and EC 2011/116).

*Salmonella* Strains

For oral vaccination of pigs, a commercially available, live, attenuated, *Salmonella Typhimurium* vaccine (Salmoporc® IDT, Rodleben) was used. This strain is formulated based on a double attenuated *Salmonella Typhimurium* mutant strain (phage type DT 9), unable to synthesize both adenine and histidine (Lindner et al., 2007). The strain is distinguishable from field isolates of the same serotype on the basis of its auxotrophy using a rapid test (IDT *Salmonella* Diagnostic Kit) within 24-48 hours (Eddicks et al., 2009).

Knock-out Mutants

*Salmonella Typhimurium* strain 112910a, phage type 120/ad, isolated from a pig stool sample and characterized previously (Boyen et al., 2008b), and several isogenic knock-out mutants, were used in this study. The knock-out mutants where constructed as described before (Boyen et al, 2006), primers is used in this study are shown in table 6.

Briefly, the genes of interest were first substituted by a PCR adjusted antibiotic resistance cassette (kanamycin) using the helper plasmid pKD46. This plasmid encodes the phage λ Red system, which promotes recombination between the native gene and the PCR adjusted antibiotic resistance cassette. Recombinant clones were selected by plating on Luria-Bertani agar (LB; Sigma Aldrich Chemie Gmbh, Steinheim, Germany) containing 100 µg/ml kanamycin. The substitution was confirmed by PCR. In the last step, the antibiotic resistance cassettes were eliminated using the helper plasmid pCP20. The targeted genes were completely deleted from the start codon through the stop codon, as confirmed by sequencing.

TABLE 6

Primers used in this study to create the deletion mutants ΔscsA, ΔscsB, ΔscsC, ΔscsD, ΔscsABCD and ΔcbpA.

| Primers | Sequences 5'-3' |
|---|---|
| scsA forward | CAAAACCGCGCCAGTGGCTAAGATAACTCGCGTTAAACAGTGAGGGCGCAT GTGTAGGCTGGAGCTGCTTC (SEQ ID NO: 13) |
| scsA reverse | ATTTTTTCTCCGTGAATGAGTAATTAACCGTTAGCAATAACCGGTCTGCATAT GAATATCCTCCTTAG (SEQ ID NO: 14) |
| scsB forward | CGGTTATTGCTAACGGTTAATTACTCATTCACGGAGAAAAAATTGTGTAGGC TGGAGCTGCTTC (SEQ ID NO: 15) |
| scsB reverse | CGCGATGCTCAGCGTCGAAAACAGCGCCAGCAGTAAAACAATCATGTATTC ATATGAATATCCTCCTTAG (SEQ ID NO: 16) |
| scsC forward | GCGATGCGGTATTACAAACGTTGAAAAAAGCGAAAGGAATAACCCAATGAT GTGTAGGCTGGAGCTGCTTC (SEQ ID NO: 17) |
| scsC reverse | GCTTCACGCAGCCAACGCCGCAGTTTACCCGCCATTCATATGAATATCCTC CTTAG (SEQ ID NO: 18) |
| scsD forward | GCCCTGGGATACGCtGGAAGCGGTGGTGAAAGAAAAACTGGCGTCTGCCAT GTGTAGGCTGGAGCTGCTTC (SEQ ID NO: 19) |
| scsD reverse | GATTTCGCAAAACGGGGGTTTTTCTTACAGTAAACGCGTTAGCGCCGGGAC ATATGAATATCCTCCTTAG (SEQ ID NO: 20) |
| scsABCD forward | CAAAACCGCGCCAGTGGCTAAGATAACTCGCGTTAAACAGTGAGGGCGCAT GTGTAGGCTGGAGCTGCTTC (SEQ ID NO: 21) |

TABLE 6-continued

Primers used in this study to create the deletion mutants
ΔscsA, ΔscsB, ΔscsC, ΔscsD, ΔscsABCD and ΔcbpA.

| Primers | Sequences 5'-3' |
|---|---|
| scsABCD reverse | GATTTCGCAAAACGGGGGTTTTCTTACAGTAAACGCGTTAGCGCCGGGAC ATATGAATATCCTCCTTAG (SEQ ID NO: 22) |
| cbpA forward | GAAACCTTTTGGGGTCCCTTCTGTATGTATTGATTTAGCGAGATGATGCTTG TGTAGGCTGGAGCTGCTTC (SEQ ID NO: 11) |
| cbpA reverse | GTGTGCAAACAAAATTCGGTGATGGTAAAGGTGACAGTGATGTTAGCCATC ATATGAATATCCTCCTTAG (SEQ ID NO: 12) |

For experimental infection of mice, an invasive, spontaneous nalidixic acid resistant *Salmonella Typhimurium* strain 112910aNal[20], resistant to 20 µg/ml nalidixic acid, was used.

Effect of Dexamethasone on Recrudescence of a Live *Salmonella Typhimurium* Vaccine Strain in Pigs In this in vivo experiment we investigated whether a subcutaneous injection of dexamethasone is able to induce recrudescence of a live commercial *Salmonella Typhimurium* vaccine in pigs. For that purpose, twenty, three-week-old, piglets were used. The *Salmonella*-free status of the piglets was is tested serologically using a commercially available enzyme-linked immunosorbent assay (ELISA) (IDEXX Laboratories) according to the manufacturer's instructions. All animals were housed together at 25° C. under natural day-night rhythm with ad libitum access to feed and water and were orally vaccinated with 1 ml of the live *Salmonella Typhimurium* vaccine, Salmoporc®. Two weeks later, ten animals received an intramuscular injection of 2 mg dexamethasone (Kela laboratoria, Hoogstraten, Belgium) per kg body weight, to mimic pre-slaughter stress conditions. This dose was shown to cause recrudescence of *Salmonella Typhimurium* in pigs (Verbrugghe et al., 2011). Ten pigs served as a control group and were intramuscularly injected with 2 ml of Hank's buffered salt solution (HBSS; Gibco Life Technologies, Paisley, Scotland). Twenty-four hours later, all animals were humanely euthanized and organ samples were taken for bacteriological analysis.

Developing a Mice Model that Mimics Stress Related Recrudescence of *Salmonella Typhimurium*

In this in vivo experiment we evaluated whether dexamethasone increases the number of *Salmonella Typhimurium* bacteria in the gut of *Salmonella Typhimurium* infected mice in order to create a mice model that allows screening of bacterial genes that might be involved in dexamethasone induced recrudescence of *Salmonella*. For that purpose, eighteen, four week old DBA/2J mice, intermediately sensitive to *Salmonella Typhimurium* infections (Sebastiani et al., 2002) and eighteen, four week old BALB/c mice, highly susceptible to *Salmonella Typhimurium* infections (Sebastiani et al., 2002), were housed in filter-topped cages at 25° C. under natural day-night rhythm with ad libitum access to feed and water and enriched with mouse houses and play tunnels. Five days after arrival, all mice were infected with a total of 1·10$^6$ CFU of *Salmonella Typhimurium* strain 112910aNal[20] by the orogastric route. At day 7 post inoculation (p.i.) six BALB/c mice were subcutaneously injected once with 100 mg/kg dexamethasone. Simultaneously, six BALB/c mice received a subcutaneous injection of 25 mg/kg dexamethasone, which was repeated after three hours. Fourteen days p.i. six DBA/2J mice were subcutaneously (SC) injected once with 100 mg/kg dexamethasone and contemporary six DBA/2J mice received a SC injection of 25 mg/kg dexamethasone (repeated after three hours). Six mice of each strain received a SC injection of 200 µl HBSS (24 h before euthanasia) and were used as a control group. Twenty-four hours after the SC injection of dexamethasone, all animals were humanely euthanized and samples of spleen, liver and cecum were collected for bacteriological analysis.

The Role of scs Genes in a Mice Model Mimicking Stress Related Recrudescence of *Salmonella Typhimurium*

A mice model was used to verify whether scsA, scsB, scsC, scsD or the entire scs locus is important in dexamethasone related recrudescence in vivo. Therefore, three to four week old DBA/2J mice were used and randomly allocated in six groups of sixteen mice. The animals were housed in filter-topped cages at 25° C. under natural day-night rhythm with ad libitum access to feed and water and enriched with mouse houses and play tunnels. Mice were inoculated with a total of 1·10$^6$ CFU of *Salmonella Typhimurium* or its isogenic scsA, scsB, scsC, scsD or scsABCD knock-out mutants. At day 14 p.i., eight animals of each group were SC injected with 100 mg/kg dexamethasone and eight mice were SC injected with 200 µl HBSS and served as a control group. Twenty-four hours later, all mice were humanely euthanized. Spleen, liver and cecum samples were examined for the number of *Salmonella Typhimurium* bacteria.

Bacteriological Analysis

All organ samples were weighed and 10% (w/v) suspensions were prepared in buffered peptone water (BPW, Oxoid, Basingstoke, United Kingdom). The samples were homogenized with a Colworth stomacher 400 (Seward and House, London, United Kingdom) and the number of *Salmonella* bacteria was determined by plating 10-fold dilutions on XLD plates (for porcine organ samples and organ samples of the last mice in vivo trial) or on BGA$_{Nal20}$ plates (for samples collected to optimize the mice model). All plates were incubated for 16 hours at 37° C. The samples were pre-enriched for 16 hours in BPW at 37° C. and, if negative at direct plating, enriched for 16 hours at 37° C. in tetrathionate broth (Merck KGaA, Darmstadt, Germany) and plated again on BGA$_{Nal20}$ or XLD plates.

Samples that were negative after direct plating but positive after enrichment were presumed to contain 83 CFU/gram tissue or contents (detection limit for direct plating). Samples that remained negative after enrichment were presumed to contain less than 83 CFU/gram tissue or contents and were assigned value '1' prior to log transformation. Subsequently the number of CFU for all samples derived from all animals was converted logarithmically prior to calculation of the average differences between the log$_{10}$ values of the is different groups and prior to statistical analysis.

Statistical Analysis

In all experiments, statistical analysis was performed using a one-way ANOVA test (in case of homogeneity of variances), with posthoc Bonferroni corrections or a nonparametric Mann-Whitney-U-test (in case of non-homogeneity of variances), using the SPSS Statistics 19.0 software (SPSS Inc., Chicago, USA). A P-value of <0.05 was considered significant.

5.2. Results

Figure 9:
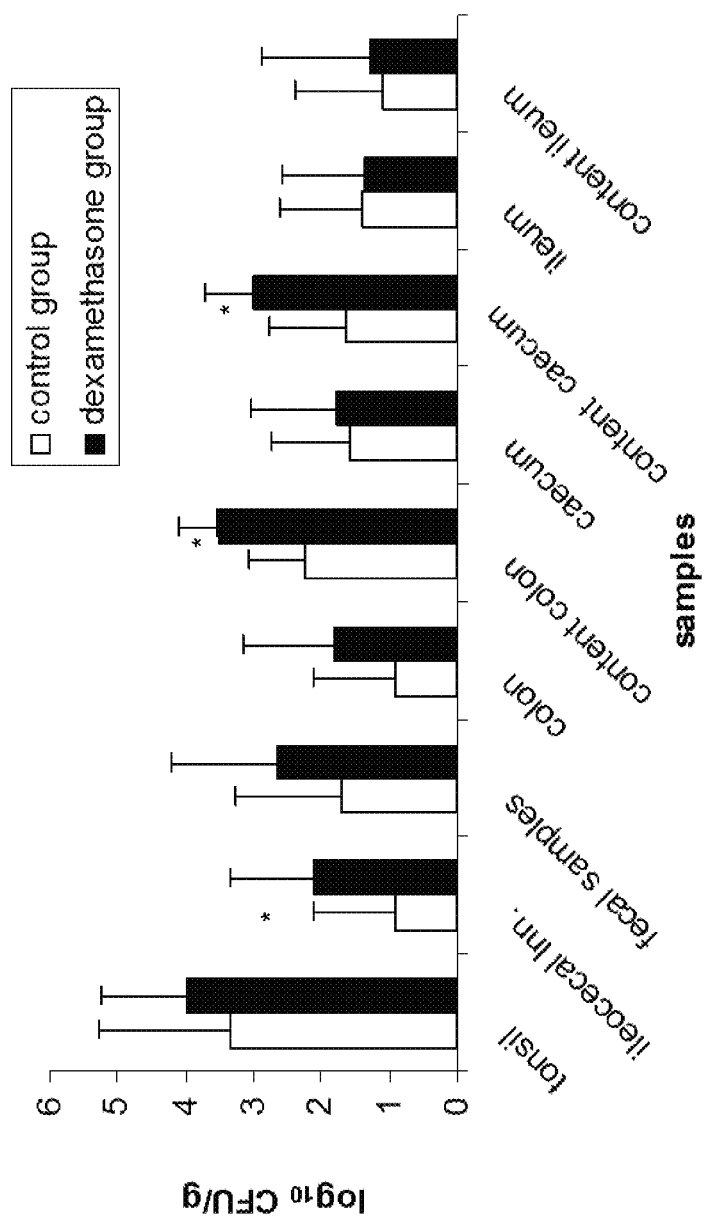
FIG. 9: Recovery of Salmoporc® from various organs of pigs 14 days post vaccination. Black bars represent vaccinated pigs that received an intramuscular injection of dexamethasone (2 mg/kg) and white bars represent vaccinated animals that received an intramuscular injection of HBSS (control group). The mean $\log_{10}$ values of the number of CFU per gram sample with is their standard deviations are given. An asterisk (*) refers to a significant difference (P<0.05) between the control group and the dexamethasone group.

Dexamethasone Promotes Recrudescence of a *Salmonella Typhimurium* Live Vaccine Strain in Pigs In this experiment we determined to which extent the commercially available, *Salmonella Typhimurium* live vaccine, Salmoporc®, is subject to recrudescence when vaccinated pigs are treated with 2 mg/kg dexamethasone, 24 hours before euthanasia. FIG. 9 illustrates that recovery of Salmoporc® was higher in organ samples and contents of vaccinated pigs treated with dexamethasone compared to vaccinated pigs that received a saline solution. This elevation was significantly different (P<0.05) for ileocecal lymph nodes, colon contents and cecum contents.

Figure 10:
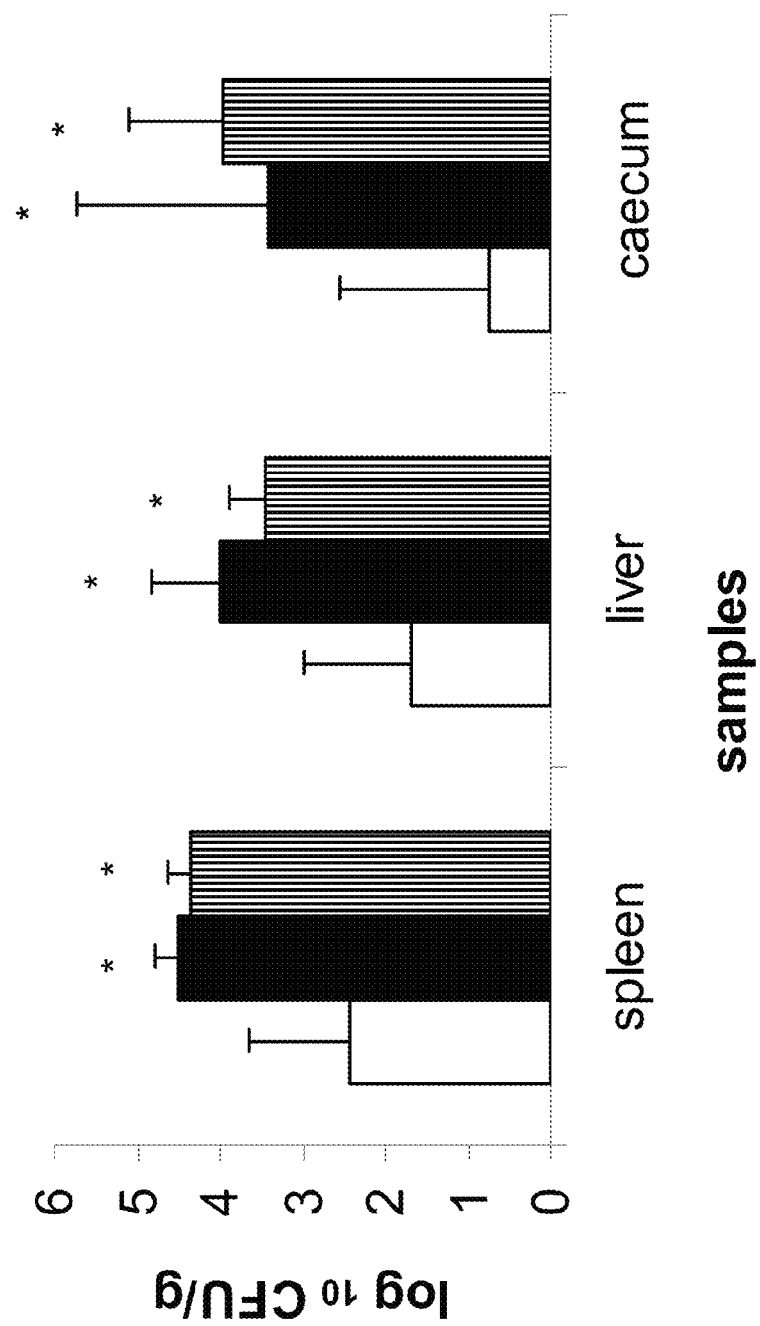
FIG. 10: Recovery of *Salmonella Typhimurium* 112910aNal[20] from various organs from DBA/2J mice 14 days post infection. Black bars represent infected DBA/2J mice that received a subcutaneous injection of dexamethasone (100 mg/kg) 24 h before euthanasia and white bars represent infected mice that received an subcutaneous injection of HBSS (control group). Striped bars represent DBA/2J mice that received 25 mg/kg dexamethasone 24 h and 21 h before euthanasia. The mean $\log_{10}$ values of the number of CFU per gram sample with their standard deviations are given. An asterisk (*) refers to a significant difference (P<0.05) between the control group and the dexamethasone group.

A Subcutaneous Injection of Dexamethasone Results in Recrudescence of *Salmonella Typhimurium* 112910Nal[20] in DBA/2J Mice but not in BALB/c Mice A mice model was optimized to demonstrate that a subcutaneous injection of 100 mg/kg dexamethasone (or two injections of 25 mg/kg with an interval of three hours) is capable to induce recrudescence of *Salmonella Typhimurium* is strain 112910aNal[20] in DBA/2J or BALB/c mice. *Salmonella* infected DBA/2J mice, subsequently injected with dexamethasone had a significantly (P<0.05) higher number of *Salmonella Typhimurium* bacteria in the spleen, the liver and the cecum, compared to DBA/2J mice that were injected with a saline solution. Results are shown in FIG. 10. Our study proved that *Salmonella Typhimurium* 112910a infections in DBA/2J mice are non-lethal. Bacterial growth in DBA/2J mice is controlled after several days and we assume that it reaches a plateau phase and subsequently declines, while in BALB/c mice the bacterial load in organ samples increases gradually (unpublished results). Therefore, DBA/2J mice and not BALB/c mice allowed us to investigate stress related recrudescence in animals that carry *Salmonella Typhimurium* asymptomatically.

Figure 11:
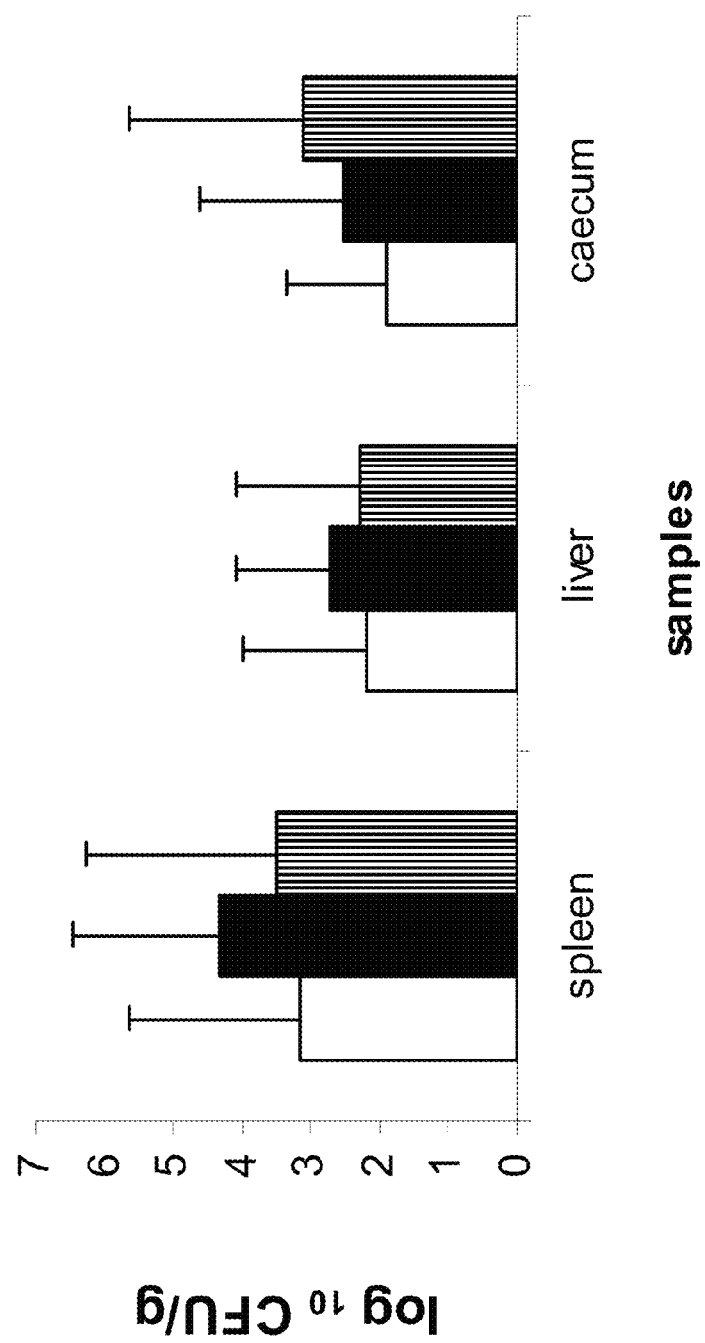
FIG. 11: Recovery of *Salmonella Typhimurium* 112910aNal20 from various organs from BALB/c mice 7 days post infection. Black bars represent infected BALB/c mice that received a subcutaneous injection of dexamethasone (100 mg/kg) 24 h before euthanasia and white bars represent infected mice that received an subcutaneous injection of HBSS (control group). Striped bars represent BALB/c mice that received 25 mg/kg dexamethasone 24 h and 21 h before euthanasia. The mean log 10 values of the number of CFU per gram sample with their standard deviations are given.
Figure 12:
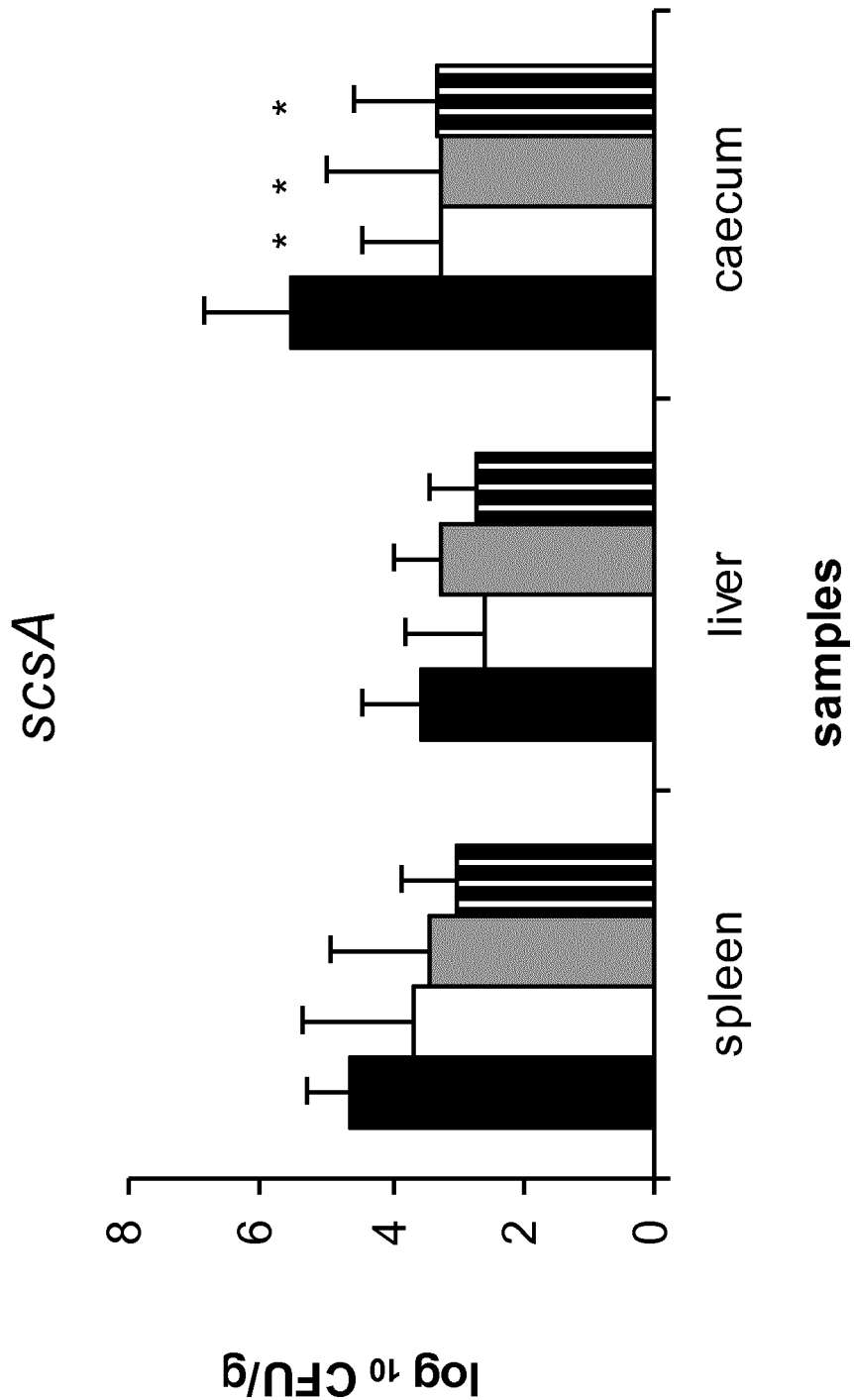
FIG. 12: Recovery of *Salmonella Typhimurium* 112910a (WT) and its isogenic scs (either scsA, scsB, scsC, scsD or scsABCD) knock-out mutants from various organs from mice 14 days post infection. Black bars represent WT infected DBA/2J mice that received a subcutaneous injection of dexamethasone (100 mg/kg) 24 h before euthanasia. White bars represent WT infected mice that received a subcutaneous injection of HBSS. Gray bars represent either ΔscsA, ΔscsB, ΔscsC, ΔscsD or ΔscsABCD infected DBA/2J is mice that received a subcutaneous injection of dexamethasone (100 mg/kg) 24 h before euthanasia. Striped bars represent either: ΔscsA, ΔscsB, ΔscsC, ΔscsD or ΔscsABCD infected mice that received a subcutaneous injection of HBSS. The mean $\log_{10}$ values of the number of CFU per gram sample with their standard deviations are given. An asterisk (*) refers to a significant difference (P<0.05) with the WT dexamethasone group.
Figure 12:
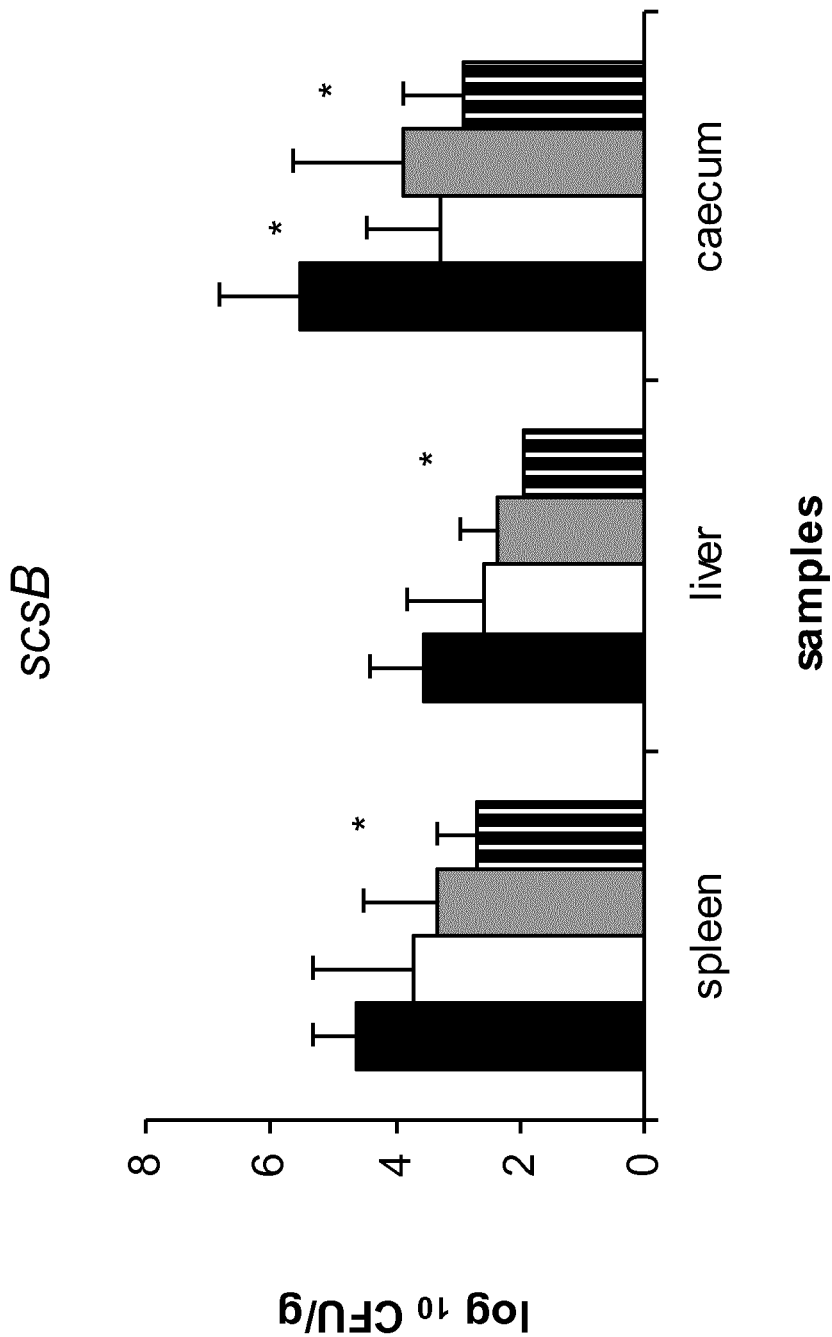
Figure 12:
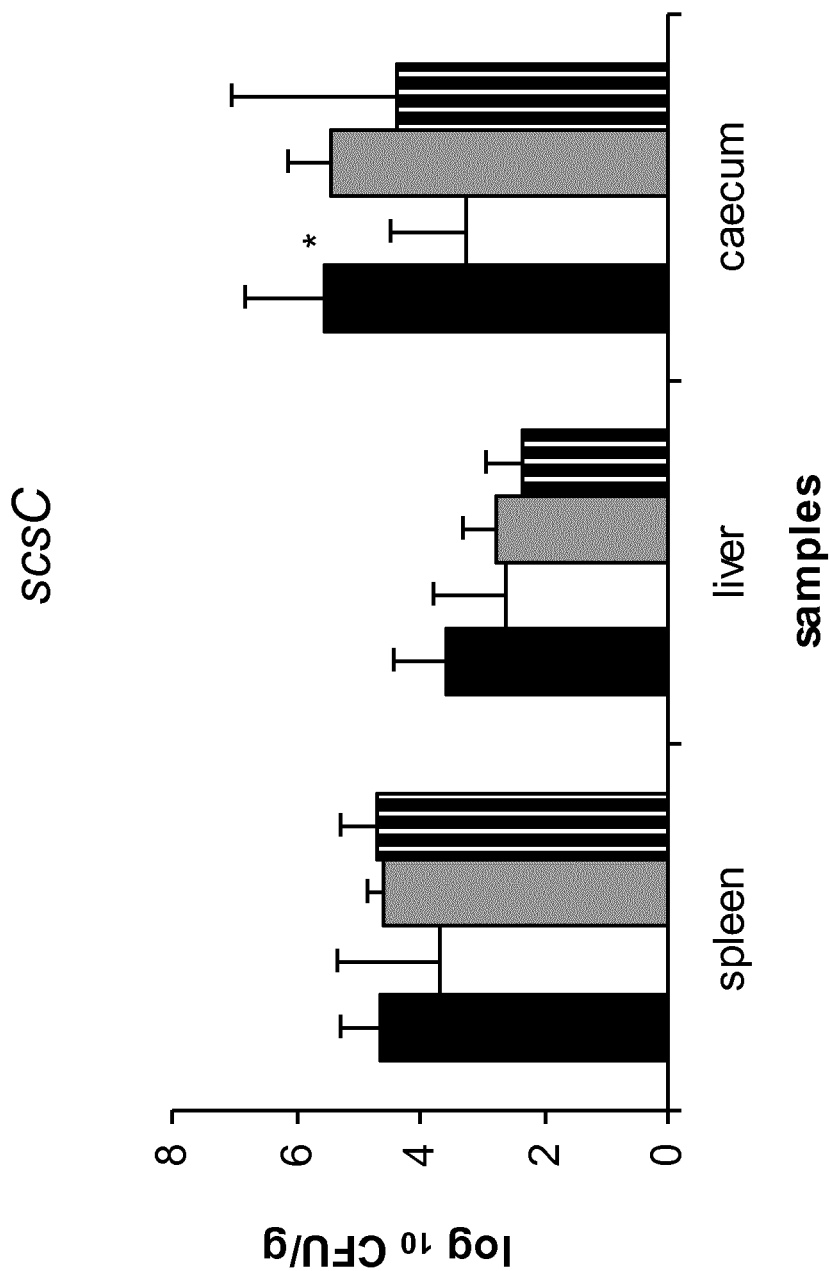
Figure 12:
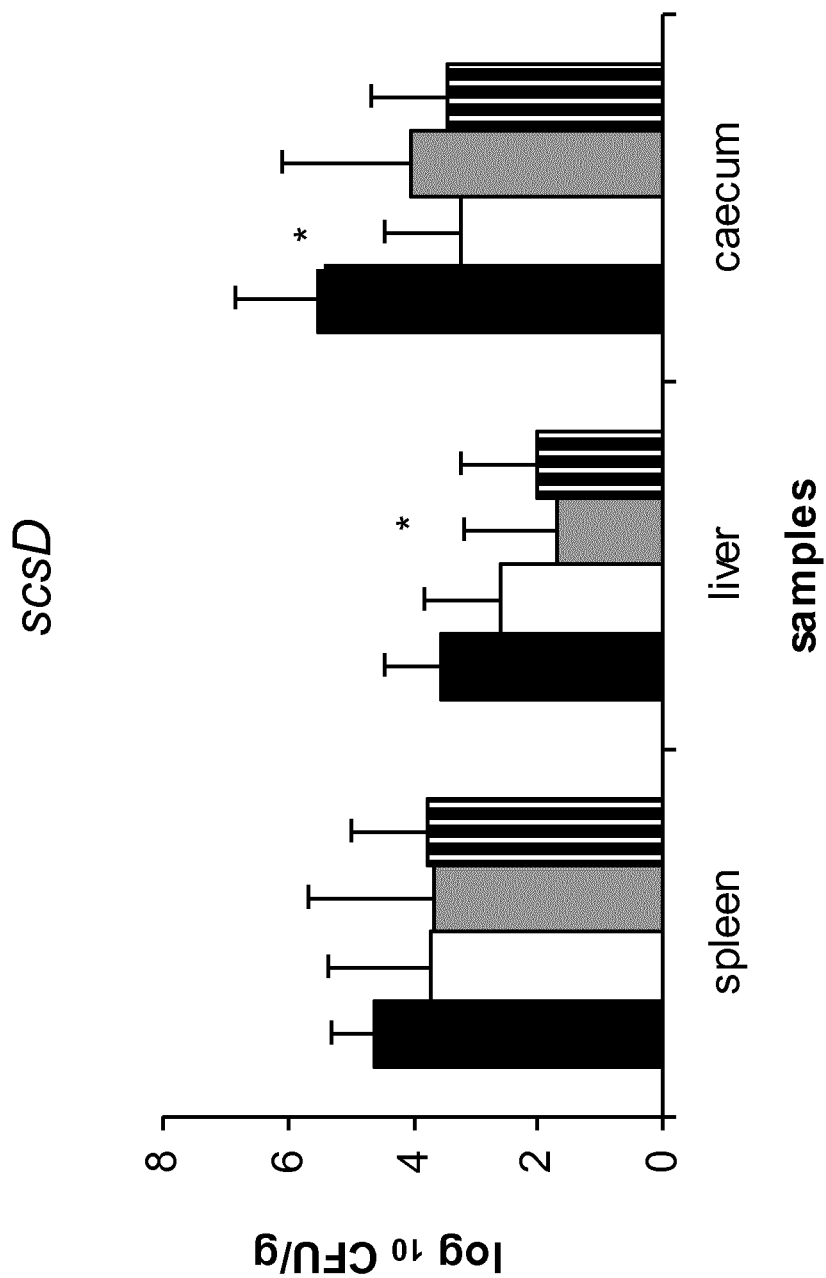
Figure 12:
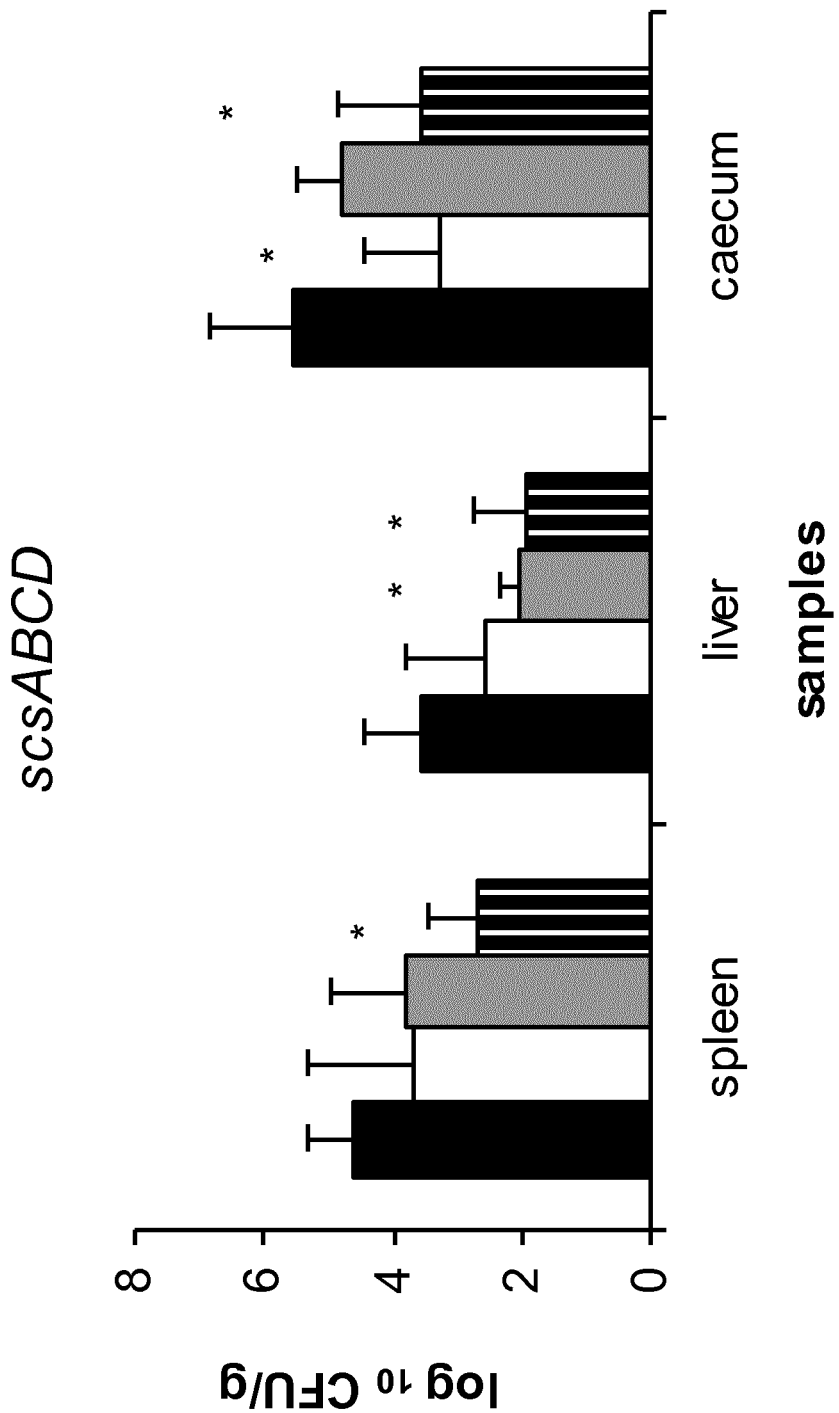

FIG. 11 shows that the number of *Salmonella Typhimurium* bacteria in organs of infected BALB/c mice, subsequently injected with dexamethasone, was not significantly different (P>0.05) from *Salmonella* numbers isolated from the spleen, the liver and the cecum of infected BALB/c mice that were injected with HBSS 24 h before euthanasia.

scsA and scsABCD Determine Dexamethasone Induced Recrudescence of *Salmonella Typhimurium* 112910a Bacterial counts in the spleen (P>0.05), liver (P>0.05) and caecum (P<0.05) of DBA/2J mice infected with ΔscsA and subsequently injected with 100 mg/kg dexamethasone, were reduced compared to bacterial numbers in organs of mice infected with its isogenic wild type strain, subsequently injected with dexamethasone. The *Salmonella Typhimurium* load in organ samples of mice, infected with ΔscsB or ΔscsC and subsequently injected with 100 mg/kg dexamethasone, was not significantly different from that in organs of DBA/2J mice infected with the wild type strain and subsequently injected with dexamethasone. The *Salmonella Typhimurium* load in the liver of mice is infected with ΔscsD or ΔscsABCD, subsequently injected with 100 mg/kg dexamethasone, was significantly different from that in the liver of DBA/2J mice infected with the wild type strain and subsequently injected with dexamethasone. Results are shown in FIGS. 12A-E.

None of the DBA/2J mice infected with ΔscsA, ΔscsABCD or their isogenic wild type strain died as a result of the infection, whereas eleven mice infected with either ΔscsB (n=3), ΔscsC (n=4) or ΔscsD (n=4) died as a consequence of challenge.

The DBA/2J mice model allowed us to investigate whether scs genes are able to reduce dexamethasone induced recrudescence of *Salmonella* in vivo. Our results indicated that mice infected with ΔscsA, ΔscsD or ΔscsABCD did not show recrudescence of *Salmonella Typhimurium* after a subcutaneous injection with dexamethasone. This was not the case for mice infected with either ΔscsB or ΔscsC. Furthermore, deletion of ΔscsB, ΔscsC or ΔscsD increased virulence of *Salmonella Typhimurium* 112910a in DBA/2J mice.

In conclusion, we showed that scsA and scsABCD are able to abolish dexamethasone induced recrudescence of *Salmonella* in a DBA/2J mice model, without increasing the virulence of the *Salmonella Typhimurium* strain used. Therefore, deletion of scsA or the entire scs locus in *Salmonella Typhimurium* live vaccines might help to reduce stress related recrudescence of live vaccine strains.

REFERENCES

Barth, S., Bauerfeind, R., 2005. Virulence plasmids of *Salmonella enterica*: incidence and properties. Berl. Munch. Tierarztl. Wochenschr. 118, 8-23.

Bauerfeind R, Barth S, Weiss R, Baljer G. Prevalence of the *Salmonella* plasmid virulence gene "spvD" in *Salmonella* strains from animals. Dtsch Tierarztl Wochenschr. 2001 June; 108(6):243-5.

Bearson B L, Bearson S M: The role of the QseC quorum-sensing sensor kinase in colonization and norepinephrine-enhanced motility of *Salmonella enterica* serovar *Typhimurium*. Microb Pathog 2008, 44(4):271-278.

Berends, B. R., Urlings, H. A. P., Snijders, J. M. A. and Van Knapen, F., 1996. Identification and quantification of risk factors in animal management and transport regarding *Salmonella* spp. in pigs. International Journal of Food Microbiology 30, pp. 37-53.

Bijttebier, J, Tilleman, K, Deforce, D, Dhaenens, M, Van Soom, A, and Maes, D (2009) Proteomic study to identify factors in follicular fluid and/or serum involved in in vitro cumulus expansion of porcine oocytes. *Soc. Reprod. Fertil.* Suppl. 66: 205-206.

Boyen F, Pasmans F, Donné E, Van Immerseel F, Adriaensen C, Hernalsteens J.-P, Ducatelle R., Haesebrouck F. 2006a. Role of SPI-1 in the interactions of *Salmonella Typhimurium* with porcine macrophages. Vet Microbiol. 113: 35-44.

Boyen F, Pasmans F, Van Immerseel F, Morgan E, Adriaensen C, Hernalsteens J P, et al. *Salmonella Typhimurium* SPI-1 genes promote intestinal but not tonsillar colonization in pigs. Microbes Infect. 2006b November-December; 8(14-15):2899-907.

Boyen, F., Pasmans, F., Donné, E., Van Immerseel, F., Morgan, E., Adriaensen, C., Hernalsteens, J. P., Wallis, T. S., Ducatelle, R., Haesebrouck, F., 2006c. The fibronectin binding protein ShdA is not a prerequisite for long term faecal shedding of *Salmonella typhimurium* in pigs. Vet Microbiol 115, 284-290.

Boyen F, Haesebrouck F, Maes D, Van Immerseel F, Ducatelle R, Pasmans F. 2008. Non-typhoidal *Salmonella* infections in pigs: a closer look at epidemiology, pathogenesis and control. Vet Microbiol. 130(1-2):1-19.

Boyen F, Pasmans F, Van Immerseel F, Donné E, Morgan E, Ducatelle R, Haesebrouck F. 2009a. Porcine in vitro and in vivo models to assess the virulence of *Salmonella enterica* serovar *Typhimurium* for pigs. Lab Anim. 43(1):46-52.

Boyen F, Eeckhaut V, Van Immerseel F, Pasmans F, Ducatelle R, Haesebrouck F. Quorum sensing in veterinary pathogens: mechanisms, clinical importance and future perspectives. Vet Microbiol. 2009b Mar. 30; 135(3-4):187-95

Boyen F, Pasmans F, Van Immerseel F, Morgan E, Botteldoorn N, Heyndrickx M, Volf J, Favoreel H, Hernalsteens J P, Ducatelle R et al: A limited role for SsrA/B in persistent *Salmonella Typhimurium* infections in pigs. Vet Microbiol 2008, 128(3-4):364-373.

Bradshaw, R. H., Parrott, R. F., Goode, J. A., Lloyd, D. M., Rodway, R. G. and Broom, D. M., 1996. Behavioural and hormonal responses of pigs during transport: effect of mixing and duration of journey. Animal Science 62, pp. 547-554.

Clements M O, Eriksson S, Thompson A, Lucchini S, Hinton J C, Normark S, Rhen M: Polynucleotide phosphorylase is a global regulator of virulence and persistency in *Salmonella enterica*. Proc Natl Acad Sci USA 2002, 99(13): 8784-8789.

Colaert, N, Van Huele, C, Degroeve, S, Staes, A, Vandekerckhove, J, Gevaert, K, and Martens, L (2011) Combining quantitative proteomics data processing workflows for greater sensitivity. Nat. Methods. 8: 481-483.

Datsenko K A, Wanner B L. One-step inactivation of chromosomal genes in *Escherichia coli* K-12 using PCR products. Proc Natl Acad Sci USA. 2000 Jun. 6; 97(12):6640-5.

Dhabhar F S: Enhancing versus suppressive effects of stress on immune function: implications for immunoprotection and immunopathology. Neuroimmunomodulation 2009, 16(5):300-317.

Dom P, Haesebrouck F, De Baetselier P: Stimulation and suppression of the oxygenation activity of porcine pulmonary alveolar macrophages by *Actinobacillus pleuropneumoniae* and its metabolites. Am J Vet Res 1992, 53(7): 1113-1118.

Donne E, Pasmans F, Boyen F, Van Immerseel F, Adriaensen C, Hernalsteens J P, Ducatelle R, Haesebrouck F: Survival of *Salmonella* serovar *Typhimurium* inside porcine monocytes is associated with complement binding and suppression of the production of reactive oxygen species. Vet Microbiol 2005, 107(3-4):205-214.

Eddicks, M., Palzer, A., Hörmansdorfer, S., Ritzmann, M., Heinritzi, K., 2009. Examination of the compatibility of a *Salmonella Typhimurium*-live vaccine Salmoporc for three day old suckling piglets. Deutschen Tierärztliche Wochenschrift. 116:249-254.

EFSA, Opinion of the Scientific Panel on Biological Hazards on the request from the Commission related to "Risk assessment and mitigation options of *Salmonella* in pig production", EFSA J. 341 (2006), pp. 1-131.

Farzan A, Friendship R M, Dewey C E. Evaluation of enzyme-linked immunosorbent assay (ELISA) tests and culture for determining *Salmonella* status of a pig herd. Epidemiol Infect 2007 February; 135(2):238-44.

Finlay B, Brumell J: *Salmonella* interactions with host cells: in vitro to in vivo. Philosophical Transactions of the Royal Society of London Series B-Biological Sciences 2000: 623-631.

Flaming K P, Gogg B L, Roth F, Roth J A: Pigs are relatively resistant to dexamethasone induced immunosuppression. In., vol. 4; 1994: 218-225.

Freestone P P, Lyte M: Microbial endocrinology: experimental design issues in the study of interkingdom signalling in infectious disease. Adv Appl Microbiol 2008, 64:75-105.

Gupta, S. D., Wu, N. C., Rick, P. D., 1997. A *Salmonella Typhimurium* genetic locus which confers copper tolerance on copper-sensitive mutants of *Escherichia coli*. Journal of Bacteriology. 179: 4977-4984.

Hald T, Wingstrand A, Swanenburg M, von Altrock A, Thorberg B M: The occurrence and epidemiology of *Salmonella* in European pig slaughterhouses. Epidemiol Infect 2003, 131(3):1187-1203.

Hensel M, Shea J E, Gleeson C, Jones M D, Dalton E, Holden D W. Simultaneous identification of bacterial virulence genes by negative selection. Science 1995 Jul. 21; 269 (5222):400-3.

Hitchcock P J, Leive L, Makela P H, Rietschel E T, Strittmatter W, Morrison D C. Lipopolysaccharide nomenclature: past, present, and future. J Bacteriol 1986 June; 166(3): 699-705.

Hurd H S, McKean J D, Griffith R W, Wesley I V, Rostagno M H: *Salmonella enterica* infections in market swine with and without transport and holding. Appl Environ Microbiol 2002, 68(5):2376-2381.

Isaacson R E, Firkins L D, Weigel R M, Zuckermann F A, DiPietro J A: Effect of transportation and feed withdrawal on shedding of *Salmonella typhimurium* among experimentally infected pigs. Am J Vet Res 1999, 60(9):1155-1158.

Jensen-Waern, M. and Nyberg, L., 1993. Valuable indicators of physical stress in porcine plasma. Journal of Veterinary Medicine, Series A 40, pp. 321-327

Linder, T., Springer, S., Selbitz, H. J., 2007. The use of a *Salmonella Typhimurium* live vaccine to control *Salmonella Typhimurium* in fattening pigs in field and effects on serological surveillance. Safepork 2007-Verona (Italy).

Lundberg U, Vinatzer U, Berdnik D, von Gabain A, Baccarini M: Growth phase-regulated induction of *Salmonella*-induced macrophage apoptosis correlates with transient expression of SPI-1 genes. J Bacteriol 1999, 181(11): 3433-3437.

Lyte M: Microbial endocrinology and infectious disease in the 21st century. Trends Microbiol 2004, 12(1):14-20.

Martin-Peláez S, Peralta B, Creus E, Dalmau A, Velarde A, Pérez J F, Mateu E, Martin-Orúe S M: Different feed withdrawal times before slaughter influence caecal fermentation and faecal *Salmonella* shedding in pigs. Vet J 2009, 182(3):469-473.

Methner U, Rabsch W, Reissbrodt R, Williams P H: Effect of norepinephrine on colonisation and systemic spread of *Salmonella enterica* in infected animals: role of catecholate siderophore precursors and degradation products. Int J Med Microbiol 2008, 298(5-6):429-439.

Nakamura M, Nagamine N, Takahashi T, Suzuki S, Sato S. Evaluation of the efficacy of a bacterin against *Salmonella enteritidis* infection and the effect of stress after vaccination. Avian Dis. 1994, 38(4):717-24.

Namimatsu T, Asai T, Osumi T, Imai Y, Sato S. 2006 Prevalence of the virulence plasmid in *Salmonella Typhimurium* isolates from pigs. J Vet Med. Sci. 68:187-8.

Nichols E F, Madera L, Hancock R E W. Immunomodulators as adjuvants for vaccines and antimicrobial therapy. Ann. N.Y. Acad. Sci. (2010) 1-16

Nikaido, H., 1996. Outer membrane. In: Neidhardt, F. C. Editor, 1996. *Escherichia* and *Salmonella*: Cellular and Molecular Biology (2nd ed.), ASM Press, Washington D.C., page 30.

Nollet N, Houf K, Dewulf J, De Kruif A, De Zutter L, Maes D: *Salmonella* in sows: a longitudinal study in farrow-to-finish pig herds. Vet Res 2005, 36(4):645-656.

Rhoads J M, Chen W, Chu P, Berschneider H M, Argenzio R A, Paradiso A M: L-glutamine and L-asparagine stimulate Na+-H+ exchange in porcine jejunal enterocytes. Am J Physiol 1994, 266(5 Pt 1):G828-838.

Rupprecht M, Salzer B, Raum B, Hornstein O P, Koch H U, Riederer P, Sofic E, Rupprecht R: Physical stress-induced secretion of adrenal and pituitary hormones in patients with atopic eczema compared with normal controls. *Exp Clin Endocrinol Diabetes* 1997, 105(1):39-45.

Rupprecht R, Holsboer F: Neuroactive steroids: mechanisms of action and neuropsychopharmacological perspectives. *Trends Neurosci* 1999, 22(9):410-416.

Ross, P L, Huang, Y N, Marchese, J N, Williamson, B, Parker, K, Hattan, S, Khainovski, N, Pillai, S, Dey, S, Daniels, S, Purkayastha, S, Juhasz, P, Martin, S, Bartlet-Jones, M, He, F, Jacobson, A, and Pappin, D J (2004) Multiplexed protein quantitation in *Saccharomyces cerevisiae* using amine-reactive isobaric tagging reagents. *Mol. Cell Proteomics* 3: 1154-1169.

Rychlik I, Gregorova D, Hradecka H. 2006 Distribution and function of plasmids in *Salmonella enterica*. Vet Microbiol. 112:1-10.

Sebastiani, G., Blais, V., Sancho, V., Vogel, S. N., Stevenson, M. M., Gros, P., Lapointe, J. M., Rivest, S., Malo, D., 2002. Host immune response to *Salmonella enterica* serovar *Typhimurium* infection in mice derived from wild strains. Infection and Immunity. 70:1997-2009.

Schierack P, Nordhoff M, Pollmann M, Weyrauch K D, Amasheh S, Lodemann U, Jores J, Tachu B, Kleta S, Blikslager A et al: Characterization of a porcine intestinal epithelial cell line for in vitro studies of microbial pathogenesis in swine. Histochem Cell Biol 2006, 125(3):293-305.

Shefrin A, Goldman R: Use of dexamethasone and prednisone in acute asthma exacerbations in pediatric patients. Canadian Family Physician 2009:704-706.

Slauch J M: How does the oxidative burst of macrophages kill bacteria? Still an open question. Mol Microbiol 2011.

Stabel T J et al, Effect of 2-deoxy-d-glucose induced stress on *Salmonella* choleraesuis shedding and persistence in swine. Res Vet Sci. 2004 June; 76(3):187-94.

Toscano M J, Stabel T J, Bearson S M D, Bearson B L, Lay D C: Cultivation of *Salmonella enterica* serovar *Typhimurium* in a norepinephrine-containing medium alters in vivo tissue prevalence in swine. In., vol. 43. J Exp Anim Sci; 2007: 329-338.

Van Immerseel F, De Buck J, Boyen F, Bohez L, Pasmans F, Volf J, Sevcik M, Rychlik I, Haesebrouck F, Ducatelle R: Medium-chain fatty acids decrease colonization and invasion through hilA suppression shortly after infection of chickens with *Salmonella enterica* serovar *Enteritidis*. Appl Environ Microbiol 2004, 70(6):3582-3587.

Van Parys A, Boyen F, Leyman B, Verbrugghe E, Haesebruck F, Pasmans R: *Salmonella Typhimurium* genes expressed during persistence in pigs. Plos Ones 2011, provisionally accepted Verbrugghe, E, Boyen, F, Parys, A V, Deun, K V, Croubels, S, Thompson, A, Shearer, N, Leyman, B, Haesebrouck, F, and Pasmans, F (2011) Stress induced *Salmonella Typhimurium* recrudescence in pigs coincides with cortisol induced increased intracellular proliferation in macrophages. *Vet. Res.* 42:118.

Wallis T S. *Salmonella* pathogenesis and immunity: we need effective multivalent vaccines. Vet J. 2001 161(2):104-6.

Wei S, Xu H, Xia D, Zhao R: Curcumin attenuates the effects of transport stress on serum cortisol concentration, hippocampal NO production, and BDNF expression in the pig. Domest Anim Endocrinol 2010, 39(4):231-239.

Williams L P, Newell K W: *Salmonella* excretion in joy-riding pigs. Am J Public Health Nations Health 1970, 60(5):926-929.

Wong D, Hald T, van der Wolf P, Swanenburg M: Epidemiology and control measures for *Salmonella* in pigs and pork. *Livestock Production Science* 2002:215-222.

Worsaae H, Schmidt M: Plasma cortisol and behaviour in early weaned piglets. *Acta Vet Scand* 1980, 21(4):640-657.

Ygberg S E, Clements M O, Rytkönen A, Thompson A, Holden D W, Hinton J C, Rhen M: Polynucleotide phosphorylase negatively controls spv virulence gene expression in *Salmonella enterica*. Infect Immun 2006, 74(2): 1243-1254.

---

The invention claimed is:

1. A *Salmonella* mutant strain having at least one genetic modification within the cbpA gene or having at least one genetic modification within the scs locus.

2. The *Salmonella* mutant strain of claim 1, wherein the genetic modification in the scs locus is located within the scsA, scsB, scsC, or scsD gene.

3. The *Salmonella* mutant strain of claim 1, wherein the genetic modification is a deletion of at least a portion of the cbpA gene or the scs locus.

4. The *Salmonella* mutant strain according to claim 1, wherein the *Salmonella* strain consists of *Salmonella enterica* subspecies *enterica*.

5. The *Salmonella* mutant strain according to claim 4, wherein the *Salmonella* strain consists of *Salmonella enterica* subspecies *enterica* serovar *Typhimurium* (*Salmonella Typhimurium*).

6. The *Salmonella* mutant strain according to claim 1, further comprising one or more additional mutations in a gene other than the cbpA gene or scs locus.

7. A composition comprising the *Salmonella* mutant strain of claim 1, and a pharmaceutically acceptable carrier or diluent.

8. A vaccine comprising the *Salmonella* mutant strain according to claim 1, and a pharmaceutically acceptable carrier or diluent.

9. The vaccine of claim 8 wherein the vaccine is a live attenuated vaccine.

10. A method for converting a *Salmonella* vaccine strain into a *Salmonella* mutant vaccine strain by introducing at least one genetic modification within the cbpA gene or the scs locus into said strain; said method comprising:
   obtaining a *Salmonella* vaccine strain;
   introducing a genetic modification within the cbpA gene or the scs locus of said vaccine strain; thereby obtaining said *Salmonella* mutant vaccine strain.

11. The method according to claim 10 where the genetic modification in the scs locus is located within the scsA, scsB, scsC, or scsD gene.

12. The method according to claim 10 wherein the genetic modification is a deletion of at least a portion of the cbpA gene or the scs locus.

13. The method of claim 10 wherein the *Salmonella* vaccine strain consists of *Salmonella enterica* strain.

14. The method of claim 13 wherein the *Salmonella enterica* strain consists of *Salmonella enterica* subspecies *enterica* serovar *Typhimurium* (*Salmonella Typhimurium*).

15. The method according to claim 10, wherein the *Salmonella* vaccine strain is an attenuated strain.

16. The method according to claim 10, further comprising:
   creating a PCR adjusted antibiotic resistance cassette,
   inserting a first helper plasmid into the *Salmonella* vaccine strain,
   substituting part or all of the cbpA gene or the scs locus with the PCR adjusted antibiotic resistance cassette,
   controlling the substitution with PCR and sequencing,
   inserting a second helper plasmid into the substituted target strain,
   deleting the antibiotic resistance cassette and the helper plasmids, and
   controlling the deletion with PCR and sequencing.

17. A method for preventing, inhibiting or reducing recrudescence of a *Salmonella* infection comprising administering a *Salmonella* mutant vaccine strain as defined in claim 10 to a subject in need thereof.

18. The method according to claim 17, wherein the recrudescence is stress-induced.

19. The method according to claim 17, wherein the subject is selected from the group consisting of a pig, poultry and cattle.

20. A method for immunization of pigs, poultry and cattle against *Salmonella* infection comprising administering a *Salmonella* mutant strain vaccine as defined in claim 10 to a subject in need thereof.

21. A method for administering an antigen heterologous to *Salmonella* to a subject for vaccination against an infectious agent comprising:
   providing a *Salmonella* mutant strain according to claim 1;
   introducing a heterologous nucleic molecule encoding the antigen into the *Salmonella* mutant strain; and
   administering said *Salmonella* mutant strain to a subject in need thereof.

* * * * *